US011510923B2

(12) United States Patent
Kuligowski et al.

(10) Patent No.: US 11,510,923 B2
(45) Date of Patent: *Nov. 29, 2022

(54) RUXOLITINIB FORMULATION FOR REDUCTION OF ITCH IN ATOPIC DERMATITIS

(71) Applicant: Incyte Corporation, Wilmington, DE (US)

(72) Inventors: Michael Kuligowski, Chadds Ford, PA (US); Kang Sun, Wallingford, PA (US); Michael Howell, Kennett Square, PA (US); May Grace E. Venturanza, Chadds Ford, PA (US); Jim Lee, Devon, PA (US)

(73) Assignee: Incyte Corporation, Wilmington, DE (US)

( * ) Notice: Subject to any disclaimer, the term of this patent is extended or adjusted under 35 U.S.C. 154(b) by 218 days.

This patent is subject to a terminal disclaimer.

(21) Appl. No.: 17/012,691

(22) Filed: Sep. 4, 2020

(65) Prior Publication Data
US 2021/0069195 A1 Mar. 11, 2021

Related U.S. Application Data

(60) Provisional application No. 63/020,668, filed on May 6, 2020, provisional application No. 62/983,252, filed on Feb. 28, 2020, provisional application No. 62/898,873, filed on Sep. 11, 2019, provisional application No. 62/897,059, filed on Sep. 6, 2019, provisional application No. 62/896,421, filed on Sep. 5, 2019.

(51) Int. Cl.
A61K 31/519 (2006.01)
A61K 9/06 (2006.01)
A61P 17/00 (2006.01)
A61K 9/107 (2006.01)
A61K 9/00 (2006.01)
A61K 31/4155 (2006.01)

(52) U.S. Cl.
CPC .......... A61K 31/519 (2013.01); A61K 9/0014 (2013.01); A61K 9/06 (2013.01); A61K 9/107 (2013.01); A61P 17/00 (2018.01)

(58) Field of Classification Search
CPC .............. A61K 31/519; A61K 31/4155; A61K 9/0014; A61K 9/06; A61K 9/107; A61P 17/00
See application file for complete search history.

(56) References Cited

U.S. PATENT DOCUMENTS 9,603,849 B2 3/2017 Ratti et al.
9,655,854 B2 5/2017 Yeleswaram et al.
10,004,755 B2 6/2018 Wang et al.
10,166,191 B2 1/2019 Ni et al.
2008/0312259 A1 12/2008 Rodgers et al.
2015/0250790 A1 9/2015 Parikh et al.
2020/0282051 A1 9/2020 Kim

FOREIGN PATENT DOCUMENTS

WO 2011003418 A1 1/2011
WO 2012003829 A1 1/2012

OTHER PUBLICATIONS

Copending U.S. Appl. No. 17/705,624, filed Mar. 2022, Kuligowski; Michael.*
Incyte Corporation, "A Study to Evaluate the Safety and Efficacy of Ruxolitinib Phosphate cream applied topically to aduts with Atopic Dermatitis", Clinicaltrials.gov, Jan. 5, 2017. (Year: 2017).*
Bao et al., "IL-4 regulates chemokine CCL26 in keratinocytes through the Jak1, 2/Stat6 signal transduction pathway: Implication for atopic dermatitis", Molecular Immunology 50 (2012) 91-97.
Barosi et al., "How can we know if new drugs are effective in myeloproliferative neoplasm-associated myelofibrosis?", Leukemia (2016) 30, 1453-1455.
Bissonnette et al., "Topical tofacitinib for atopic dermatitis: a phase IIa randomized trial", British Journal of Dermatology, 175, pp. 902-911 (2016).
Cosgrove et al., "Efficacy and safety of oclacitinib for the control of pruritus and associated skin lesions in dogs with canine allergic dermatitis", Veterinary Dermatol 24: 479-e114 (2013).
Feldman, et al., Journal of the American Academy of Dermatology (2016), 5(6), 1162-1170.
Fukuyama, et al., Eur J Pharmacol., 794:20-2 (Jan. 2017; epub Nov. 2016).
Gonzalez, et al., Journal of Veterinary Pharmacology and Therapeutics, (2014), 37(4), 317-324.
Howell MS, Kuo FI, Smith PA. Targeting the janus kinase family in autoimmune skin diseases. Front Immunol. 2019;10:2342.
Incyte Corporation, "A Study to Evaluate the Safety and Efficacy of Ruxolitinib Phosphate Cream Applied Topically to Adults With Atopic Dermatitis", Clinicaltrials.gov, Jan. 5, 2017.
International Search Report and Written Opinon for PCT/US2020/049404 dated Feb. 16, 2021.
Kim B, Sofen H, Kuligowski M, Venturanza M, Sun K, Toth D. Effects of Ruxolitinib Cream on Pruritus and Quality of Life in Adult Patients With Atopic Dermatitis: Results from a Phase 2, Randomized, Dose-Ranging, Vehicle- and Active-Controlled Study . American Academy of Dermatology—77th Annual Meeting. 2019 (Abstract).
Kim B, Sofen H, Kuligowski M, Venturanza M, Sun K, Toth D. Effects of ruxolitinib cream on pruritus and quality of life in adult patients with atopic dermatitis: results from a phase 2, randomized, dose-ranging, vehicle- and active-controlled study . Maui Derm for Dermatologists—16th Annual Meeting. 2020 (Abstract).

(Continued)

Primary Examiner — Joseph R Kosack
Assistant Examiner — Sagar Patel
(74) Attorney, Agent, or Firm — Finnegan, Henderson, Farabow, Garrett & Dunner, LLP

(57) ABSTRACT

This disclosure relates to methods of reducing itch in patients with atopic dermatitis and treating patients with atopic dermatitis by administering a topical 0.75% or 1.5% ruxolitinib cream two times per day.

18 Claims, 33 Drawing Sheets

(56) References Cited

OTHER PUBLICATIONS

Kim B, Sofen H, Kuligowski M, Venturanza M, Sun K, Toth D. Effects of ruxolitinib cream on pruritus and quality of life in adult patients with atopic dermatitis: results from a phase 2, randomized, dose-ranging, vehicle- and active-controlled study . Maui Derm for Dermatologists—16th Annual Meeting. 2020 (poster).
Kim B, Sofen H, Kuligowski M, Venturanza M, Sun K, Toth D. Effects of ruxolitinib cream on pruritus and quality of life in adult patients with atopic dermatitis: results from a phase 2, randomized, dose-ranging, vehicle- and active-controlled study . Winter Clinical Dermatology Conference 2020 (Abstract).
Kim B, Sofen H, Kuligowski M, Venturanza M, Sun K, Toth D. Effects of ruxolitinib cream on pruritus and quality of life in adult patients with atopic dermatitis: Results from a phase 2, randomized, dose-ranging, vehicle- and active-controlled study. Revolutionizing Atopic Dermatitis—2019 (Abstract).
Kim BS, Howell MD, Sun K, Papp K, Nasir A, Kuligowski ME. Treatment of atopic dermatitis with ruxolitinib cream (JAK1/JAK2 Inhibitor) and triamcinolone cream . J Allergy Clin Immunol.
Kim BS, Nasir A, Papp K, Parish LC, Kuligowski M, Venturanza M, Sun K, Fowler JF. A Phase 2, Randomized, Dose-Ranging, Vehicle- and Active-Controlled Study to Evaluate the Safety and Efficacy of Topical Ruxolitinib in Adult Patients With Atopic Dermatitis. European Academy of Dermatology and Venereology—27th Congress. 2018 (Abstract).
Kim BS, Nasir A, Papp K, Parish LC, Kuligowski ME, Venturanza M, Sun K, Fowler JF. A phase 2, randomized, dose-ranging, vehicle- and active-controlled study to evaluate the safety and efficacy of ruxolitinib cream in adult patients with atopic dermatitis. European Academy of Dermatology and Venereology—27th Congress. 2018 (presentation).
Kim BS, Nasir A, Papp K, Parish LC, Kuligowski ME, Venturanza M, Sun K, Fowler JF. A Phase 2, Randomized, Dose-Ranging, Vehicle- and Active-Controlled Study to Evaluate the Safety and Efficacy of Ruxolitinib Cream in Adult Patients With Atopic Dermatitis. Revolutionizing Atopic Dermatitis—2019. 2019 (Abstract).
Kim BS, Nasir A, Papp K, Parish LC, Kuligowski ME, Venturanza M, Sun K, Fowler JF. A phase 2, randomized, dose-ranging, vehicle- and active-controlled study to evaluate the safety and efficacy of ruxolitinib cream in adult patients with atopic dermatitis. Revolutionizing Atopic Dermatitis—2019. 2019 (poster).
Kim BS, Sofen HL, Kuligowski ME, Venturanza M, Sun K, Toth D. Effects of ruxolitinib cream on pruritus and quality of life in adult patients with atopic dermatitis: Results from a phase 2, randomized, dose-ranging, vehicle- and active-controlled study. American Academy of Dermatology—77th Annual Meeting. 2019 (poster).
Kim BS, Sun K, Papp K, Venturanza M, Nasir A, Kuligowski ME. Effects of ruxolitinib cream on pruritus and quality of life in atopic dermatitis: Results from a phase 2, randomized, dose-ranging, vehicle- and active-controlled study. J Am Acad Dermatol. 2020.
Mesa et al., "Original Article" Changes in Quality of Life and Disease-Related Symptoms in Patients With Polycythemia Vera Receiving Ruxolitinib or Standard Therapy Nov. 18, 2015.
Nakagawa et al., "Pyridone 6, a Pan-JAK Inhibitor, Ameliorates Allergic Skin Inflammation of NC/Nga Mice via Suppression of Th2 and Enhancement of Th17", J. Immunol. 2011; 187:4611-4620.
Owens S, Liu H, Sun K, Venturanza M, Kuligowski M, Howell MD. Ruxolitinib cream significantly modulates inflammatory profiles of atopic dermatitis patients. Society for Investigative Dermatology—77th Annual Meeting. 2019 (Abstract).
Owens S, Rumberger B, Sun K, Venturanza M, Kuligowski M, Howell MD. Ruxolitinib cream suppresses Th2 inflammation in adult patients with atopic dermatitis . American Academy of Allergy, Asthma & Immunology—75th Annual Meeting. 2019.
Owens S, Rumberger B, Sun K, Venturanza M, Kuligowski M, Howell MD. Ruxolitinib cream suppresses Th2 inflammation in adult patients with atopic dermatitis . American Academy of Allergy, Asthma & Immunology—75th Annual Meeting. 2019 (poster).
Owens S, Sun K, Jones H, Kuligowski M, Howell MD. Association Between an Itch-Free State in Atopic Dermatitis Treated with Ruxolitinib Cream and Systemic Inflammatory Mediators. American Academy of Dermatology—78th Annual Meeting. 2020 (Abstract).
Owens S, Sun K, Jones H, Kuligowski M, Howell MD. Association Between an Itch-Free State in Atopic Dermatitis Treated with Ruxolitinib Cream and Systemic Inflammatory Mediators. American Academy of Dermatology—78th Annual Meeting. 2020 (presentation).
Owens S, Sun K, Jones H, Kuligowski M, Howell MD. Association Between an Itch-Free State in Atopic Dermatitis Treated with Ruxolitinib Cream and Systemic Inflammatory Mediators. Revolutionizing Atopic Dermatitis—2020. 2020 (Abstract).
Owens S, Sun K, Jones H, Kuligowski M, Howell MD. Association Between an Itch-Free State in Atopic Dermatitis Treated With Ruxolitinib Cream and Systemic Inflammatory Mediators. Revolutionizing Atopic Dermatitis—2020. 2020; (poster).
Papp K, Szepietowski J, Kircik L, Toth D, Kuligowski M, Venturanza M, Sun K, Simpson E . Efficacy and safety of ruxolitinib cream for the treatment of atopic dermatitis: Results from two phase 3, randomized, double-blind studies. Revolutionizing Atopic Dermatitis—2020. 2020 (Abstract).
Papp K, Szepietowski J, Kircik L, Toth D, Kuligowski M, Venturanza M, Sun K, Simpson E. Efficacy and safety of ruxolitinib cream for the treatment of atopic dermatitis: Results from two phase 3, randomized, double-blind studies. Maui Derm NP+PA Summer 2020 Meeting. 2020 (Abstract).
Papp K, Szepietowski J, Kircik L, Toth D, Kuligowski M, Venturanza M, Sun K, Simpson E. Efficacy and safety of ruxolitinib cream for the treatment of atopic dermatitis: results from two phase 3, randomized, double-blind studies. Maui Derm NP+PA Summer 2020 Meeting. 2020 (poster).
Parker M, Fay B, Yao W, Smith P . Ruxolitinib cream ameliorates spontaneous atopic dermatitis in the IL-33 transgenic mouse model. European Society for Dermatological Research—49th Annual Meeting. 2019 (Abstract).
Parker M, Fay B, Yao W, Smith P . Ruxolitinib cream ameliorates spontaneous atopic dermatitis in the IL-33 transgenic mouse model. European Society for Dermatological Research—49th Annual Meeting. 2019 (poster).
Parker M, Scuron M, Fay B, Huarte E, Collins R, Yao W, Smith P . Ruxolitinib cream ameliorates a preclinical model of skin dermatitis via modulation of inflammatory T-cell subsets. European Society for Dermatological Research—49th Annual Meeting. 2019 (Abstract).
Parker M, Scuron M, Fay B, Huarte E, Collins R, Yao W, Smith P. Ruxolitinib cream ameliorates a preclinical model of skin dermatitis via modulation of inflammatory T-cell subsets. European Society for Dermatological Research—49th Annual Meeting. 2019 (poster).
Raoof T, Kircik L, Kuligowski M, Venturanza M, Sun K, Tan J. 12-week efficacy and safety data of ruxolitinib cream in adult patients with atopic dermatitis: results from a phase 2 study . World Congress of Dermatology—25th. 2023 (Abstract).
Raoof T, Kircik L, Kuligowski ME, Venturanza M, Sun K, Tan J. 12-week efficacy and safety data of ruxolitinib cream in adult patients with atopic dermatitis: Results from a phase 2 study. World Congress of Dermatology—24th. 2019 (presentation).
Song et al., "Ruxolitinib found to cause eyelash growth: a case report", Journal of Medical Case Reports (2017) 11:189; pp. 1-6.
Stiefel, British Journal of Dermatology, (May 1, 2016) vol. 174, No. 5, pp. 985-995.
Vaa et al., "Pruruitus in primary myelofibrosis: management options in the era of JAK inhibitors", Am Hematol (2016) 95: 1185-1189.
Verstovsek et al., "A Phase 2 Study of Ruxolitinib, an Oral JAK1 and JAK2 Inhibitor, in Patients With Advanced Polycythemia Vera Who Are Refactory or Intolerant to Hydroxyurea", Cancer, Feb. 15, 2014, vol. 120, No. 4, p. 513-520.
Xu, et al., J. Am. Acad. Dermatol. 74(5):1017-1020 (May 2016).
Yashuda, J Clin Invest. Jun. 1, 2016; 126(6): 2064-2076.
Simpson, et al., Two Phase 3 Trials of Dupilumab versus Placebo in Atopic Dermatitis, N Engl J Med 2016; 375: 2335-48.

(56) References Cited

OTHER PUBLICATIONS

Investor and Analyst Event, "Incyte: Building Value through Innovative Medicines," Jun. 21, 2018.

* cited by examiner

RUXOLITINIB FORMULATION FOR REDUCTION OF ITCH IN ATOPIC DERMATITIS

CROSS-REFERENCE TO RELATED APPLICATIONS

This application claims priority to U.S. Provisional Application No. 62/896,421, filed Sep. 5, 2019, U.S. Provisional Application No. 62/897,059, filed Sep. 6, 2019, U.S. Provisional Application No. 62/898,873, filed Sep. 11, 2019, U.S. Provisional Application No. 62/983,252, filed Feb. 28, 2020, and U.S. Provisional Application No. 63/020,668, filed May 6, 2020, each of which is incorporated herein by reference in its entirety.

TECHNICAL FIELD

This disclosure relates to methods of reducing itch in patients with atopic dermatitis and treating patients with atopic dermatitis by administering a topical ruxolitinib cream, including 0.75% or 1.5% ruxolitinib cream two times per day.

BACKGROUND

Atopic dermatitis affects approximately 10% of adults (Silverberg J I, Hanifin J M. *J Allergy Clin Immunol* 2013; 132:1132-1138), is increasing in incidence, and costs $3.8 billion a year in direct medical costs alone (Ellis CN, et al. *J Am Acad Dermatol* 2002; 46:361-370). According to the recent Global Burden of Disease project, worldwide Atopic dermatitis ("AD") is one of the 50 most prevalent diseases, and it has the second highest disability rank of all nonmalignant skin diseases (Hay RJ, et al. *J Invest Dermatol* 2014; 134:1527-1534). Despite the advances in targeted and numerous biologic treatments for psoriasis, only one such a therapy currently exist for AD (Dupixent®).

One of the main characteristics and a diagnostic criterion of AD is pruritus (itch). Itching brings about scratching, which in turn further damages the AD skin, aggravates the disease and my lead to secondary infections. Further, nocturnal itching and scratching can result in sleep loss and impairment in quality of life for patients and for their immediate family members, e.g., parents of a child with AD.

Topical therapies for AD are limited to topical steroids, topical calcineurin inhibitors and more recently a PDE4 inhibitor (Eucrisa®). These drugs have all limitations related to their efficacy levels, safety (particularly long-term use) or tolerability issues. Topical steroids use can also be associated with irreversible side effects, such as skin atrophy or striae distensae. The use of systemic glucocorticoids and calcineurin inhibitors is also limited because of their adverse event (AE) profiles. If current topical therapies fail, then systemic immunosuppressive agents (e.g., cyclosporine, methotrexate) are occasionally employed with highly variable efficacy and/or high risk of AEs.

Importantly, none of the presently available drugs exerts a direct effect on itch alleviation. Therefore, new approaches to promptly and effectively control itch in patients with AD are needed. As mentioned, itch is the cardinal feature of AD and the symptom that leads directly to a high disease (quality of life) burden in this condition. This disclosure addresses this need and others.

SUMMARY

The present disclosure provides, inter alia, methods of reducing itch in and treating human patients having atopic dermatitis using ruxolitinib. Ruxolitinib is a potent JAK1/JAK2 inhibitor, (R)-3-(4-(7H-pyrrolo[2,3-d]pyrimidin-4-yl)-1H-pyrazol-1-yl)-3-cyclopentylpropanenitrile (INCB018424; ruxolitinib; active ingredient in JAKAFI®), and its pharmaceutically acceptable salts, has previously been described in U.S. Pat. No. 7,598,257, which is incorporated herein by reference in its entirety. Ruxolitinib phosphate was previously described in U.S. Patent Publ. No. 2008/0312259, which is incorporated herein by reference in its entirety.

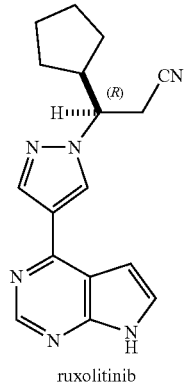

ruxolitinib

For example, methods are provided for treating atopic dermatitis in a human patient, the method comprising administering to the skin of the human patient in need thereof, a cream formulation comprising ruxolitinib or a pharmaceutically acceptable salt thereof. In other examples, provided are methods of reducing itch in a human patient with atopic dermatitis, the method comprising administering to the skin of the human patient in need thereof, a cream formulation comprising ruxolitinib or a pharmaceutically acceptable salt thereof, wherein the patient achieves a reduction in the itch Numerical Rating Scale score from baseline.

The present disclosure also provides methods of reducing itch in a human patient with atopic dermatitis, comprising administering to the skin of said human patient in need thereof, a cream formulation two times per day, wherein said cream formulation comprises 1.5% (w/w) on a free base basis of ruxolitinib, or a pharmaceutically acceptable salt thereof, wherein said patient achieves a reduction in the itch Numerical Rating Scale score from baseline.

The present disclosure also provides methods of reducing itch in a human patient with atopic dermatitis, comprising administering to the skin of said human patient in need thereof, a cream formulation two times per day, wherein said cream formulation comprises 0.75% (w/w) on a free base basis of ruxolitinib, or a pharmaceutically acceptable salt thereof, wherein said patient achieves a reduction in the itch Numerical Rating Scale score from baseline.

The present disclosure further provides methods of reducing itch in a human patient with atopic dermatitis, comprising administering to the skin of said human patient in need thereof, a cream formulation two times per day (BID), wherein said cream formulation comprises 1.5% (w/w) on a free base basis of ruxolitinib phosphate, wherein said patient achieves a reduction in the itch Numerical Rating Scale score from baseline.

The present disclosure also provides methods of reducing itch in a human patient with atopic dermatitis, comprising administering to the skin of said human patient in need thereof, a cream formulation two times per day (BID), wherein said cream formulation comprises 0.75% (w/w) on a free base basis of ruxolitinib phosphate, wherein said patient achieves a reduction in the itch Numerical Rating Scale score from baseline.

The present disclosure also provides methods of reducing itch in a human patient with atopic dermatitis, comprising administering to the skin of said human patient in need thereof, a cream formulation two times per day (BID), wherein said cream formulation comprises 0.75% (w/w) on a free base basis of ruxolitinib phosphate, wherein said patient achieves a reduction in the itch Numerical Rating Scale score from baseline.

The present disclosure further provides methods of treating atopic dermatitis in a human patient, comprising administering to the skin of said human patient in need thereof, a cream formulation two times per day, wherein said cream formulation comprises 0.75% (w/w) on a free base basis of ruxolitinib, or a pharmaceutically acceptable salt thereof.

The present disclosure further provides methods of treating atopic dermatitis in a human patient, comprising administering to the skin of said human patient in need thereof, a cream formulation two times per day, wherein said cream formulation comprises 0.75% (w/w) on a free base basis of ruxolitinib phosphate. The present disclosure also provides methods of reducing itch in a human patient with atopic dermatitis, comprising administering to the skin of said human patient in need thereof, a cream formulation two times per day, wherein said cream formulation is an oil-in-water emulsion, comprising 1.5% (w/w) on a free base basis of ruxolitinib phosphate, wherein the administering is maintained for at least 8 weeks (e.g., such as for 12 weeks), wherein the patient achieves at least a 4 point reduction in itch Numerical Rating Scale score from baseline at week 8 of the administering.

The present disclosure also provides methods of reducing itch in a human patient with atopic dermatitis, comprising administering to the skin of said human patient in need thereof, a cream formulation two times per day, wherein said cream formulation is an oil-in-water emulsion, comprising 0.75% (w/w) on a free base basis of ruxolitinib phosphate, wherein the administering is maintained for at least 8 weeks (e.g., such as for 12 weeks), wherein the patient achieves at least a 4 point reduction in itch Numerical Rating Scale score from baseline at week 8 of the administering.

The present disclosure further provides methods of reducing itch in a human patient with atopic dermatitis, comprising administering to the skin of said human patient in need thereof, a cream formulation two times per day, wherein said cream formulation is an oil-in-water emulsion, comprising 1.5% (w/w) on a free base basis of ruxolitinib phosphate, wherein the administering is maintained for at least 8 weeks, wherein the patient achieves at least a 4 point reduction in itch Numerical Rating Scale score from baseline at week 8 of said administering, and wherein the patient:
is aged 18 to 70 years,
has been diagnosed with atopic dermatitis for at least 2 years, has an Investigator's Global Assessment score of 2 to 3 at screening and baseline, and has a Body Surface Area of atopic dermatitis involvement (excluding face and intertriginous areas) of 3% to 20% at baseline.

The present disclosure further provides methods of reducing itch in a human patient with atopic dermatitis, comprising administering to the skin of said human patient in need thereof, a cream formulation two times per day, wherein said cream formulation is an oil-in-water emulsion, comprising 0.75% (w/w) or 1.5% (w/w) on a free base basis of ruxolitinib phosphate, wherein the administering is maintained for at least 8 weeks, wherein the patient achieves at least a 4 point reduction in itch Numerical Rating Scale score from baseline at week 8 of said administering, and wherein the patient:
is an adolescent aged ≥12 to 17, inclusive, or a man or woman aged ≥18 years;
has history of AD for at least 2 years;
has an Investigator's Global Assessment score of 2 to 3 at baseline; and
has a % BSA of AD involvement, excluding the scalp, of 3% to 20% at baseline.

The present disclosure also provides methods of reducing itch in a human patient with atopic dermatitis, comprising administering to the skin of said human patient in need thereof, a cream formulation two times per day, wherein said cream formulation is an oil-in-water emulsion, comprising 1.5% (w/w) on a free base basis of ruxolitinib phosphate, wherein the administering is maintained for at least 8 weeks, wherein the patient achieves at least a 4 point reduction in itch Numerical Rating Scale score from baseline at week 8 of said administering, and wherein the patient achieves an Investigator's Global Assessment score of 0 or 1 with an improvement of at least 2 points from baseline at 8 weeks of said administering.

The present disclosure also provides methods of reducing itch in a human patient with atopic dermatitis, comprising administering to the skin of said human patient in need thereof, a cream formulation two times per day, wherein said cream formulation is an oil-in-water emulsion, comprising 0.75% (w/w) on a free base basis of ruxolitinib phosphate, wherein the administering is maintained for at least 8 weeks, wherein the patient achieves at least a 4 point reduction in itch Numerical Rating Scale score from baseline at week 8 of said administering, and wherein the patient achieves an Investigator's Global Assessment score of 0 or 1 with an improvement of at least 2 points from baseline at 8 weeks of said administering.

The present disclosure further provides methods of reducing itch in a human patient with atopic dermatitis, comprising administering to the skin of said human patient in need thereof, a cream formulation two times per day, wherein said cream formulation is an oil-in-water emulsion, comprising 1.5% (w/w) on a free base basis of ruxolitinib phosphate, wherein the administering is maintained for at least 8 weeks, wherein the patient achieves at least a 4 point reduction in itch Numerical Rating Scale score from baseline at week 8 of said administering, wherein the patient achieves an Investigator's Global Assessment score of 0 or 1 with an improvement of at least 2 points from baseline at 8 weeks of said administering, and
wherein the patient:
is aged 18 to 70 years,
has been diagnosed with atopic dermatitis for at least 2 years,
has an Investigator's Global Assessment score of 2 to 3 at screening and baseline, and
has a Body Surface Area of atopic dermatitis involvement (excluding face and intertriginous areas) of 3% to 20% at baseline.

The present disclosure further provides methods of reducing itch in a human patient with atopic dermatitis, comprising administering to the skin of said human patient in need thereof, a cream formulation two times per day, wherein said cream formulation is an oil-in-water emulsion, comprising 0.75% (w/w) or 1.5% (w/w) on a free base basis of ruxolitinib phosphate,
wherein the administering is maintained for at least 8 weeks,
wherein the patient achieves at least a 4 point reduction in itch Numerical Rating Scale score from baseline at week 8 of said administering,
wherein the patient achieves an Investigator's Global Assessment score of 0 or 1 with an improvement of at least 2 points from baseline at 8 weeks of said administering, and
wherein the patient:
is an adolescent aged ≥12 to 17, inclusive, or a man or woman aged ≥18 years;
has history of AD for at least 2 years;
has an Investigator's Global Assessment score of 2 to 3 at baseline; and
has a % BSA of AD involvement, excluding the scalp, of 3% to 20% at baseline.

The present disclosure also provides methods of treating moderate atopic dermatitis in a human patient comprising administering to the skin of said human patient in need thereof, a topical formulation two times per day, wherein said topical formulation comprises 0.75% (w/w) or 1.5% (w/w) on a free base basis of ruxolitinib, or a pharmaceutically acceptable salt thereof.

The present disclosure also provides methods of treating moderate to severe atopic dermatitis in a human patient comprising administering to the skin of said human patient in need thereof, a topical formulation two times per day, wherein said topical formulation comprises 0.75% (w/w) or 1.5% (w/w) on a free base basis of ruxolitinib, or a pharmaceutically acceptable salt thereof.

The present disclosure also provides methods of treating atopic dermatitis in a human patient comprising administering to the skin of said human patient in need thereof, a topical formulation two times per day, wherein the topical formulation comprises 0.75% (w/w) or 1.5% (w/w) on a free base basis of ruxolitinib, or a pharmaceutically acceptable salt thereof,
wherein said patient has: an Eczema Area and Severity Index score of ≥16 at baseline; and
a Body Surface Area of atopic dermatitis involvement of ≥10% at baseline.

The present disclosure further provides a topical formulation (e.g., a cream formulation) comprising 0.75% (w/w) on a free base basis of ruxolitinib, or a pharmaceutically acceptable salt thereof, for use in any of the methods described herein.

The present disclosure also provides a topical formulation (e.g., a cream formulation) comprising 1.5% (w/w) on a free base basis of ruxolitinib, or a pharmaceutically acceptable salt thereof, for use in any of the methods described herein.

The present disclosure further provides use of a topical formulation (e.g., a cream formulation) comprising 0.75% (w/w) on a free base basis of ruxolitinib, or a pharmaceutically acceptable salt thereof, for manufacture of a medicament for use in any of the methods described herein.

The present disclosure further provides use of a topical formulation (e.g., a cream formulation) comprising 1.5% (w/w) on a free base basis of ruxolitinib, or a pharmaceutically acceptable salt thereof, for manufacture of a medicament for use in any of the methods described herein.

DESCRIPTION OF DRAWINGS

"RUX" in the Figures is ruxolitinib phosphate. TAC in the Figures is triamcinolone.

DETAILED DESCRIPTION

Figure 1:
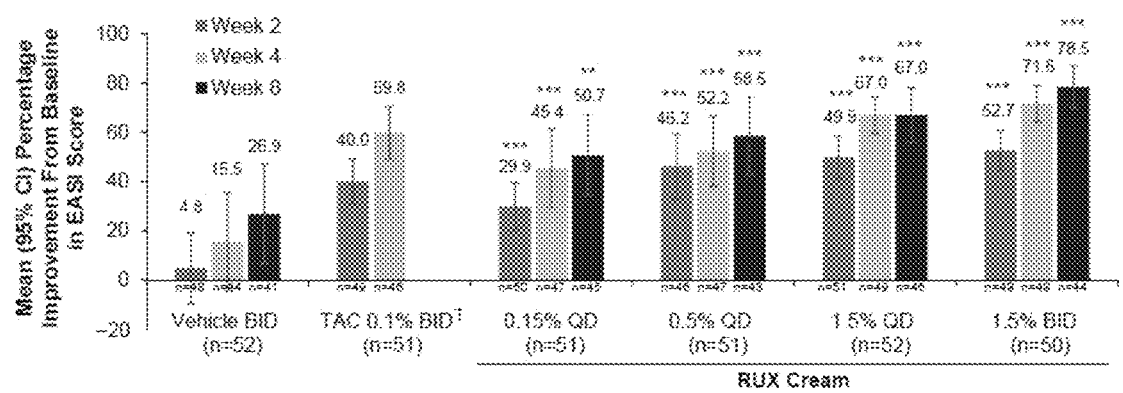
FIG. 1 shows a graph of mean percentage improvement from baseline in EASI scores for vehicle (BID), triamcinolone (0.1% BID), and ruxolitinib cream (0.15% QD, 0.5% QD, 1.5% QD, and 1.5% BID) at week 2 (first graph bar of each set), week 4 (second graph bar of each set) and week 8 (third graph bar of each set). 0.1% TAC does not show a bar because TAC was only administered for 4 weeks.

The present disclosure provides, inter alia, a method of reducing itch in a human patient with atopic dermatitis, comprising administering to the skin of said human patient in need thereof, a cream formulation two times per day, wherein said cream formulation comprises 1.5% (w/w) on a free base basis of ruxolitinib, or a pharmaceutically acceptable salt thereof, wherein said patient achieves a reduction in the itch Numerical Rating Scale score from baseline.

The present disclosure also provides a method of reducing itch in a human patient with atopic dermatitis, comprising administering to the skin of said human patient in need thereof, a cream formulation two times per day, wherein said cream formulation comprises 0.75% (w/w) on a free base basis of ruxolitinib, or a pharmaceutically acceptable salt thereof, wherein said patient achieves a reduction in the itch Numerical Rating Scale score from baseline.

The present disclosure further provides a method of reducing itch in a human patient with atopic dermatitis, comprising administering to the skin of said human patient in need thereof, a cream formulation two times per day, wherein said cream formulation comprises 1.5% (w/w) on a free base basis of ruxolitinib phosphate, wherein said patient achieves a reduction in the itch Numerical Rating Scale score from baseline.

The present disclosure further provides a method of reducing itch in a human patient with atopic dermatitis, comprising administering to the skin of said human patient in need thereof, a cream formulation two times per day, wherein said cream formulation comprises 0.75% (w/w) on a free base basis of ruxolitinib phosphate, wherein said patient achieves a reduction in the itch Numerical Rating Scale score from baseline.

In some embodiments, the method provides prompt reduction in itch in the patient.

The present disclosure further provides a method of treating atopic dermatitis in a human patient, comprising administering to the skin of said human patient in need thereof, a cream formulation two times per day, wherein said cream formulation comprises 0.75% (w/w) or 1.5% (w/w) on a free base basis of ruxolitinib, or a pharmaceutically acceptable salt thereof.

The present disclosure further provides methods of treating atopic dermatitis in a human patient, comprising administering to the skin of said human patient in need thereof, a cream formulation two times per day, wherein said cream formulation comprises 1.5% (w/w) on a free base basis of ruxolitinib, or a pharmaceutically acceptable salt thereof.

The present disclosure further provides methods of treating atopic dermatitis in a human patient, comprising administering to the skin of said human patient in need thereof, a cream formulation two times per day, wherein said cream formulation comprises 1.5% (w/w) on a free base basis of ruxolitinib phosphate.

The present disclosure further provides a method of treating atopic dermatitis in a human patient, comprising administering to the skin of said human patient in need thereof, a cream formulation two times per day, wherein said cream formulation comprises 0.75% (w/w) on a free base basis of ruxolitinib, or a pharmaceutically acceptable salt thereof.

The present disclosure further provides a method of treating atopic dermatitis in a human patient, comprising administering to the skin of said human patient in need thereof, a cream formulation two times per day, wherein said cream formulation comprises 0.75% (w/w) on a free base basis of ruxolitinib phosphate.

In some embodiments, the ruxolitinib, or a pharmaceutically acceptable salt thereof, is ruxolitinib phosphate.

In some embodiments, the patient achieves Investigator's Global Assessment score of 0 or 1 with an improvement of at least 2 points from baseline.

In some embodiments, the patient achieves a 75% improvement in Eczema Area and Severity Index score from baseline.

The present disclosure further provides a method of treating mild to moderate atopic dermatitis in a human patient comprising administering to the skin of said human patient in need thereof, a topical formulation two times per day, wherein said topical formulation comprises 0.75% (w/w) or 1.5% (w/w) on a free base basis of ruxolitinib, or a pharmaceutically acceptable salt thereof.

The present disclosure further provides a method of treating mild to moderate atopic dermatitis in a human patient comprising administering to the skin of said human patient in need thereof, a topical formulation two times per day, wherein said topical formulation comprises 0.75% (w/w) on a free base basis of ruxolitinib, or a pharmaceutically acceptable salt thereof.

The present disclosure also provides a method of treating mild to moderate atopic dermatitis in a human patient comprising administering to the skin of said human patient in need thereof, a topical formulation two times per day, wherein said topical formulation comprises 1.5% (w/w) on a free base basis of ruxolitinib, or a pharmaceutically acceptable salt thereof.

The present disclosure further provides a method of treating mild to moderate atopic dermatitis in a human patient comprising administering to the skin of said human patient in need thereof, a topical formulation two times per day, wherein said topical formulation comprises 0.75% (w/w) on a free base basis of ruxolitinib phosphate.

The present disclosure also provides a method of treating mild to moderate atopic dermatitis in a human patient comprising administering to the skin of said human patient in need thereof, a topical formulation two times per day, wherein said topical formulation comprises 1.5% (w/w) on a free base basis of ruxolitinib phosphate.

The present disclosure further provides a method of treating mild to moderate atopic dermatitis in a human patient comprising administering to the skin of said human patient in need thereof, a cream formulation two times per day, wherein said cream formulation comprises 0.75% (w/w) or 1.5% (w/w) on a free base basis of ruxolitinib, or a pharmaceutically acceptable salt thereof.

The present disclosure further provides a method of treating mild to moderate atopic dermatitis in a human patient comprising administering to the skin of said human patient in need thereof, a cream formulation two times per day, wherein said cream formulation comprises 0.75% (w/w) on a free base basis of ruxolitinib, or a pharmaceutically acceptable salt thereof.

The present disclosure also provides a method of treating mild to moderate atopic dermatitis in a human patient comprising administering to the skin of said human patient in need thereof, a cream formulation two times per day, wherein said cream formulation comprises 1.5% (w/w) on a free base basis of ruxolitinib, or a pharmaceutically acceptable salt thereof.

The present disclosure further provides a method of treating mild to moderate atopic dermatitis in a human patient comprising administering to the skin of said human patient in need thereof, a cream formulation two times per day, wherein said cream formulation comprises 0.75% (w/w) on a free base basis of ruxolitinib phosphate.

The present disclosure also provides a method of treating mild to moderate atopic dermatitis in a human patient comprising administering to the skin of said human patient in need thereof, a cream formulation two times per day, wherein said cream formulation comprises 1.5% (w/w) on a free base basis of ruxolitinib phosphate.

The present disclosure further provides a method of treating moderate atopic dermatitis in a human patient comprising administering to the skin of said human patient in need thereof, a topical formulation two times per day, wherein said topical formulation comprises 0.75% (w/w) or 1.5% (w/w) on a free base basis of ruxolitinib, or a pharmaceutically acceptable salt thereof.

The present disclosure further provides a method of treating moderate atopic dermatitis in a human patient comprising administering to the skin of said human patient in need thereof, a topical formulation two times per day, wherein said topical formulation comprises 0.75% (w/w) on a free base basis of ruxolitinib, or a pharmaceutically acceptable salt thereof.

The present disclosure also provides a method of treating moderate atopic dermatitis in a human patient comprising administering to the skin of said human patient in need thereof, a topical formulation two times per day, wherein said topical formulation comprises 1.5% (w/w) on a free base basis of ruxolitinib, or a pharmaceutically acceptable salt thereof.

The present disclosure further provides a method of treating moderate atopic dermatitis in a human patient comprising administering to the skin of said human patient in need thereof, a topical formulation two times per day, wherein said topical formulation comprises 0.75% (w/w) on a free base basis of ruxolitinib phosphate.

The present disclosure also provides a method of treating moderate atopic dermatitis in a human patient comprising administering to the skin of said human patient in need thereof, a topical formulation two times per day, wherein said topical formulation comprises 1.5% (w/w) on a free base basis of ruxolitinib phosphate.

The present disclosure further provides a method of treating moderate atopic dermatitis in a human patient comprising administering to the skin of said human patient in need thereof, a cream formulation two times per day, wherein said cream formulation comprises 0.75% (w/w) or 1.5% (w/w) on a free base basis of ruxolitinib, or a pharmaceutically acceptable salt thereof.

The present disclosure further provides a method of treating moderate atopic dermatitis in a human patient comprising administering to the skin of said human patient in need thereof, a cream formulation two times per day, wherein said cream formulation comprises 0.75% (w/w) on a free base basis of ruxolitinib, or a pharmaceutically acceptable salt thereof.

The present disclosure also provides a method of treating moderate atopic dermatitis in a human patient comprising administering to the skin of said human patient in need thereof, a cream formulation two times per day, wherein said cream formulation comprises 1.5% (w/w) on a free base basis of ruxolitinib, or a pharmaceutically acceptable salt thereof.

The present disclosure further provides a method of treating moderate atopic dermatitis in a human patient comprising administering to the skin of said human patient in need thereof, a cream formulation two times per day, wherein said cream formulation comprises 0.75% (w/w) on a free base basis of ruxolitinib phosphate.

The present disclosure also provides a method of treating moderate atopic dermatitis in a human patient comprising administering to the skin of said human patient in need thereof, a cream formulation two times per day, wherein said cream formulation comprises 1.5% (w/w) on a free base basis of ruxolitinib phosphate.

The present disclosure also provides a method of treating moderate to severe atopic dermatitis in a human patient comprising administering to the skin of said human patient in need thereof, a topical formulation two times per day, wherein said topical formulation comprises 0.75% (w/w) or 1.5% (w/w) on a free base basis of ruxolitinib, or a pharmaceutically acceptable salt thereof.

The present disclosure further provides a method of treating moderate to severe atopic dermatitis in a human patient comprising administering to the skin of said human patient in need thereof, a topical formulation two times per day, wherein said topical formulation comprises 0.75% (w/w) on a free base basis of ruxolitinib, or a pharmaceutically acceptable salt thereof.

The present disclosure also provides a method of treating moderate to severe atopic dermatitis in a human patient comprising administering to the skin of said human patient in need thereof, a topical formulation two times per day, wherein said topical formulation comprises 1.5% (w/w) on a free base basis of ruxolitinib, or a pharmaceutically acceptable salt thereof.

The present disclosure further provides a method of treating moderate to severe atopic dermatitis in a human patient comprising administering to the skin of said human patient in need thereof, a topical formulation two times per day, wherein said topical formulation comprises 0.75% (w/w) on a free base basis of ruxolitinib phosphate.

The present disclosure also provides a method of treating moderate to severe atopic dermatitis in a human patient comprising administering to the skin of said human patient in need thereof, a topical formulation two times per day, wherein said topical formulation comprises 1.5% (w/w) on a free base basis of ruxolitinib phosphate.

The present disclosure also provides a method of treating moderate to severe atopic dermatitis in a human patient comprising administering to the skin of said human patient in need thereof, a cream formulation two times per day, wherein said cream formulation comprises 0.75% (w/w) or 1.5% (w/w) on a free base basis of ruxolitinib, or a pharmaceutically acceptable salt thereof.

The present disclosure further provides a method of treating moderate to severe atopic dermatitis in a human patient comprising administering to the skin of said human patient in need thereof, a cream formulation two times per day, wherein said cream formulation comprises 0.75% (w/w) on a free base basis of ruxolitinib, or a pharmaceutically acceptable salt thereof.

The present disclosure also provides a method of treating moderate to severe atopic dermatitis in a human patient comprising administering to the skin of said human patient in need thereof, a cream formulation two times per day, wherein said cream formulation comprises 1.5% (w/w) on a free base basis of ruxolitinib, or a pharmaceutically acceptable salt thereof.

The present disclosure further provides a method of treating moderate to severe atopic dermatitis in a human patient comprising administering to the skin of said human patient in need thereof, a cream formulation two times per day, wherein said cream formulation comprises 0.75% (w/w) on a free base basis of ruxolitinib phosphate.

The present disclosure also provides a method of treating moderate to severe atopic dermatitis in a human patient comprising administering to the skin of said human patient in need thereof, a cream formulation two times per day, wherein said cream formulation comprises 1.5% (w/w) on a free base basis of ruxolitinib phosphate.

In some embodiments of the embodiments in the preceding twenty paragraphs, the patient achieves at least a 4-point reduction in itch Numerical Rating Scale score from baseline. In some embodiments of the embodiments in the preceding twenty paragraphs, the patient achieves an Investigator's Global Assessment score of 0 or 1 with an improvement of at least 2 points from baseline. In some embodiments of the embodiments in the preceding twenty paragraphs, the patient achieves a statistically significant improvement in Eczema Area and Severity Index score from baseline. In some embodiments of the embodiments in the preceding twenty paragraphs, the patient achieves a 75% improvement in Eczema Area and Severity Index score from baseline. In some embodiments of the embodiments in the preceding twenty paragraphs, the patient achieves at least a 4-point reduction in itch Numerical Rating Scale score from baseline; and the patient achieves an Investigator's Global Assessment score of 0 or 1 with an improvement of at least 2 points from baseline. In some embodiments of the embodiments in the preceding twenty paragraphs, the patient achieves at least a 4-point reduction in itch Numerical Rating Scale score from baseline; and the patient achieves a 75% improvement in Eczema Area and Severity Index score from baseline. In some embodiments of the embodiments in the preceding twenty paragraphs, the patient achieves an Investigator's Global Assessment score of 0 or 1 with an improvement of at least 2 points from baseline; and the patient achieves a 75% improvement in Eczema Area and Severity Index score from baseline. In some embodiments of the embodiments in the preceding twenty paragraphs, the patient achieves at least a 4-point reduction in itch Numerical Rating Scale score from baseline; the patient achieves an Investigator's Global Assessment score of 0 or 1 with an improvement of at least 2 points from baseline; and the patient achieves a 75% improvement in Eczema Area and Severity Index score from baseline. In some embodiments of the embodiments in the preceding twenty paragraphs, the patient achieves at least a 4-point reduction in itch Numerical Rating Scale score from baseline at week 4 of said administering. In some embodiments of the embodiments in the preceding twenty paragraphs, the patient achieves at least a 4-point reduction in itch Numerical Rating Scale score from baseline at week 8 of said administering. In some embodiments of the embodiments in the preceding twenty paragraphs, the patient achieves an Investigator's Global Assessment score of 0 or 1 with an improvement of at least 2 points from baseline at week 4 of said administering. In some embodiments of the embodiments in the preceding twenty paragraphs, the patient achieves an Investigator's Global Assessment score of 0 or 1 with an improvement of at least 2 points from baseline at week 8 of said administering. In some embodiments of the embodiments in the preceding twenty paragraphs, the patient achieves a 75% improvement in Eczema Area and Severity Index score from baseline at week 4 of said administering. In some embodiments of the embodiments in the preceding twenty paragraphs, the patient achieves a 75% improvement in Eczema Area and Severity Index score from baseline at week 8 of said administering. In some embodiments of the embodiments in the preceding twenty paragraphs, the patient achieves at least a 4-point reduction in itch Numerical Rating Scale score from baseline at week 4 of said administering; and the patient achieves an Investigator's Global Assessment score of 0 or 1 with an improvement of at least 2 points from baseline at week 4 of said administering. In some embodiments of the embodiments in the preceding twenty paragraphs, the patient achieves at least a 4-point reduction in itch Numerical Rating Scale score from baseline at week 8 of said administering; and the patient achieves an Investigator's Global Assessment score of 0 or 1 with an improvement of at least 2 points from baseline at week 8 of said administering. In some embodiments of the embodiments in the preceding twenty paragraphs, the patient achieves at least a 4-point reduction in itch Numerical Rating Scale score from baseline at week 4 of said administering; and the patient achieves a 75% improvement in Eczema Area and Severity Index score from baseline at week 4 of said administering. In some embodiments of the embodiments in the preceding twenty paragraphs, the patient achieves at least a 4-point reduction in itch Numerical Rating Scale score from baseline at week 8 of said administering; and the patient achieves a 75% improvement in Eczema Area and Severity Index score from baseline at week 8 of said administering. In some embodiments of the embodiments in the preceding twenty paragraphs, the patient achieves an Investigator's Global Assessment score of 0 or 1 with an improvement of at least 2 points from baseline at week 4 of said administering; and the patient achieves a 75% improvement in Eczema Area and Severity Index score from baseline at week 4 of said administering. In some embodiments of the embodiments in the preceding twenty paragraphs, the patient achieves an Investigator's Global Assessment score of 0 or 1 with an improvement of at least 2 points from baseline at week 8 of said administering; and the patient achieves a 75% improvement in Eczema Area and Severity Index score from baseline at week 8 of said administering. In some embodiments of the embodiments in the preceding twenty paragraphs, the patient achieves at least a 4-point reduction in itch Numerical Rating Scale score from baseline at week 4 of said administering; the patient achieves an Investigator's Global Assessment score of 0 or 1 with an improvement of at least 2 points from baseline at week 4 of said administering; and the patient achieves a 75% improvement in Eczema Area and Severity Index score from baseline at week 4 of said administering. In some embodiments of the embodiments in the preceding twenty paragraphs, the patient achieves at least a 4-point reduction in itch Numerical Rating Scale score from baseline at week 8 of said administering; the patient achieves an Investigator's Global Assessment score of 0 or 1 with an improvement of at least 2 points from baseline at week 8 of said administering; and the patient achieves a 75% improvement in Eczema Area and Severity Index score from baseline at week 8 of said administering. In some embodiments of the embodiments in the preceding twenty paragraphs, the administering is maintained for at least 4 weeks. In some embodiments of the embodiments in the preceding twenty paragraphs, the administering is maintained for at least 8 weeks.

Generally, mild to moderate, moderate, and moderate to severe atopic dermatitis is defined by FDA—i.e., in terms of Investigator's Global Assessment score at baseline (see definition of IGA supra). For example, patients with mild atopic dermatitis have an Investigator's Global Assessment score of 2 at baseline; patients with moderate atopic dermatitis have an Investigator's Global Assessment score of 3 at baseline; and patients with severe atopic dermatitis have an Investigator's Global Assessment score of 4 at baseline. Patients with mild to moderate atopic dermatitis have an Investigator's Global Assessment score of 2 to 3 at baseline, while patients with moderate to severe atopic dermatitis have an Investigator's Global Assessment score of 3 to 4 at baseline.

In some embodiments, the patient with mild to moderate atopic dermatitis has a Body Surface Area of atopic dermatitis involvement of ≥10% at baseline. In some embodiments, the patient with moderate atopic dermatitis has a Body Surface Area of atopic dermatitis involvement of ≥10% at baseline. In some embodiments, the patient with moderate to severe atopic dermatitis has a Body Surface Area of atopic dermatitis involvement of ≥10% at baseline.

In some embodiments, the patient with mild to moderate atopic dermatitis has a Body Surface Area of atopic dermatitis involvement of from 10% to 20% at baseline. In some embodiments, the patient with moderate atopic dermatitis has a Body Surface Area of atopic dermatitis involvement of from 10% to 20% at baseline. In some embodiments, the patient with moderate to severe atopic dermatitis has a Body Surface Area of atopic dermatitis involvement of from 10% to 20% at baseline.

In some embodiments, the patient with moderate atopic dermatitis has an Eczema Area and Severity Index of ≥16 at baseline. In some embodiments, the patient with moderate to severe atopic dermatitis has an Eczema Area and Severity Index of ≥16 at baseline.

In some embodiments, the patient with moderate atopic dermatitis has Investigator's Global Assessment score of 3 and a Body Surface Area of atopic dermatitis involvement of from 10% to 20% at baseline.

In some embodiments, the patient with moderate to severe atopic dermatitis has an Eczema Area and Severity Index of ≥16 at baseline, a Body Surface Area of atopic dermatitis involvement of ≥10% at baseline, and an Investigator's Global Assessment score of 3 to 4.

The present disclosure further provides methods of treating atopic dermatitis in a human patient comprising administering to the skin of said human patient in need thereof, a topical formulation two times per day, wherein the topical formulation comprises 0.75% (w/w) or 1.5% (w/w) on a free base basis of ruxolitinib, or a pharmaceutically acceptable salt thereof,
wherein said patient has:
an Eczema Area and Severity Index score of ≥16 at baseline; and
a Body Surface Area of atopic dermatitis involvement of ≥10% at baseline.

The present disclosure further provides methods of treating atopic dermatitis in a human patient comprising administering to the skin of said human patient in need thereof, a topical formulation two times per day, wherein the topical formulation comprises 0.75% (w/w) on a free base basis of ruxolitinib, or a pharmaceutically acceptable salt thereof,
wherein said patient has:
an Eczema Area and Severity Index score of ≥16 at baseline; and
a Body Surface Area of atopic dermatitis involvement of ≥10% at baseline.

The present disclosure further provides methods of treating atopic dermatitis in a human patient comprising administering to the skin of said human patient in need thereof, a topical formulation two times per day, wherein the topical formulation comprises 1.5% (w/w) on a free base basis of ruxolitinib, or a pharmaceutically acceptable salt thereof, wherein said patient has:

an Eczema Area and Severity Index score of ≥16 at baseline; and a Body Surface Area of atopic dermatitis involvement of ≥10% at baseline.

The present disclosure further provides methods of treating atopic dermatitis in a human patient comprising administering to the skin of said human patient in need thereof, a topical formulation two times per day, wherein the topical formulation comprises 0.75% (w/w) on a free base basis of ruxolitinib phosphate, wherein said patient has:

an Eczema Area and Severity Index score of ≥16 at baseline; and a Body Surface Area of atopic dermatitis involvement of ≥10% at baseline.

The present disclosure further provides methods of treating atopic dermatitis in a human patient comprising administering to the skin of said human patient in need thereof, a topical formulation two times per day, wherein the topical formulation comprises 1.5% (w/w) on a free base basis of ruxolitinib phosphate, wherein said patient has:

an Eczema Area and Severity Index score of ≥16 at baseline; and a Body Surface Area of atopic dermatitis involvement of ≥10% at baseline.

The present disclosure further provides methods of treating atopic dermatitis in a human patient comprising administering to the skin of said human patient in need thereof, a cream formulation two times per day, wherein the cream formulation comprises 0.75% (w/w) or 1.5% (w/w) on a free base basis of ruxolitinib, or a pharmaceutically acceptable salt thereof, wherein said patient has:

an Eczema Area and Severity Index score of ≥16 at baseline; and a Body Surface Area of atopic dermatitis involvement of ≥10% at baseline.

The present disclosure further provides methods of treating atopic dermatitis in a human patient comprising administering to the skin of said human patient in need thereof, a cream formulation two times per day, wherein the cream formulation comprises 0.75% (w/w) on a free base basis of ruxolitinib, or a pharmaceutically acceptable salt thereof, wherein said patient has:

an Eczema Area and Severity Index score of ≥16 at baseline; and a Body Surface Area of atopic dermatitis involvement of ≥10% at baseline.

The present disclosure further provides methods of treating atopic dermatitis in a human patient comprising administering to the skin of said human patient in need thereof, a cream formulation two times per day, wherein the cream formulation comprises 1.5% (w/w) on a free base basis of ruxolitinib, or a pharmaceutically acceptable salt thereof, wherein said patient has:

an Eczema Area and Severity Index score of ≥16 at baseline; and a Body Surface Area of atopic dermatitis involvement of ≥10% at baseline.

The present disclosure further provides methods of treating atopic dermatitis in a human patient comprising administering to the skin of said human patient in need thereof, a cream formulation two times per day, wherein the cream formulation comprises 0.75% (w/w) on a free base basis of ruxolitinib phosphate, wherein said patient has:

an Eczema Area and Severity Index score of ≥16 at baseline; and a Body Surface Area of atopic dermatitis involvement of ≥10% at baseline.

The present disclosure further provides methods of treating atopic dermatitis in a human patient comprising administering to the skin of said human patient in need thereof, a cream formulation two times per day, wherein the cream formulation comprises 1.5% (w/w) on a free base basis of ruxolitinib phosphate, wherein said patient has:

an Eczema Area and Severity Index score of ≥16 at baseline; and a Body Surface Area of atopic dermatitis involvement of ≥10% at baseline.

In some embodiments of the embodiments in the preceding ten paragraphs, the patient has an Investigator's Global Assessment score of 3 at baseline. In some embodiments of the embodiments in the preceding ten paragraphs, the patient has an Investigator's Global Assessment score of from 3 to 4 at baseline. In some embodiments of the embodiments in the preceding ten paragraphs, the patient has an itch Numerical Rating scale of score of ≥4 at baseline. In some embodiments of the embodiments in the preceding ten paragraphs, the patient: has an Investigator's Global Assessment score of 3 at baseline; and has an itch Numerical Rating scale of score of ≥4 at baseline. In some embodiments of the embodiments in the preceding ten paragraphs, the patient: has an Investigator's Global Assessment score of from 3 to 4 at baseline; and has an itch Numerical Rating scale of score of ≥4 at baseline. In some embodiments of the embodiments in the preceding ten paragraphs, the patient is aged ≥12 years. In some embodiments of the embodiments in the preceding ten paragraphs, the patient has a history of atopic dermatitis for at least 2 years. In some embodiments of the embodiments in the preceding ten paragraphs, the patient: has an Investigator's Global Assessment score of 3 at baseline; has a history of atopic dermatitis for at least 2 years; and is aged ≥12 years. In some embodiments of the embodiments in the preceding ten paragraphs, the patient: has an Investigator's Global Assessment score of from 3 to 4 at baseline; has a history of atopic dermatitis for at least 2 years; and is aged ≥12 years. In some embodiments of the embodiments in the preceding ten paragraphs, the patient: has an Investigator's Global Assessment score of 3 at baseline; has an itch Numerical Rating scale of score of ≥4 at baseline; has a history of atopic dermatitis for at least 2 years; and is aged ≥12 years. In some embodiments of the embodiments in the preceding ten paragraphs, the patient: has an Investigator's Global Assessment score of from 3 to 4 at baseline; has an itch Numerical Rating scale of score of ≥4 at baseline; has a history of atopic dermatitis for at least 2 years; and is aged ≥12 years. In some embodiments of the embodiments in the preceding ten paragraphs, the patient has one or more of the following characteristics: an Investigator's Global Assessment score of 3 at baseline; an itch Numerical Rating scale of score of ≥4 at baseline; a history of atopic dermatitis for at least 2 years; and aged ≥12 years. In some embodiments of the embodiments in the preceding ten paragraphs, the patient achieves at least a 4-point reduction in itch Numerical Rating Scale score from baseline. In some embodiments of the embodiments in the preceding ten paragraphs, the patient achieves an Investigator's Global Assessment score of 0 or 1 with an improvement of at least 2 points from baseline. In some embodiments of the embodiments in the preceding ten paragraphs, the patient achieves a statistically significant improvement in Eczema Area and Severity Index score from baseline. In some embodiments of the embodiments in the preceding ten paragraphs, the patient achieves a 75% improvement in Eczema Area and Severity Index score from baseline. In some embodiments of the embodiments in the preceding ten paragraphs, the patient achieves at least a 4-point reduction in itch Numerical Rating Scale score from baseline; and the patient achieves an Investigator's Global Assessment score of 0 or 1 with an improvement of at least 2 points from baseline. In some embodiments of the embodiments in the preceding ten paragraphs, the patient achieves at least a 4-point reduction in itch Numerical Rating Scale score from baseline; and the patient achieves a 75% improvement in Eczema Area and Severity Index score from baseline. In some embodiments of the embodiments in the preceding ten paragraphs, the patient achieves an Investigator's Global Assessment score of 0 or 1 with an improvement of at least 2 points from baseline; and the patient achieves a 75% improvement in Eczema Area and Severity Index score from baseline. In some embodiments of the embodiments in the preceding ten paragraphs, the patient achieves at least a 4-point reduction in itch Numerical Rating Scale score from baseline; the patient achieves an Investigator's Global Assessment score of 0 or 1 with an improvement of at least 2 points from baseline; and the patient achieves a 75% improvement in Eczema Area and Severity Index score from baseline. In some embodiments of the embodiments in the preceding ten paragraphs, the patient achieves at least a 4-point reduction in itch Numerical Rating Scale score from baseline at week 4 of said administering. In some embodiments of the embodiments in the preceding ten paragraphs, the patient achieves at least a 4-point reduction in itch Numerical Rating Scale score from baseline at week 8 of said administering. In some embodiments of the embodiments in the preceding ten paragraphs, the patient achieves an Investigator's Global Assessment score of 0 or 1 with an improvement of at least 2 points from baseline at week 4 of said administering. In some embodiments of the embodiments in the preceding ten paragraphs, the patient achieves an Investigator's Global Assessment score of 0 or 1 with an improvement of at least 2 points from baseline at week 8 of said administering. In some embodiments of the embodiments in the preceding ten paragraphs, the patient achieves a 75% improvement in Eczema Area and Severity Index score from baseline at week 4 of said administering. In some embodiments of the embodiments in the preceding ten paragraphs, the patient achieves a 75% improvement in Eczema Area and Severity Index score from baseline at week 8 of said administering. In some embodiments of the embodiments in the preceding ten paragraphs, the patient achieves at least a 4-point reduction in itch Numerical Rating Scale score from baseline at week 4 of said administering; and the patient achieves an Investigator's Global Assessment score of 0 or 1 with an improvement of at least 2 points from baseline at week 4 of said administering. In some embodiments of the embodiments in the preceding ten paragraphs, the patient achieves at least a 4-point reduction in itch Numerical Rating Scale score from baseline at week 8 of said administering; and the patient achieves an Investigator's Global Assessment score of 0 or 1 with an improvement of at least 2 points from baseline at week 8 of said administering. In some embodiments of the embodiments in the preceding ten paragraphs, the patient achieves at least a 4-point reduction in itch Numerical Rating Scale score from baseline at week 4 of said administering; and the patient achieves a 75% improvement in Eczema Area and Severity Index score from baseline at week 4 of said administering. In some embodiments of the embodiments in the preceding ten paragraphs, the patient achieves at least a 4-point reduction in itch Numerical Rating Scale score from baseline at week 8 of said administering; and the patient achieves a 75% improvement in Eczema Area and Severity Index score from baseline at week 8 of said administering. In some embodiments of the embodiments in the preceding ten paragraphs, the patient achieves an Investigator's Global Assessment score of 0 or 1 with an improvement of at least 2 points from baseline at week 4 of said administering; and the patient achieves a 75% improvement in Eczema Area and Severity Index score from baseline at week 4 of said administering. In some embodiments of the embodiments in the preceding ten paragraphs, the patient achieves an Investigator's Global Assessment score of 0 or 1 with an improvement of at least 2 points from baseline at week 8 of said administering; and the patient achieves a 75% improvement in Eczema Area and Severity Index score from baseline at week 8 of said administering. In some embodiments of the embodiments in the preceding ten paragraphs, the patient achieves at least a 4-point reduction in itch Numerical Rating Scale score from baseline at week 4 of said administering; the patient achieves an Investigator's Global Assessment score of 0 or 1 with an improvement of at least 2 points from baseline at week 4 of said administering; and the patient achieves a 75% improvement in Eczema Area and Severity Index score from baseline at week 4 of said administering. In some embodiments of the embodiments in the preceding ten paragraphs, the patient achieves at least a 4-point reduction in itch Numerical Rating Scale score from baseline at week 8 of said administering; the patient achieves an Investigator's Global Assessment score of 0 or 1 with an improvement of at least 2 points from baseline at week 8 of said administering; and the patient achieves a 75% improvement in Eczema Area and Severity Index score from baseline at week 8 of said administering. In some embodiments of the embodiments in the preceding ten paragraphs, the administering is maintained for at least 4 weeks. In some embodiments of the embodiments in the preceding ten paragraphs, the administering is maintained for at least 8 weeks.

In some embodiments, the topical formulation is a cream formulation. In some embodiments, the ruxolitinib or salt thereof is ruxolitinib phosphate. In some embodiments, the formulation comprises 0.75% (w/w) on a free base basis of ruxolitinib, or a pharmaceutically acceptable salt thereof. In some embodiments, the formulation comprises 1.5% (w/w) on a free base basis of ruxolitinib, or a pharmaceutically acceptable salt thereof. In some embodiments, the formulation comprises 0.75% (w/w) on a free base basis of ruxolitinib phosphate. In some embodiments, the formulation comprises 1.5% (w/w) on a free base basis of ruxolitinib phosphate.

In some embodiments, the patient achieves at least a 4 point improvement in improvement in itch Numerical Rating Scale score from baseline. In some embodiments, the patient achieves at least a 4 point improvement in improvement in itch Numerical Rating Scale score from baseline, wherein the patient has a baseline Numerical Rating Scale score of equal to or greater than 4. In some embodiments, the patient achieves at least a 4 point improvement in improvement in itch Numerical Rating Scale score from baseline after 2 weeks of said administering, wherein the patient has a baseline Numerical Rating Scale score of equal to or greater than 4. In some embodiments, the patient achieves at least a 4 point improvement in improvement in itch Numerical Rating Scale score from baseline after 4 weeks of said administering, wherein the patient has a baseline Numerical Rating Scale score of equal to or greater than 4. In some embodiments, the patient achieves at least a 4 point improvement in improvement in itch Numerical Rating Scale score from baseline after 8 weeks of said administering, wherein the patient has a baseline Numerical Rating Scale score of equal to or greater than 4.

In some embodiments, the patient:
is aged 18 to 70 years,
has been diagnosed with atopic dermatitis for at least 2 years,
has an Investigator's Global Assessment score of 2 to 3 at screening and baseline, and
has a BSA of atopic dermatitis involvement (excluding face and intertriginous areas) of 3% to 20% at baseline.

In some embodiments, the patient:
is an adolescent aged ≥12 to 17, inclusive, or a man or woman aged ≥18 years;
has history of AD for at least 2 years;
has an Investigator's Global Assessment score of 2 to 3 at baseline; and
has a % BSA of AD involvement, excluding the scalp, of 3% to 20% at baseline.

In some embodiments, the patient:
is an adolescent aged ≥12 to 17, inclusive, or a man or woman aged ≥18 years;
has history of AD for at least 2 years;
has an Investigator's Global Assessment score of 2 to 3 at baseline;
has a % BSA of AD involvement, excluding the scalp, of 3% to 20% at baseline; and
has at least 1 target lesion (which is representative of the participant's disease state and not present on the hands, feet or genitalia) that measures about 10 cm$^2$ or more at baseline.

In some embodiments, the patient is diagnosed with atopic dermatitis as defined by the Hanifin and Rajika criteria.

In some embodiments, the patient did not use topical treatments for atopic dermatitis, other than emollients, within 2 weeks of baseline.

In some embodiments, the patient did not use systemic immunosuppressive or immunomodulating drugs (e.g., oral or injectable corticosteroids, methotrexate, cyclosporine, mycophenolate mofetil, or azathioprine) within 4 weeks or 5 half-lives of baseline (whichever is longer).

In some embodiments, the patient did not use topical treatments for atopic dermatitis, other than bland emollients, within 2 weeks of baseline; and did not use systemic immunosuppressive or systemic immunomodulating drugs within 4 weeks of baseline.

In some embodiments, the patient is not administered other therapeutic agents used to treat atopic dermatitis.

In some embodiments, the patient is not administered systemic immunosuppressive or systemic immunomodulating drugs or topical treatments for atopic dermatitis, other than bland emollients.

In some embodiments, the patient:
(i) does not show evidence of active acute or chronic infections; (ii) did not use topical treatments for atopic dermatitis (other than bland emollients) within 2 weeks of baseline; (iii) did not use systemic immunosuppressive or immunomodulating drugs (e.g., oral or injectable corticosteroids, methotrexate, cyclosporine, mycophenolate mofetil, or azathioprine) within 4 weeks or 5 half-lives of baseline (whichever is longer); (iv) was not diagnosed with other dermatologic disease besides atopic dermatitis whose presence or treatments could complicate the assessment of disease; (v) a history of other diseases besides dermatologic disorders taking treatments that could complicate assessments; (vi) did not show cytopenias at screening, defined as leukocytes <3.0×10$^9$/L, neutrophils <lower limit of normal, hemoglobin <10 g/dL. Lymphocytes <0.8×109/L, platelets <100×109/L; (vii) did not have severely impaired liver function (Child-Pugh Class C) or end-stage renal disease on dialysis or at least 1 of the following: serum creatinine >1.5 mg/dL, alanine aminotransferase or aspartate aminotransferase ≥1.5× upper limit of normal; (viii) was not taking potent systemic cytochrome P450 3A4 inhibitors or fluconazole within 2 weeks or 5 half-lives, whichever is longer, before the baseline visit, other than topical agents with limited systemic availability; and/or (ix) were not administered Janus kinase inhibitors, systemic or topical.

In some embodiments, the patient:
(i) is an adolescent aged ≥12 to 17, inclusive, or a man or woman aged ≥18 years; (ii) is diagnosed with AD as defined by the Hanifin and Rajka criteria; (iii) has history of AD for at least 2 years; (iv) has an Investigator's Global Assessment score of 2 to 3 at baseline; (v) has a % BSA of AD involvement, excluding the scalp, of 3% to 20% at baseline; (vi) agreed to discontinue all agents used to treat AD during the administering; and/or (vi) has at least 1 target lesion (which is representative of the participant's disease state and not present on the hands, feet or genitalia) that measures about 10 cm$^2$ or more at baseline.

In some embodiments, the patient:
(i) does not have an unstable course of AD (spontaneously improving or rapidly deteriorating) as determined by a physician in the 4 weeks prior to baseline; (ii) does not have concurrent conditions and history of other diseases: (a) Immunocompromised (e.g., lymphoma, acquired immunodeficiency syndrome, Wiskott-Aldrich syndrome); (b) chronic or acute infection requiring treatment with systemic antibiotics, antivirals, antiparasitics, antiprotozoals, or antifungals within 2 weeks before baseline; (c) active acute bacterial, fungal, or viral skin infection (e.g., herpes simplex, herpes zoster, chicken pox) within 1 week before baseline; (d) any other concomitant skin disorder (e.g., generalized erythroderma such as Netherton syndrome), pigmentation, or extensive scarring that, in the opinion of the investigator, may interfere with the evaluation of AD lesions or compromise participant safety; (e) presence of AD lesions only on the hands or feet without prior history of involvement of other classical areas of involvement such as the face or the folds; (f) other types of eczema; (iii) does not have any serious illness or medical, physical, or psychiatric condition(s) that, in the investigator's opinion, would interfere with full participation in the study, including administration of study drug and attending required study visits; pose a significant risk to the participant; or interfere with interpretation of study data. For example: (a) clinically significant or uncontrolled cardiac disease, including unstable angina, acute myocardial infarction within 6 months from Day 1 of study drug administration, New York Heart Association Class III or IV congestive heart failure, and arrhythmia requiring therapy or uncontrolled hypertension (blood pressure >150/90 mmHg) unless approved by medical monitor/sponsor; (b) participants with a history of malignancy in the 5 years preceding enrollment into this study, except for adequately treated, nonmetastatic malignancies; (c) low hemoglobin (<10 g/dL); (d) severe renal disease on dialysis (serum creatinine >2 mg/dL); (e) current and/or liver disease history, including known hepatitis B or C, with hepatic or biliary abnormalities; (iv) does not receive any of the following treatments within the indicated washout period before baseline: (a) 5 half-lives or 12 weeks, whichever is longer—biologic agents (e.g., dupilumab); (b) 4 weeks—systemic corticosteroids or adrenocorticotropic hormone analogs, cyclosporin, methotrexate, azathioprine, or other systemic immunosuppressive or immunomodulating agents (e.g., mycophenolate or tacrolimus); (c) 2 weeks—immunizations and sedating antihistamines, unless on long-term stable regimen (nonsedating antihistamines are permitted); (d) 1 week—use of other topical treatments for AD (other than bland emollients), such as corticosteroids, calcineurin inhibitors, coal tar (shampoo), antibiotics, antibacterial cleansing body wash/soap. Diluted sodium hypochlorite "bleach" baths are allowed as long as they do not exceed 2 baths per week and their frequency remains the same throughout the study; (v) has not previously received JAK inhibitors, systemic or topical; (vi) has not had ultraviolet light therapy or prolonged exposure to natural or artificial sources of UV radiation (e.g., sunlight or tanning booth) within 2 weeks prior to baseline and/or intention to have such exposure during the study, which is thought by the investigator to potentially impact the participant's AD; (vii) does not have positive serology test results at screening for HIV antibody; (viii) does not have liver function tests with the following: AST or ALT ≥2×ULN; alkaline phosphatase and/or bilirubin >1.5×ULN (isolated bilirubin >1.5×ULN is acceptable if bilirubin is fractionated and direct bilirubin <35%); (ix) is not pregnant or lactating, or considering pregnancy; (x) does not have a history of alcoholism or drug addiction within 1 year before screening or current alcohol or drug use that, in the opinion of the investigator, will interfere with the participant's ability to comply with the administration schedule and study assessments; and/or (xi) is not currently receiving treatment or had treatment within 30 days or 5 half-lives (whichever is longer) before baseline with another investigational medication or current enrollment in another investigational drug protocol.

In some embodiments, the two administrations per day are at least 8 hours apart.

In some embodiments, the cream formulation is an oil-in-water emulsion comprising said ruxolitinib, or pharmaceutically acceptable salt thereof.

In some embodiments, the cream formulation is an oil-in-water emulsion comprising said 1.5% (w/w) on a free base basis of ruxolitinib phosphate.

In some embodiments, the cream formulation is an oil-in-water emulsion comprising said 0.75% (w/w) on a free base basis of ruxolitinib phosphate.

In some embodiments, the cream formulation has a pH from about 2.8 to about 3.9.

In some embodiments, the cream formulation has a pH from about 2.8 to about 3.6.

In some embodiments, the cream formulation is a solubilized cream.

In some embodiments, the administering of the cream formulation does not result in a statistically significant reduction in hemoglobin or platelets. In some embodiments, the administering of the cream formulation does not result in administration site burn. In some embodiments, the administering of the cream formulation does not result in administration site pruritus.

In some embodiments, the patient achieves a prompt reduction of itch.

In some embodiments, the patient achieves a statistically significant reduction of itch at day 1 (i.e., within 12 hours) of said administering. In some embodiments, the patient achieves a statistically significant reduction of itch at day 1 (i.e., within 12 hours) of said administering of the cream formulation comprising 1.5% (w/w) ruxolitinib, or a pharmaceutically acceptable salt thereof.

In some embodiments, the patient achieves a statistically significant reduction in itch Numerical Rating Scale score from baseline at day 2 of said administering compared to a patient administered placebo for the same period.

In some embodiments, the patient achieves a statistically significant reduction in itch Numerical Rating Scale score from baseline at day 1 of said administering compared to a patient administered placebo for the same period.

In some embodiments, the patient achieves at least a 1-point reduction in itch Numerical Rating Scale score from baseline at day 1 of said administering.

In some embodiments, the patient achieves at least a 2 point improvement in itch Numerical Rating Scale score from baseline at day 1 of said administering.

In some embodiments, the patient achieves at least a 1.5 point reduction in itch Numerical Rating Scale score from baseline at day 1 of said administering.

In some embodiments, the patient achieves at least a 1-point reduction in itch Numerical Rating Scale score from baseline at day 2 of said administering.

In some embodiments, the patient achieves at least a 1.5 point reduction in itch Numerical Rating Scale score from baseline at day 2 of said administering.

In some embodiments, the patient achieves at least a 2 point reduction in itch Numerical Rating Scale score from baseline at day 2 of said administering.

In some embodiments, the patient achieves at least a 2 point reduction in itch Numerical Rating Scale score from baseline at day 4 of said administering.

In some embodiments, the patient achieves at least a 1 point reduction in itch Numerical Rating Scale score by day 2 of said administering.

In some embodiments, the patient achieves at least a 1 point reduction in itch Numerical Rating Scale score within 36 hours of said administering.

In some embodiments, the patient achieves at least a 2 point reduction in itch Numerical Rating Scale score by day 6 of said administering.

In some embodiments, the patient achieves at least a 2 point reduction in itch Numerical Rating Scale score at week 1 of said administering.

In some embodiments, the patient achieves at least a 3 point reduction in itch Numerical Rating Scale score at week 3 of said administering.

In some embodiments, the patient achieves: at least a 1 point reduction in itch Numerical Rating Scale score by day 2 of said administering, at least a 2 point reduction in itch Numerical Rating Scale score by day 6 of said administering and at least a 3 point reduction in itch Numerical Rating Scale score at week 3 of said administering.

In some embodiments, the patient achieves: at least a 1 point reduction in itch Numerical Rating Scale score within 36 hours of said administering, at least a 2 point reduction in itch Numerical Rating Scale score by day 6 of said administering and at least a 3 point reduction in itch Numerical Rating Scale score at week 3 of said administering.

In some embodiments, the patient achieves: at least a 1 point reduction in itch Numerical Rating Scale score by day 2 of said administering, at least a 2 point reduction in itch Numerical Rating Scale score at week 1 of said administering, and at least a 3 point reduction in itch Numerical Rating Scale score at week 3 of said administering.

In some embodiments, the patient achieves: at least a 1 point reduction in itch Numerical Rating Scale score within 36 hours of said administering, at least a 2 point reduction in itch Numerical Rating Scale score at week 1 of said administering, and at least a 3 point reduction in itch Numerical Rating Scale score at week 3 of said administering.

A method of reducing itch in a human patient with atopic dermatitis, comprising administering to the skin of said human patient in need thereof, a cream formulation two times per day, wherein said cream formulation comprises 1.5% (w/w) on a free base basis of ruxolitinib, or a pharmaceutically acceptable salt thereof, wherein the patient achieves at least a 1 point reduction in itch Numerical Rating Scale score by day 2 of said administering.

A method of reducing itch in a human patient with atopic dermatitis, comprising administering to the skin of said human patient in need thereof, a cream formulation two times per day, wherein said cream formulation comprises 1.5% (w/w) on a free base basis of ruxolitinib, or a pharmaceutically acceptable salt thereof, wherein the patient achieves at least a 1 point reduction in itch Numerical Rating Scale score within 36 hours of said administering.

A method of reducing itch in a human patient with atopic dermatitis, comprising administering to the skin of said human patient in need thereof, a cream formulation two times per day, wherein said cream formulation comprises 1.5% (w/w) on a free base basis of ruxolitinib, or a pharmaceutically acceptable salt thereof, wherein the patient achieves at least a 2 point reduction in itch Numerical Rating Scale score by day 6 of said administering.

A method of reducing itch in a human patient with atopic dermatitis, comprising administering to the skin of said human patient in need thereof, a cream formulation two times per day, wherein said cream formulation comprises 1.5% (w/w) on a free base basis of ruxolitinib, or a pharmaceutically acceptable salt thereof, wherein the patient achieves at least a 2 point reduction in itch Numerical Rating Scale score at week 1 of said administering.

A method of reducing itch in a human patient with atopic dermatitis, comprising administering to the skin of said human patient in need thereof, a cream formulation two times per day, wherein said cream formulation comprises 1.5% (w/w) on a free base basis of ruxolitinib, or a pharmaceutically acceptable salt thereof, wherein the patient achieves at least a 3 point reduction in itch Numerical Rating Scale score at week 3 of said administering.

A method of reducing itch in a human patient with atopic dermatitis, comprising administering to the skin of said human patient in need thereof, a cream formulation two times per day, wherein said cream formulation comprises 1.5% (w/w) on a free base basis of ruxolitinib, or a pharmaceutically acceptable salt thereof, wherein the patient achieves: at least a 1 point reduction in itch Numerical Rating Scale score by day 2 of said administering, at least a 2 point reduction in itch Numerical Rating Scale score by day 6 of said administering and at least a 3 point reduction in itch Numerical Rating Scale score at week 3 of said administering.

A method of reducing itch in a human patient with atopic dermatitis, comprising administering to the skin of said human patient in need thereof, a cream formulation two times per day, wherein said cream formulation comprises 1.5% (w/w) on a free base basis of ruxolitinib, or a pharmaceutically acceptable salt thereof, wherein the patient achieves: at least a 1 point reduction in itch Numerical Rating Scale score within 36 hours of said administering, at least a 2 point reduction in itch Numerical Rating Scale score by day 6 of said administering and at least a 3 point reduction in itch Numerical Rating Scale score at week 3 of said administering.

A method of reducing itch in a human patient with atopic dermatitis, comprising administering to the skin of said human patient in need thereof, a cream formulation two times per day, wherein said cream formulation comprises 1.5% (w/w) on a free base basis of ruxolitinib, or a pharmaceutically acceptable salt thereof, wherein the patient achieves: at least a 1 point reduction in itch Numerical Rating Scale score by day 2 of said administering, at least a 2 point reduction in itch Numerical Rating Scale score at week 1 of said administering, and at least a 3 point reduction in itch Numerical Rating Scale score at week 3 of said administering.

A method of reducing itch in a human patient with atopic dermatitis, comprising administering to the skin of said human patient in need thereof, a cream formulation two times per day, wherein said cream formulation comprises 1.5% (w/w) on a free base basis of ruxolitinib, or a pharmaceutically acceptable salt thereof, wherein the patient achieves: at least a 1 point reduction in itch Numerical Rating Scale score within 36 hours of said administering, at least a 2 point reduction in itch Numerical Rating Scale score at week 1 of said administering, and at least a 3 point reduction in itch Numerical Rating Scale score at week 3 of said administering.

In some embodiments, the patient achieves a minimal clinically important difference in itch Numerical Rating Scale score at day 1 of said administering.

In some embodiments, the patient achieves a minimal clinically important difference in itch Numerical Rating Scale score at day 2 of said administering.

In some embodiments, the patient achieves a minimal clinically important difference in itch Numerical Rating Scale score at day 3 of said administering.

In some embodiments, the patient achieves a minimal clinically important difference in itch Numerical Rating Scale score at day 4 of said administering.

In some embodiments, the patient achieves a clinically relevant improvement in itch Numerical Rating Scale score at day 2 of said administering.

In some embodiments, the patient achieves a clinically relevant improvement in itch Numerical Rating Scale score at day 3 of said administering.

In some embodiments, the patient achieves a clinically relevant improvement in itch Numerical Rating Scale score at day 4 of said administering.

In some embodiments, the patient achieves a statistically significant reduction in itch Numerical Rating Scale score from baseline at week 2 of said administering compared to a patient administered placebo for the same period.

In some embodiments, the patient achieves at least a 3 point reduction in itch Numerical Rating Scale score from baseline at week 2 of said administering.

In some embodiments, the patient achieves a clinically relevant improvement in itch Numerical Rating Scale score at week 2 of said administering.

In some embodiments, the patient achieves a statistically significant reduction in itch Numerical Rating Scale score from baseline at week 4 of said administering compared to a patient administered placebo for the same period.

In some embodiments, the patient achieves at least a 3 point reduction in itch Numerical Rating Scale score from baseline at week 4 of said administering.

In some embodiments, the patient achieves a clinically relevant improvement in itch Numerical Rating Scale score at week 4 of said administering.

In some embodiments, the patient achieves a statistically significant reduction in itch Numerical Rating Scale score from baseline at week 8 of said administering compared to a patient administered placebo for the same period.

In some embodiments, the patient achieves at least a 3 point reduction in itch Numerical Rating Scale score from baseline at week 8 of said administering.

In some embodiments, the patient achieves at least a 4 point reduction in itch Numerical Rating Scale score from baseline at week 8 of said administering.

In some embodiments, the patient achieves a clinically relevant improvement in itch Numerical Rating Scale score at week 8 of said administering.

In some embodiments, the patient achieves at least a 4.5 point reduction in itch Numerical Rating Scale score from baseline at week 12 of said administering.

In some embodiments, the administering reverses the symptomatology of atopic dermatitis.

In some embodiments, the patient achieves a statistically significant improvement in Eczema Area and Severity Index score from baseline at week 4 of said administering compared to a patient administered placebo for the same period.

In some embodiments, the patient achieves a statistically significant improvement in Eczema Area and Severity Index score from baseline at week 8 of said administering compared to a patient administered placebo for the same period.

In some embodiments, the patient achieves a 75% improvement in Eczema Area and Severity Index score from baseline at week 2 of said administering.

In some embodiments, the patient achieves a 75% improvement in Eczema Area and Severity Index score from baseline at week 4 of said administering.

In some embodiments, the patient achieves a 75% improvement in Eczema Area and Severity Index score from baseline at week 8 of said administering.

In some embodiments, the patient achieves a 75% improvement in Eczema Area and Severity Index score from baseline at week 12 of said administering.

In some embodiments, the patient achieves an Investigator's Global Assessment score of 0 or 1 with an improvement of at least 2 points from baseline at 2 weeks of said administering.

In some embodiments, the patient achieves an Investigator's Global Assessment score of 0 or 1 with an improvement of at least 2 points from baseline at 4 weeks of said administering.

In some embodiments, the patient achieves an Investigator's Global Assessment score of 0 or 1 with an improvement of at least 2 points from baseline at 8 weeks of said administering.

In some embodiments, the patient achieves a clinically meaningful improvement in the PROMIS Short Form—Sleep Disturbances (8b) 24-hour recall score at Week 8.

In some embodiments, the patient achieves at least a 50% improvement in Skindex-16 overall score at week 2 of said administering.

In some embodiments, the patient achieves at least a 60% improvement in Skindex-16 overall score at week 2 of said administering.

In some embodiments, the patient achieves at least a 50% improvement in Skindex-16 overall score at week 4 of said administering.

In some embodiments, the patient achieves at least a 60% improvement in Skindex-16 overall score at week 4 of said administering.

In some embodiments, the patient achieves at least a 70% improvement in Skindex-16 overall score at week 4 of said administering.

In some embodiments, the patient achieves at least a 50% improvement in Skindex-16 overall score at week 8 of said administering.

In some embodiments, the patient achieves at least a 60% improvement in Skindex-16 overall score at week 8 of said administering.

In some embodiments, the patient achieves at least a 70% improvement in Skindex-16 overall score at week 8 of said administering.

In some embodiments, the patient is suffering from mild to moderate atopic dermatitis.

In some embodiments, the administering is maintained for at least 2 weeks.

In some embodiments, the administering is maintained for at least 4 weeks.

In some embodiments, the administering is maintained for at least 8 weeks.

In some embodiments, the administering is maintained for at least 12 weeks.

The present disclosure also provides a method of reducing itch in a human patient with atopic dermatitis, comprising administering to the skin of said human patient in need thereof, a cream formulation two times per day, wherein said cream formulation is an oil-in-water emulsion, comprising 1.5% (w/w) on a free base basis of ruxolitinib phosphate, wherein the administering is maintained for at least 8 weeks, wherein the patient achieves at least a 4 point reduction in itch Numerical Rating Scale score from baseline at week 8 of the administering.

The present disclosure further provides a method of reducing itch in a human patient with atopic dermatitis, comprising administering to the skin of said human patient in need thereof, a cream formulation two times per day, wherein said cream formulation is an oil-in-water emulsion, comprising 0.75% (w/w) on a free base basis of ruxolitinib phosphate, wherein the administering is maintained for at least 8 weeks, wherein the patient achieves at least a 4 point reduction in itch Numerical Rating Scale score from baseline at week 8 of the administering.

The present disclosure also provides a method of reducing itch in a human patient with atopic dermatitis, comprising administering to the skin of said human patient in need thereof, a cream formulation two times per day, wherein said cream formulation is an oil-in-water emulsion, comprising 1.5% (w/w) on a free base basis of ruxolitinib phosphate, wherein the administering is maintained for at least 8 weeks, wherein the patient achieves at least a 4 point reduction in itch Numerical Rating Scale score from baseline at week 8 of the administering, and wherein the patient:

is aged 18 to 70 years, has been diagnosed with atopic dermatitis for at least 2 years, has an Investigator's Global Assessment score of 2 to 3 at screening and baseline,
and
has a Body Surface Area of atopic dermatitis involvement (excluding face and intertriginous areas) of 3% to 20% at baseline.

The present disclosure further provides a method of reducing itch in a human patient with atopic dermatitis, comprising administering to the skin of said human patient in need thereof, a cream formulation two times per day, wherein said cream formulation is an oil-in-water emulsion, comprising 0.75% (w/w) or 1.5% (w/w) on a free base basis of ruxolitinib phosphate,
wherein the administering is maintained for at least 8 weeks,
wherein the patient achieves at least a 4 point reduction in itch Numerical Rating Scale score from baseline at week 8 of the administering, and
wherein the patient:
is an adolescent aged ≥12 to 17, inclusive, or a man or woman aged ≥18 years;
has history of AD for at least 2 years;
has an Investigator's Global Assessment score of 2 to 3 at baseline; and
has a % BSA of AD involvement, excluding the scalp, of 3% to 20% at baseline.

The present disclosure also provides a method of reducing itch in a human patient with atopic dermatitis, comprising administering to the skin of said human patient in need thereof, a cream formulation two times per day, wherein said cream formulation is an oil-in-water emulsion, comprising 1.5% (w/w) on a free base basis of ruxolitinib phosphate,
wherein the administering is maintained for at least 8 weeks,
wherein the patient achieves at least a 4 point reduction in itch Numerical Rating Scale score from baseline at week 8 of said administering, and
wherein the patient achieves an Investigator's Global Assessment score of 0 or 1 with an improvement of at least 2 points from baseline at 8 weeks of said administering.

The present disclosure also provides a method of reducing itch in a human patient with atopic dermatitis, comprising administering to the skin of said human patient in need thereof, a cream formulation two times per day, wherein said cream formulation is an oil-in-water emulsion, comprising 0.75% (w/w) or 1.5% (w/w) on a free base basis of ruxolitinib phosphate,
wherein the administering is maintained for at least 8 weeks,
wherein the patient achieves at least a 4 point reduction in itch Numerical Rating Scale score from baseline at week 8 of said administering, and
wherein the patient achieves an Investigator's Global Assessment score of 0 or 1 with an improvement of at least 2 points from baseline at 8 weeks of said administering.

The present disclosure further provides a method of reducing itch in a human patient with atopic dermatitis, comprising administering to the skin of said human patient in need thereof, a cream formulation two times per day, wherein said cream formulation is an oil-in-water emulsion, comprising 1.5% (w/w) on a free base basis of ruxolitinib phosphate,
wherein the administering is maintained for at least 8 weeks,
wherein the patient achieves at least a 4-point reduction in itch Numerical Rating Scale score from baseline at week 8 of said administering,
wherein the patient achieves an Investigator's Global Assessment score of 0 or 1 with an improvement of at least 2 points from baseline at 8 weeks of said administering, and
wherein the patient:
is aged 18 to 70 years,
has been diagnosed with atopic dermatitis for at least 2 years,
has an Investigator's Global Assessment score of 2 to 3 at screening and baseline,
and
has a BSA of atopic dermatitis involvement (excluding face and intertriginous areas) of 3% to 20% at baseline.

The present disclosure further provides a method of reducing itch in a human patient with atopic dermatitis, comprising administering to the skin of said human patient in need thereof, a cream formulation two times per day, wherein said cream formulation is an oil-in-water emulsion, comprising 0.75% (w/w) or 1.5% (w/w) on a free base basis of ruxolitinib phosphate,
wherein the administering is maintained for at least 8 weeks,
wherein the patient achieves at least a 4 point reduction in itch Numerical Rating Scale score from baseline at week 8 of said administering,
wherein the patient achieves an Investigator's Global Assessment score of 0 or 1 with an improvement of at least 2 points from baseline at 8 weeks of said administering, and
wherein the patient:
is an adolescent aged ≥12 to 17, inclusive, or a man or woman aged ≥18 years;
has history of AD for at least 2 years;
has an Investigator's Global Assessment score of 2 to 3 at baseline; and
has a % BSA of AD involvement, excluding the scalp, of 3% to 20% at baseline.

In another embodiment, the present disclosure provides a method of reducing itch in a human patient with atopic dermatitis, comprising administering two times a day to the skin of said human patient in need thereof, a composition comprising:
(1) 1.5% (w/w) on a free base basis of ruxolitinib phosphate, and
(2) means for effecting dose-dependent skin permeation of said ruxolitinib phosphate, wherein said patient achieves a reduction in the itch Numerical Rating Scale score from baseline.

In another embodiment, the present disclosure provides a method of reducing itch in a human patient with atopic dermatitis, comprising administering two times a day to the skin of said human patient in need thereof, a composition comprising:
(1) 0.75% (w/w) on a free base basis of ruxolitinib phosphate, and
(2) means for effecting dose-dependent skin permeation of said ruxolitinib phosphate, wherein said patient achieves a reduction in the itch Numerical Rating Scale score from baseline.

The present disclosure also provides a method of reducing itch in a human patient with atopic dermatitis, comprising administering to the skin of said human patient in need thereof, a cream formulation two times per day, wherein said cream formulation comprises 1.5% (w/w) on a free base basis of ruxolitinib, or a pharmaceutically acceptable salt thereof,
wherein said patient achieves a reduction in the itch Numerical Rating Scale score from baseline.

The present disclosure also provides a method of reducing itch in a human patient with atopic dermatitis, comprising administering to the skin of said human patient in need thereof, a cream formulation two times per day, wherein said cream formulation comprises 0.75% (w/w) on a free base basis of ruxolitinib, or a pharmaceutically acceptable salt thereof, wherein said patient achieves a reduction in the itch Numerical Rating Scale score from baseline.

The present disclosure further provides a method of treating atopic dermatitis in a human patient comprising administering to the skin of said human patient in need thereof, a cream formulation two times per day, wherein said cream formulation comprises 0.75% (w/w) or 1.5% (w/w) on a free base basis of ruxolitinib, or a pharmaceutically acceptable salt thereof;

wherein said patient has one or more characteristics selected from the group consisting of:

an Eczema Area and Severity Index score of ≥16 at baseline;

a Body Surface Area of atopic dermatitis involvement of ≥10% at baseline;

an itch Numerical Rating Scale score of ≥4 at baseline; and an Investigator's Global Assessment score of at least 3 at baseline.

The present disclosure also provides a method of treating atopic dermatitis in a human patient comprising administering to the skin of said human patient in need thereof, a cream formulation two times per day, wherein said cream formulation comprises 0.75% (w/w) on a free base basis of ruxolitinib, or a pharmaceutically acceptable salt thereof;

wherein said patient has one or more characteristics selected from the group consisting of:

an Eczema Area and Severity Index score of ≥16 at baseline;

a Body Surface Area of atopic dermatitis involvement of ≥10% at baseline;

an itch Numerical Rating Scale score of ≥4 at baseline; and an Investigator's Global Assessment score of at least 3 at baseline.

The present disclosure further provides a method of treating atopic dermatitis in a human patient comprising administering to the skin of said human patient in need thereof, a cream formulation two times per day, wherein said cream formulation comprises 1.5% (w/w) on a free base basis of ruxolitinib, or a pharmaceutically acceptable salt thereof;

wherein said patient has one or more characteristics selected from the group consisting of:

an Eczema Area and Severity Index score of ≥16 at baseline;

a Body Surface Area of atopic dermatitis involvement of ≥10% at baseline;

an itch Numerical Rating Scale score of ≥4 at baseline; and an Investigator's Global Assessment score of at least 3 at baseline.

The present disclosure also provides a method of treating atopic dermatitis in a human patient comprising administering to the skin of said human patient in need thereof, a cream formulation two times per day, wherein said cream formulation comprises 0.75% (w/w) on a free base basis of ruxolitinib phosphate;

wherein said patient has one or more characteristics selected from the group consisting of:

an Eczema Area and Severity Index score of ≥16 at baseline;

a Body Surface Area of atopic dermatitis involvement of ≥10% at baseline;

an itch Numerical Rating Scale score of ≥4 at baseline; and an Investigator's Global Assessment score of at least 3 at baseline.

The present disclosure further provides a method of treating atopic dermatitis in a human patient comprising administering to the skin of said human patient in need thereof, a cream formulation two times per day, wherein said cream formulation comprises 1.5% (w/w) on a free base basis of ruxolitinib phosphate;

wherein said patient has one or more characteristics selected from the group consisting of:

an Eczema Area and Severity Index score of ≥16 at baseline;

a Body Surface Area of atopic dermatitis involvement of ≥10% at baseline;

an itch Numerical Rating Scale score of ≥4 at baseline; and an Investigator's Global Assessment score of at least 3 at baseline.

In some embodiments, the patient has one or more characteristics selected from the group consisting of:

an Eczema Area and Severity Index score of ≥16 at baseline;

a Body Surface Area of atopic dermatitis involvement of ≥10% at baseline;

an itch Numerical Rating Scale score of ≥4 at baseline;

an Investigator's Global Assessment score of ≥3 at baseline;

an age between 12 to 85 years; and a history of atopic dermatitis for at least 2 years.

In some embodiments, the patient has one or more characteristics selected from the group consisting of:

an Eczema Area and Severity Index score of ≥16 at baseline;

a Body Surface Area of atopic dermatitis involvement of ≥10% at baseline; and an Investigator's Global Assessment score of 3 at baseline.

In some embodiments, the patient has an Eczema Area and Severity Index score of ≥16 at baseline.

In some embodiments, the patient has a Body Surface Area of atopic dermatitis involvement of ≥10% at baseline.

In some embodiments, the patient has a Body Surface Area of atopic dermatitis involvement of from 10% to 20% at baseline.

In some embodiments, the patient has an itch Numerical Rating Scale score of ≥4 at baseline.

In some embodiments, the patient has an Investigator's Global Assessment score of 3 at baseline.

In some embodiments, the patient is suffering from moderate atopic dermatitis.

In some embodiments, the patient is suffering from moderate to severe atopic dermatitis.

In some embodiments, the patient has an Eczema Area and Severity Index of ≥16 at baseline and a Body Surface Area of atopic dermatitis involvement of ≥10% at baseline. In some embodiments of the embodiments of this paragraph, the Body Surface Area of atopic dermatitis involvement is alternatively from 10% to 20% at baseline.

In some embodiments, the patient has an Eczema Area and Severity Index score of ≥16 at baseline, a Body Surface Area of atopic dermatitis involvement of ≥10% at baseline, and an itch Numerical Rating Scale score of ≥4 at baseline. In some embodiments of the embodiments of this paragraph, the Body Surface Area of atopic dermatitis involvement is alternatively from 10% to 20% at baseline.

In some embodiments, the patient, who has an Eczema Area and Severity Index score of ≥16 at baseline and a Body Surface Area of atopic dermatitis involvement of ≥10% at baseline, achieves a 75% improvement in Eczema Area and Severity Index score from baseline at week 2 of said administering. In some embodiments of the embodiments of this paragraph, the Body Surface Area of atopic dermatitis involvement is alternatively from 10% to 20% at baseline.

In some embodiments, the patient, who has an Eczema Area and Severity Index score of ≥16 at baseline and a Body Surface Area of atopic dermatitis involvement of ≥10% at baseline, achieves a 75% improvement in Eczema Area and Severity Index score from baseline at week 4 of said administering. In some embodiments of the embodiments of this paragraph, the Body Surface Area of atopic dermatitis involvement is alternatively from 10% to 20% at baseline.

In some embodiments, the patient, who has an Eczema Area and Severity Index score of ≥16 at baseline and a Body Surface Area of atopic dermatitis involvement of ≥10% at baseline, achieves a 75% improvement in Eczema Area and Severity Index score from baseline at week 8 of said administering. In some embodiments of the embodiments of this paragraph, the Body Surface Area of atopic dermatitis involvement is alternatively from 10% to 20% at baseline.

In some embodiments, the patient who has an Eczema Area and Severity Index score of ≥16 at baseline and a Body Surface Area of atopic dermatitis involvement of ≥10% at baseline, achieves an Investigator's Global Assessment score of 0 or 1 with an improvement of at least 2 points from baseline at 2 weeks of said administering. In some embodiments of the embodiments of this paragraph, the Body Surface Area of atopic dermatitis involvement is alternatively from 10% to 20% at baseline.

In some embodiments, the patient, who has an Eczema Area and Severity Index score of ≥16 at baseline and a Body Surface Area of atopic dermatitis involvement of ≥10% at baseline, achieves an Investigator's Global Assessment score of 0 or 1 with an improvement of at least 2 points from baseline at 4 weeks of said administering. In some embodiments of the embodiments of this paragraph, the Body Surface Area of atopic dermatitis involvement is alternatively from 10% to 20% at baseline.

In some embodiments, the patient, who has an Eczema Area and Severity Index score of ≥16 at baseline and a Body Surface Area of atopic dermatitis involvement of ≥10% at baseline, achieves an Investigator's Global Assessment score of 0 or 1 with an improvement of at least 2 points from baseline at 8 weeks of said administering. In some embodiments of the embodiments of this paragraph, the Body Surface Area of atopic dermatitis involvement is alternatively from 10% to 20% at baseline.

In some embodiments, the patient has an Eczema Area and Severity Index score of ≥16 at baseline and a Body Surface Area of atopic dermatitis involvement of ≥10% at baseline, achieves at least a 4-point reduction in itch Numerical Rating Scale score from baseline at week 2 of said administering. In some embodiments of the embodiments of this paragraph, the Body Surface Area of atopic dermatitis involvement is alternatively from 10% to 20% at baseline.

In some embodiments, the patient has an Eczema Area and Severity Index score of ≥16 at baseline; a Body Surface Area of atopic dermatitis involvement of ≥10% at baseline, achieves at least a 4-point reduction in itch Numerical Rating Scale score from baseline at week 4 of said administering. In some embodiments of the embodiments of this paragraph, the Body Surface Area of atopic dermatitis involvement is alternatively from 10% to 20% at baseline.

In some embodiments, the patient, who has an Eczema Area and Severity Index score of ≥16 at baseline and a Body Surface Area of atopic dermatitis involvement of ≥10% at baseline, achieves at least a 4-point reduction in itch Numerical Rating Scale score from baseline at week 8 of said administering. In some embodiments of the embodiments of this paragraph, the Body Surface Area of atopic dermatitis involvement is alternatively from 10% to 20% at baseline.

In some embodiments, the patient, who has an Eczema Area and Severity Index score of ≥16 at baseline, a Body Surface Area of atopic dermatitis involvement of ≥10% at baseline, and an itch Numerical Rating Scale score of ≥4 at baseline, achieves at least a 4 point reduction in itch Numerical Rating Scale score from baseline at week 2 of said administering. In some embodiments of the embodiments of this paragraph, the Body Surface Area of atopic dermatitis involvement is alternatively from 10% to 20% at baseline.

In some embodiments, the patient, who has an Eczema Area and Severity Index score of ≥16 at baseline, a Body Surface Area of atopic dermatitis involvement of ≥10% at baseline, and an itch Numerical Rating Scale score of ≥4 at baseline, achieves at least a 4 point reduction in itch Numerical Rating Scale score from baseline at week 4 of said administering. In some embodiments of the embodiments of this paragraph, the Body Surface Area of atopic dermatitis involvement is alternatively from 10% to 20% at baseline.

In some embodiments, the patient, who has an Eczema Area and Severity Index score of ≥16 at baseline, a Body Surface Area of atopic dermatitis involvement of ≥10% at baseline, and an itch Numerical Rating Scale score of ≥4 at baseline, achieves at least a 4 point reduction in itch Numerical Rating Scale score from baseline at week 8 of said administering. In some embodiments of the embodiments of this paragraph, the Body Surface Area of atopic dermatitis involvement is alternatively from 10% to 20% at baseline.

In some embodiments, the patient has an Eczema Area and Severity Index score of ≥16 at baseline, a Body Surface Area of atopic dermatitis involvement of ≥10% at baseline, and an Investigator's Global Assessment score of ≥3 at screening and baseline visits. In some embodiments of the embodiments of this paragraph, the Body Surface Area of atopic dermatitis involvement is alternatively from 10% to 20% at baseline.

In some embodiments, the patient has an Eczema Area and Severity Index score of ≥16 at baseline, a Body Surface Area of atopic dermatitis involvement of ≥10% at baseline, and an Investigator's Global Assessment score of 3 at screening and baseline visits. In some embodiments of the embodiments of this paragraph, the Body Surface Area of atopic dermatitis involvement is alternatively from 10% to 20% at baseline.

In some embodiments, the patient has characteristics comprising: an Eczema Area and Severity Index score of ≥16 at baseline; a Body Surface Area of atopic dermatitis involvement of ≥10% at baseline; an age between 12 to 85 years; and a history of atopic dermatitis for at least 2 years. In some embodiments, the characteristics further comprise an Investigator's Global Assessment score of ≥3 at screening and baseline visits. In some embodiments, the characteristics further comprise an Investigator's Global Assessment score of 3 at screening and baseline visits. In some embodiments, the characteristics further comprise an itch Numerical Rating Scale score of ≥4 at baseline. In some embodiments of the embodiments of this paragraph, the Body Surface Area of atopic dermatitis involvement is alternatively from 10% to 20% at baseline.

The present disclosure further provides methods of treating atopic dermatitis in a human patient comprising administering to the skin of said human patient in need thereof, a cream formulation two times per day, wherein said cream formulation comprises 0.75% (w/w) on a free base basis of ruxolitinib phosphate, wherein the administering is maintained for at least 8 weeks, wherein the patient achieves at least a 4-point reduction in itch Numerical Rating Scale score from baseline at week 8 of said administering, wherein the patient achieves an Investigator's Global Assessment score of 0 or 1 with an improvement of at least 2 points from baseline at 8 weeks of said administering, and wherein said patient has one or more characteristics selected from the group consisting of:

an Eczema Area and Severity Index score of ≥16 at baseline;

a Body Surface Area of atopic dermatitis involvement of ≥10% at baseline;

an itch Numerical Rating Scale score of ≥4 at baseline;

an Investigator's Global Assessment score of at least 3 at baseline;

aged ≥12 years; and a history of atopic dermatitis for at least 2 years.

The present disclosure further provides methods of treating atopic dermatitis in a human patient comprising administering to the skin of said human patient in need thereof, a cream formulation two times per day, wherein said cream formulation comprises 0.75% (w/w) on a free base basis of ruxolitinib phosphate, wherein the administering is maintained for at least 8 weeks, wherein the patient achieves at least a 4-point reduction in itch Numerical Rating Scale score from baseline at week 8 of said administering, wherein the patient achieves an Investigator's Global Assessment score of 0 or 1 with an improvement of at least 2 points from baseline at 8 weeks of said administering, and wherein said patient has characteristics comprising:

an Eczema Area and Severity Index score of ≥16 at baseline;

a Body Surface Area of atopic dermatitis involvement of ≥10% at baseline;

aged ≥12 years; and a history of atopic dermatitis for at least 2 years.

The present disclosure further provides methods of treating atopic dermatitis in a human patient comprising administering to the skin of said human patient in need thereof, a cream formulation two times per day, wherein said cream formulation comprises 0.75% (w/w) on a free base basis of ruxolitinib phosphate, wherein the administering is maintained for at least 8 weeks, wherein the patient achieves at least a 4-point reduction in itch Numerical Rating Scale score from baseline at week 8 of said administering, wherein the patient achieves an Investigator's Global Assessment score of 0 or 1 with an improvement of at least 2 points from baseline at 8 weeks of said administering, and wherein said patient has characteristics comprising:

an Eczema Area and Severity Index score of ≥16 at baseline;

a Body Surface Area of atopic dermatitis involvement of ≥10% at baseline;

an itch Numerical Rating Scale score of ≥4 at baseline;

aged ≥12 years; and a history of atopic dermatitis for at least 2 years.

The present disclosure further provides methods of treating atopic dermatitis in a human patient comprising administering to the skin of said human patient in need thereof, a cream formulation two times per day, wherein said cream formulation comprises 0.75% (w/w) on a free base basis of ruxolitinib phosphate, wherein the administering is maintained for at least 8 weeks, wherein the patient achieves at least a 4-point reduction in itch Numerical Rating Scale score from baseline at week 8 of said administering, wherein the patient achieves an Investigator's Global Assessment score of 0 or 1 with an improvement of at least 2 points from baseline at 8 weeks of said administering, and wherein said patient has:

an Eczema Area and Severity Index score of ≥16 at baseline;

a Body Surface Area of atopic dermatitis involvement of ≥10% at baseline;

an itch Numerical Rating Scale score of ≥4 at baseline;

an Investigator's Global Assessment score of at least 3 at baseline;

aged ≥12 years; and a history of atopic dermatitis for at least 2 years.

The present disclosure further provides methods of treating atopic dermatitis in a human patient comprising administering to the skin of said human patient in need thereof, a cream formulation two times per day, wherein said cream formulation comprises 0.75% (w/w) on a free base basis of ruxolitinib phosphate, wherein the administering is maintained for at least 8 weeks, wherein the patient achieves at least a 4-point reduction in itch Numerical Rating Scale score from baseline at week 8 of said administering, wherein the patient achieves an Investigator's Global Assessment score of 0 or 1 with an improvement of at least 2 points from baseline at 8 weeks of said administering, and wherein said patient has:

an Eczema Area and Severity Index score of ≥16 at baseline;

a Body Surface Area of atopic dermatitis involvement of ≥10% at baseline;

an itch Numerical Rating Scale score of ≥4 at baseline;

an Investigator's Global Assessment score of 3 at screening and baseline visits;

aged ≥12 years; and a history of atopic dermatitis for at least 2 years.

In another embodiment, the present disclosure provides a method of treating atopic dermatitis in a human patient with atopic dermatitis, comprising administering two times a day to the skin of said human patient in need thereof, a composition comprising:

(1) 0.75% (w/w) on a free base basis of ruxolitinib phosphate, and (2) means for effecting dose-dependent skin permeation of said ruxolitinib phosphate, wherein said patient achieves IGA treatment success.

In another embodiment, the present disclosure provides a method of treating atopic dermatitis in a human patient with atopic dermatitis, comprising administering two times a day to the skin of said human patient in need thereof, a composition comprising:

(1) 0.75% (w/w) on a free base basis of ruxolitinib phosphate, and (2) means for effecting dose-dependent skin permeation of said ruxolitinib phosphate, wherein said patient achieves EASI-75.

In another embodiment, the present disclosure provides a method of treating atopic dermatitis in a human patient with atopic dermatitis, comprising administering two times a day to the skin of said human patient in need thereof, a composition comprising:

(1) 0.75% (w/w) on a free base basis of ruxolitinib phosphate, and (2) means for effecting dose-dependent skin permeation of said ruxolitinib phosphate, wherein said patient achieves a reduction in the itch Numerical Rating Scale score from baseline.

In another embodiment, the present disclosure provides a method of treating atopic dermatitis in a human patient with atopic dermatitis, comprising administering two times a day to the skin of said human patient in need thereof, a composition comprising:

(1) 0.75% (w/w) on a free base basis of ruxolitinib phosphate, and (2) means for effecting dose-dependent skin permeation of said ruxolitinib phosphate, wherein said patient achieves at least a 4-point improvement in improvement in itch Numerical Rating Scale score from baseline.

The present disclosure further provides methods of treating atopic dermatitis in a human patient comprising administering to the skin of said human patient in need thereof, a cream formulation two times per day, wherein said cream formulation comprises 1.5% (w/w) on a free base basis of ruxolitinib phosphate, wherein the administering is maintained for at least 8 weeks, wherein the patient achieves at least a 4 point reduction in itch Numerical Rating Scale score from baseline at week 8 of said administering, wherein the patient achieves an Investigator's Global Assessment score of 0 or 1 with an improvement of at least 2 points from baseline at 8 weeks of said administering, and wherein said patient has one or more characteristics selected from the group consisting of:

an Eczema Area and Severity Index score of ≥16 at baseline;

a Body Surface Area of atopic dermatitis involvement of ≥10% at baseline;

an itch Numerical Rating Scale score of ≥4 at baseline;

an Investigator's Global Assessment score of ≥3 at screening and baseline visits;

aged ≥12 years; and a history of atopic dermatitis for at least 2 years.

The present disclosure further provides methods of treating atopic dermatitis in a human patient comprising administering to the skin of said human patient in need thereof, a cream formulation two times per day, wherein said cream formulation comprises 1.5% (w/w) on a free base basis of ruxolitinib phosphate, wherein the administering is maintained for at least 8 weeks, wherein the patient achieves at least a 4-point reduction in itch Numerical Rating Scale score from baseline at week 8 of said administering, wherein the patient achieves an Investigator's Global Assessment score of 0 or 1 with an improvement of at least 2 points from baseline at 8 weeks of said administering, and wherein said patient has characteristics comprising:

an Eczema Area and Severity Index score of ≥16 at baseline;

a Body Surface Area of atopic dermatitis involvement of ≥10% at baseline;

aged ≥12 years; and a history of atopic dermatitis for at least 2 years.

The present disclosure further provides methods of treating atopic dermatitis in a human patient comprising administering to the skin of said human patient in need thereof, a cream formulation two times per day, wherein said cream formulation comprises or 1.5% (w/w) on a free base basis of ruxolitinib phosphate, wherein the administering is maintained for at least 8 weeks, wherein the patient achieves at least a 4-point reduction in itch Numerical Rating Scale score from baseline at week 8 of said administering, wherein the patient achieves an Investigator's Global Assessment score of 0 or 1 with an improvement of at least 2 points from baseline at 8 weeks of said administering, and wherein said patient has characteristics comprising:

an Eczema Area and Severity Index score of ≥16 at baseline;

a Body Surface Area of atopic dermatitis involvement of ≥10% at baseline;

an itch Numerical Rating Scale score of ≥4 at baseline;

aged ≥12 years; and a history of atopic dermatitis for at least 2 years.

The present disclosure further provides methods of treating atopic dermatitis in a human patient comprising administering to the skin of said human patient in need thereof, a cream formulation two times per day, wherein said cream formulation comprises 1.5% (w/w) on a free base basis of ruxolitinib phosphate, wherein the administering is maintained for at least 8 weeks, wherein the patient achieves at least a 4-point reduction in itch Numerical Rating Scale score from baseline at week 8 of said administering, wherein the patient achieves an Investigator's Global Assessment score of 0 or 1 with an improvement of at least 2 points from baseline at 8 weeks of said administering, and wherein said patient has:

an Eczema Area and Severity Index score of ≥16 at baseline;

a Body Surface Area of atopic dermatitis involvement of ≥10% at baseline;

an itch Numerical Rating Scale score of ≥4 at baseline;

an Investigator's Global Assessment score of at least 3 at screening and baseline visits;

aged ≥12 years; and a history of atopic dermatitis for at least 2 years.

The present disclosure further provides methods of treating atopic dermatitis in a human patient comprising administering to the skin of said human patient in need thereof, a cream formulation two times per day, wherein said cream formulation comprises 1.5% (w/w) on a free base basis of ruxolitinib phosphate, wherein the administering is maintained for at least 8 weeks, wherein the patient achieves at least a 4-point reduction in itch Numerical Rating Scale score from baseline at week 8 of said administering, wherein the patient achieves an Investigator's Global Assessment score of 0 or 1 with an improvement of at least 2 points from baseline at 8 weeks of said administering, and wherein said patient has:
an Eczema Area and Severity Index score of ≥16 at baseline;
a Body Surface Area of atopic dermatitis involvement of ≥10% at baseline;
an itch Numerical Rating Scale score of ≥4 at baseline;
an Investigator's Global Assessment score of 3 at screening and baseline visits;
aged ≥12 years; and
a history of atopic dermatitis for at least 2 years.

In another embodiment, the present disclosure provides a method of treating atopic dermatitis in a human patient with atopic dermatitis, comprising administering two times a day to the skin of said human patient in need thereof, a composition comprising:
(1) 1.5% (w/w) on a free base basis of ruxolitinib phosphate, and
(2) means for effecting dose-dependent skin permeation of said ruxolitinib phosphate, wherein said patient achieves IGA treatment success.

In another embodiment, the present disclosure provides a method of treating atopic dermatitis in a human patient with atopic dermatitis, comprising administering two times a day to the skin of said human patient in need thereof, a composition comprising:
(1) 1.5% (w/w) on a free base basis of ruxolitinib phosphate, and
(2) means for effecting dose-dependent skin permeation of said ruxolitinib phosphate, wherein said patient achieves EASI-75.

In another embodiment, the present disclosure provides a method of treating atopic dermatitis in a human patient with atopic dermatitis, comprising administering two times a day to the skin of said human patient in need thereof, a composition comprising:
(1) 1.5% (w/w) on a free base basis of ruxolitinib phosphate, and
(2) means for effecting dose-dependent skin permeation of said ruxolitinib phosphate, wherein said patient achieves a reduction in the itch Numerical Rating Scale score from baseline.

In another embodiment, the present disclosure provides a method of treating atopic dermatitis in a human patient with atopic dermatitis, comprising administering two times a day to the skin of said human patient in need thereof, a composition comprising:
(1) 1.5% (w/w) on a free base basis of ruxolitinib phosphate, and
(2) means for effecting dose-dependent skin permeation of said ruxolitinib phosphate, wherein said patient achieves at least a 4-point improvement in improvement in itch Numerical Rating Scale score from baseline.

Definitions

As used herein, "ruxolitinib phosphate" means the phosphoric acid salt of ruxolitinib, wherein the ruxolitinib and phosphoric acid are in a 1:1 ratio.

In some embodiments, "cream" means an emulsion, semi-solid dosage form for application to the skin.

When the methods refer to "at day 2", "at week 4", "at week 8" "at week 12", "within 36 hours", or "within 12 hours" of the administering, this refers to the time period following the first dose of the cream formulation wherein there is no interruption in the administration. For example, if the method refers to a reduction in itch NRS score from baseline at week 8 for a patient administered the cream formulation BID, this means the itch NRS score was assessed after 8 weeks of BID administration of the cream formulation following the first dose of the cream formulation with no days being skipped. In terms of itch NRS, because the ruxolitinib cream or vehicle is applied in the morning and itch NRS is measured in the evening (see Phase 2 and Phase 3 studies in the Examples), "at day 1" means after approximately 12 hours of administration, "at day 2" means after approximately 36 hours of administration, "at day 3" means after approximately 2.5 days of administration, etc.

As used herein, "prompt reduction of itch" means that there is a statistically significant reduction in itch NRS score within 12 hours (or as used herein "at day 1") of the first administration of ruxolitinib cream as compared to vehicle.

The "Hanifin and Rajika criteria" is described in Hanifin J M, Rajka G. "Diagnostic features of atopic dermatitis," *Acta Derm Venereol Suppl (Stockh)* 1980; 92:44-47, which is incorporated herein by reference in its entirety.

As used herein, "% BSA" refers to percentage of total Body Surface Area affected by AD. It can be determined to the nearest 0.1% ("handprint") using, as guides, the palm with fingers as 1% and the thumb as 0.1% for areas identified to be treated with ruxolitinib cream at baseline (excluding face and intertriginous areas; or alternatively, excluding the scalp).

As used herein, "itch NRS score" refers to itch Numerical Rating Scale. The itch NRS is a daily patient-reported measure (24-hour recall) of itch intensity. Subjects will be asked to rate the itching severity because of their AD by selecting a number from 0 (no itch) to 10 (worst imaginable itch) that best describes their worst level of itching in the past 24 hours. In a non-limiting example, patients can be issued a hand-held device (eDiary) on which to record itch severity. The patient can be instructed to complete the eDiary each night.

As used herein "EASI" refers to Eczema Area and Severity Index. The EASI scoring system is a validated disease measurement for clinical studies (Hanifin JM, et al, *Exp Dermatol* 2001; 10:11-18). The severity strata for the EASI are as follows: 0=clear; 0.1 to 1.0=almost clear; 1.1 to 7.0=mild; 7.1 to 21.0=moderate; 21.1 to 50.0=severe; 50.1 to 72.0=very severe.

As used herein, "EASI-75" refers to a ≥75% improvement in the patient's Eczema Area and Severity Index.

As used herein, "BID" refers to two times per day.

As used herein, "QD" refers to once per day.

As used herein, "statistically significant" means a p-value of <0.05 (preferably <0.001, and most preferably <0.0001).

As used herein, "IGA" refers to Investigator's Global Assessment. The grades for IGA are shown in the table below:

| Grade | Severity | Status |
|---|---|---|
| 0 | Clear | No inflammatory signs of AD |
| 1 | Almost clear | Just perceptible erythema and just perceptible papulation/infiltration |
| 2 | Mild disease | Mild erythema and mild papulation/infiltration |
| 3 | Moderate disease | Moderate erythema and moderate papulation/infiltration |

| | Grade | Severity | Status |
|---|---|---|---|
| 4 | Severe disease | | Severe erythema and severe papulation/infiltration |
| 5 | Very severe disease | | Severe erythema and severe papulation/infiltration with oozing/crusting |

As used herein, "IGA-TS" means Investigator's Global Assessment Treatment Success, which is an IGA score of 0 or 1 with ≥2 grade improvement from baseline.

As used herein, the phrase "pharmaceutically acceptable" means those compounds, materials, compositions, and/or dosage forms, which are, within the scope of sound medical judgment, suitable for use in contact with tissues of humans and animals. In some embodiments, "pharmaceutically acceptable" means approved by a regulatory agency of the Federal or a state government or listed in the U.S. Pharmacopeia or other generally recognized pharmacopeia for use in animals, and more particularly in humans.

The present invention also includes pharmaceutically acceptable salts of the compounds described herein. As used herein, "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present invention include the conventional non-toxic salts of the parent compound formed, for example, from non-toxic inorganic or organic acids. The pharmaceutically acceptable salts of the present invention can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile (MeCN) are preferred. Lists of suitable salts are found in *Remington's Pharmaceutical Sciences*, 17th ed., Mack Publishing Company, Easton, Pa., 1985, p. 1418 and *Journal of Pharmaceutical Science*, 66, 2 (1977), each of which is incorporated herein by reference in its entirety. In some embodiments, the pharmaceutically acceptable salt is a phosphoric acid salt, a sulfuric acid salt, or a maleic acid salt.

As used herein, "PROMIS" refers to Patient-Reported Outcomes Measurement Information System (PROMIS®), which is a set of widely used and accepted patient-reported outcome measurements that have been developed with strong clinical outcome assessment development methods and are psychometrically supported. The selected PROMIS Short Form—Sleep-Related Impairment (8a) and Short Form—Sleep-Disturbance (8b) questionnaires have been modified to be completed with a diary on a daily basis with a 24-hour recall: Short Form—Sleep-Related Impairment (8a) is collected in the evening, and Short Form—Sleep-Disturbance (8b) is collected in the morning during the vehicle-control period.

As used herein, "minimal clinically important difference" or "MCID" refers to a 2-3 point reduction in itch NRS versus baseline.

As used herein, "clinically relevant improvement" or "CRI" refers to a ≥4 point reduction in itch NRS versus baseline.

As used herein, the term "emulsifier component" refers, in one aspect, to a substance, or mixtures of substances that maintains an element or particle in suspension within a fluid medium. In some embodiments, the emulsifier component allows an oil phase to form an emulsion when combined with water. In some embodiments, the emulsifier component refers to one or more non-ionic surfactants.

As used herein, the term "occlusive agent component" refers to a hydrophobic agent or mixtures of hydrophobic agents that form an occlusive film on skin that reduces transepidermal water loss (TEWL) by preventing evaporation of water from the stratum corneum.

As used herein, the term "stiffening agent component" refers to a substance or mixture of substances that increases the viscosity and/or consistency of the cream or improves the rheology of the cream.

As used herein, the term "emollient component" refers to an agent that softens or soothes the skin or soothes an irritated internal surface.

As used herein, the term "stabilizing agent component" refers to a substance or mixture of substances that improves the stability of the cream and/or the compatibility of the components in the cram. In some embodiments, the stabilizing agent component prevents agglomeration of the emulsion and stabilizes the droplets in the oil-in-water emulsion.

As used herein, the term "solvent component" is a liquid substance or mixture of liquid substances capable of dissolving ruxolitinib (or its salt) or other substances in the cream. In some embodiments, the solvent component is a liquid substance or mixture of liquid substances in which ruxolitinib, or its pharmaceutically acceptable salt, has reasonable solubility. For example, solubilities of ruxolitinib (free base) or its phosphate salt (1:1 salt) are reported in Table 1. In some embodiments, a solvent is a substance or mixture thereof, in which ruxolitinib, or its pharmaceutically acceptable salt (whichever is used), has a solubility of at least about 10 mg/mL or greater, at least about 15 mg/mL or greater, or at least about 20 mg/mL or greater, when measured as described in Example 2.

As used herein, the phrase "antimicrobial preservative component" is a substance or mixtures of substances which inhibits microbial growth in the cream.

As used herein, the phrase "chelating agent component" refers to a compound or mixtures of compounds that has the ability to bind strongly with metal ions.

As used herein, "% by weight of the emulsion" means the percent concentration of the component in the emulsion is on weight/weight basis. For example, 1% w/w of component A=[(mass of component A)/(total mass of the emulsion)]×100.

As used herein, "% by weight of the emulsion on a free base basis" of ruxolitinib, or pharmaceutically acceptable salt thereof" means that the % w/w is calculated based on the weight of ruxolitinib in the total emulsion. For example, "1.5% w/w on a free base basis" of ruxolitinib phosphate means that for 100 grams of total formulation, there are 1.98 grams of ruxolitinib phosphate in the emulsion (which equates to 1.5 grams of the free base, ruxolitinib).

As used herein, the term "component" can mean one substance or a mixture of substances.

As used herein, the term "fatty acid" refers to an aliphatic acid that is saturated or unsaturated. In some embodiments, the fatty acid is in a mixture of different fatty acids. In some embodiments, the fatty acid has between about eight to about thirty carbons on average. In some embodiments, the fatty acid has about 12 to 20, 14-20, or 16-18 carbons on average. Suitable fatty acids include, but are not limited to, cetyl acid, stearic acid, lauric acid, myristic acid, erucic acid, palmitic acid, palmitoleic acid, capric acid, caprylic acid, oleic acid, linoleic acid, linolenic acid, hydroxystearic acid, 12-hydroxystearic acid, cetostearic acid, isostearic acid, sesquioleic acid, sesqui-9-octadecanoic acid, sesquiisooctadecanoic acid, behenic acid, isobehenic acid, and arachidonic acid, or mixtures thereof.

As used herein, the term "fatty alcohol" refers to an aliphatic alcohol that is saturated or unsaturated. In some embodiments, the fatty alcohol is in a mixture of different fatty alcohols. In some embodiments, the fatty alcohol has between about 12 to about 20, about 14 to about 20, or about 16 to about 18 carbons on average. Suitable fatty alcohols include, but are not limited to, stearyl alcohol, lauryl alcohol, palmityl alcohol, cetyl alcohol, capryl alcohol, caprylyl alcohol, oleyl alcohol, linolenyl alcohol, arachidonic alcohol, behenyl alcohol, isobehenyl alcohol, selachyl alcohol, chimyl alcohol, and linoleyl alcohol, or mixtures thereof.

As used herein, the term "polyalkylene glycol", employed alone or in combination with other terms, refers to a polymer containing oxyalkylene monomer units, or copolymer of different oxyalkylene monomer units, wherein the alkylene group has 2 to 6, 2 to 4, or 2 to 3 carbon atoms. As used herein, the term "oxyalkylene", employed alone or in combination with other terms, refers to a group of formula —O-alkylene-. In some embodiments, the polyalkylene glycol is polyethylene glycol.

As used herein, the term, "sorbitan fatty ester" includes products derived from sorbitan or sorbitol and fatty acids and, optionally, poly(ethylene glycol) units, including sorbitan esters and polyethoxylated sorbitan esters. In some embodiments, the sorbitan fatty ester is a polyethoxylated sorbitan ester.

As used herein, the term "sorbitan ester" refers to a compound, or mixture of compounds, derived from the esterification of sorbitol and at least one fatty acid. Fatty acids useful for deriving the sorbitan esters include, but are not limited to, those described herein. Suitable sorbitan esters include, but are not limited to, the Span™ series (available from Uniqema), which includes Span 20 (sorbitan monolaurate), 40 (sorbitan monopalmitate), 60 (sorbitan monostearate), 65 (sorbitan tristearate), 80 (sorbitan monooleate), and 85 (sorbitan trioleate). Other suitable sorbitan esters include those listed in R. C. Rowe and P. J. Shesky, Handbook of pharmaceutical excipients, (2006), 5th ed., which is incorporated herein by reference in its entirety.

As used herein, the term "polyethoxylated sorbitan ester" refers to a compound, or mixture thereof, derived from the ethoxylation of a sorbitan ester. The polyoxethylene portion of the compound can be between the fatty ester and the sorbitan moiety. As used herein, the term "sorbitan ester" refers to a compound, or mixture of compounds, derived from the esterification of sorbitol and at least one fatty acid. Fatty acids useful for deriving the polyethoyxlated sorbitan esters include, but are not limited to, those described herein. In some embodiments, the polyoxyethylene portion of the compound or mixture has about 2 to about 200 oxyethylene units. In some embodiments, the polyoxyethylene portion of the compound or mixture has about 2 to about 100 oxyethylene units. In some embodiments, the polyoxyethylene portion of the compound or mixture has about 4 to about 80 oxyethylene units. In some embodiments, the polyoxyethylene portion of the compound or mixture has about 4 to about 40 oxyethylene units. In some embodiments, the polyoxyethylene portion of the compound or mixture has about 4 to about 20 oxyethylene units. Suitable polyethoxylated sorbitan esters include, but are not limited to the Tween™ series (available from Uniqema), which includes Tween 20 (POE(20) sorbitan monolaurate), 21 (POE(4) sorbitan monolaurate), 40 (POE(20) sorbitan monopalmitate), 60 (POE(20) sorbitan monostearate), 60K (POE(20) sorbitan monostearate), 61 (POE(4) sorbitan monostearate), 65 (POE(20) sorbitan tristearate), 80 (POE(20) sorbitan monooleate), 80K (POE(20) sorbitan monooleate), 81 (POE (5) sorbitan monooleate), and 85 (POE(20) sorbitan trioleate). As used herein, the abbreviation "POE" refers to polyoxyethylene. The number following the POE abbreviation refers to the number of oxyethylene repeat units in the compound. Other suitable polyethoxylated sorbitan esters include the polyoxyethylene sorbitan fatty acid esters listed in R. C. Rowe and P. J. Shesky, Handbook of pharmaceutical excipients, (2006), 5th ed., which is incorporated herein by reference in its entirety. In some embodiments, the polyethoxylated sorbitan ester is a polysorbate. In some embodiments, the polyethoxylated sorbitan ester is polysorbate 20.

As used herein, the term "glyceryl fatty esters" refers to mono-, di- or triglycerides of fatty acids. The glyceryl fatty esters may be optionally substituted with sulfonic acid groups, or pharmaceutically acceptable salts thereof. Suitable fatty acids for deriving glycerides of fatty acids include, but are not limited to, those described herein. In some embodiments, the glyceryl fatty ester is a mono-glyceride of a fatty acid having 12 to 18 carbon atoms. In some embodiments, the glyceryl fatty ester is glyceryl stearate.

As used herein, the term "triglycerides" refers to a triglyceride of a fatty acid. In some embodiments, the triglyceride is medium chain triglycerides.

As used herein, the term "alkylene glycol" refers to a group of formula —O-alkylene-, wherein the alkylene group has 2 to 6, 2 to 4, or 2 to 3 carbon atoms. In some embodiments, the alkylene glycol is propylene glycol (1,2-propanediol).

As used herein, the term "polyethylene glycol" refers to a polymer containing ethylene glycol monomer units of formula —O—$CH_2$—$CH_2$—. Suitable polyethylene glycols may have a free hydroxyl group at each end of the polymer molecule, or may have one or more hydroxyl groups etherified with a lower alkyl, e.g., a methyl group. Also suitable are derivatives of polyethylene glycols having esterifiable carboxy groups. Polyethylene glycols useful in the present disclosure can be polymers of any chain length or molecular weight, and can include branching. In some embodiments, the average molecular weight of the polyethylene glycol is from about 200 to about 9000. In some embodiments, the average molecular weight of the polyethylene glycol is from about 200 to about 5000. In some embodiments, the average molecular weight of the polyethylene glycol is from about 200 to about 900. In some embodiments, the average molecular weight of the polyethylene glycol is about 400. Suitable polyethylene glycols include, but are not limited to polyethylene glycol-200, polyethylene glycol-300, polyethylene glycol-400, polyethylene glycol-600, and polyethylene glycol-900. The number following the dash in the name refers to the average molecular weight of the polymer.

In some embodiments, "about" means plus or minus 10% of the value.

Cream Formulations

In some embodiments, the cream formulation is an oil-in-water emulsion. In some embodiments, the cream is a solubilized cream. In some embodiments, the cream has a pH from about 2.8 to about 3.6. In the context of pH, "about" refers to ±0.3 (preferably ±0.2 or more preferably ±0.1).

In some embodiments, the cream comprises an oil-in-water emulsion, comprising 1.5% (w/w) on a free base basis of ruxolitinib phosphate.

In some embodiments, the cream is an oil-in-water emulsion as described in US 2015/0250790, which is incorporated herein by reference in its entirety. In particular, Examples 3-6 of US 2015/0250790 (and particularly Tables 3-5 and accompanying text) are incorporated herein by reference.

In some embodiments, the oil component is present in an amount of about 10% to about 40% by weight of the emulsion.

In some embodiments, the oil component is present in an amount of about 10% to about 24% by weight of the emulsion.

In some embodiments, the oil component is present in an amount of about 15% to about 24% by weight of the emulsion.

In some embodiments, the oil component is present in an amount of about 18% to about 24% by weight of the emulsion.

In some embodiments, the oil component comprises one or more substances independently selected from petrolatums, fatty alcohols, mineral oils, triglycerides, and silicone oils.

In some embodiments, the oil component comprises one or more substances independently selected from white petrolatum, cetyl alcohol, stearyl alcohol, light mineral oil, medium chain triglycerides, and dimethicone.

In some embodiments, the oil component comprises an occlusive agent component.

In some embodiments, the occlusive agent component is present in an amount of about 2% to about 15% by weight of the emulsion.

In some embodiments, the occlusive agent component is present in an amount of about 5% to about 10% by weight of the emulsion.

In some embodiments, the occlusive agent component comprises one or more substances selected from fatty acids (e.g., lanolin acid), fatty alcohols (e.g., lanolin alcohol), hydrocarbon oils & waxes (e.g., petrolatum), polyhydric alcohols (e.g., propylene glycol), silicones (e.g., dimethicone), sterols (e.g., cholesterol), vegetable or animal fat (e.g., cocoa butter), vegetable wax (e.g., Carnauba wax), and wax ester (e.g., bees wax).

In some embodiments, the occlusive agent component comprises one or more substances selected from lanolin acid fatty alcohols, lanolin alcohol, petrolatum, propylene glycol, dimethicone, cholesterol, cocoa butter, Carnauba wax, and bees wax.

In some embodiments, the occlusive agent component comprises petrolatum.

In some embodiments, the occlusive agent component comprises white petrolatum.

In some embodiments, the oil component comprises a stiffening agent component.

In some embodiments, the stiffening agent component is present in an amount of about 2% to about 8% by weight of the emulsion.

In some embodiments, the stiffening agent component is present in an amount of about 3% to about 6% by weight of the emulsion.

In some embodiments, the stiffening agent component is present in an amount of about 4% to about 7% by weight of the emulsion.

In some embodiments, the stiffening agent component comprises one or more substances independently selected from fatty alcohols.

In some embodiments, the stiffening agent component comprises one or more substances independently selected from $C_{12-20}$ fatty alcohols.

In some embodiments, the stiffening agent component comprises one or more substances independently selected from $C_{16-18}$ fatty alcohols.

In some embodiments, the stiffening agent component comprises one or more substances independently selected from cetyl alcohol and stearyl alcohol.

In some embodiments, the oil component comprises an emollient component.

In some embodiments, the emollient component is present in an amount of about 5% to about 15% by weight of the emulsion.

In some embodiments, the emollient component is present in an amount of about 7% to about 13% by weight of the emulsion.

In some embodiments, the emollient component comprises one or more substances independently selected from mineral oils and triglycerides.

In some embodiments, the emollient component comprises one or more substances independently selected from light mineral oil and medium chain triglycerides.

In some embodiments, the emollient component comprises one or more substances independently selected from light mineral oil, medium chain triglycerides, and dimethicone.

In some embodiments, the water is present in an amount of about 35% to about 65% by weight of the emulsion.

In some embodiments, the water is present in an amount of about 40% to about 60% by weight of the emulsion.

In some embodiments, the water is present in an amount of about 45% to about 55% by weight of the emulsion.

In some embodiments, the emulsifier component is present in an amount of about 1% to about 9% by weight of the emulsion.

In some embodiments, the emulsifier component is present in an amount of about 2% to about 6% by weight of the emulsion.

In some embodiments, the emulsifier component is present in an amount of about 3% to about 5% by weight of the emulsion.

In some embodiments, the emulsifier component is present in an amount of about 4% to about 7% by weight of the emulsion.

In some embodiments, the emulsion comprises an emulsifier component and a stiffening agent component, wherein the combined amount of emulsifier component and stiffening agent component is at least about 8% by weight of the emulsion.

In some embodiments, the emulsifier component comprises one or more substances independently selected from glyceryl fatty esters and sorbitan fatty esters.

In some embodiments, the emulsifier component comprises one or more substances independently selected from glyceryl stearate, and polysorbate 20.

In some embodiments, the emulsion further comprises a stabilizing agent component.

In some embodiments, the stabilizing agent component is present in an amount of about 0.05% to about 5% by weight of the emulsion.

In some embodiments, the stabilizing agent component is present in an amount of about 0.1% to about 2% by weight of the emulsion.

In some embodiments, the stabilizing agent component is present in an amount of about 0.3% to about 0.5% by weight of the emulsion.

In some embodiments, the stabilizing agent component comprises one or more substances independently selected from polysaccharides.

In some embodiments, the stabilizing agent component comprises xanthan gum.

In some embodiments, the emulsion further comprises a solvent component.

In some embodiments, the solvent component is present in an amount of about 10% to about 35% by weight of the emulsion.

In some embodiments, the solvent component is present in an amount of about 15% to about 30% by weight of the emulsion.

In some embodiments, the solvent component is present in an amount of about 20% to about 25% by weight of the emulsion.

In some embodiments, the solvent component comprises one or more substances independently selected from alkylene glycols and polyalkylene glycols.

In some embodiments, the solvent component comprises one or more substances independently selected from propylene glycol and polyethylene glycol.

In some embodiments, the emulsion comprises:
from about 35% to about 65% of water by weight of the emulsion;
from about 10% to about 40% of an oil component by weight of the emulsion;
from about 1% to about 9% of an emulsifier component by weight of the emulsion;
from about 10% to about 35% of a solvent component by weight of the emulsion;
from about 0.05% to about 5% of a stabilizing agent component by weight of the emulsion; and
from 0.5% to 1.5% of ruxolitinib, or a pharmaceutically acceptable salt thereof, by weight of the emulsion on a free base basis.

In some embodiments, the emulsion comprises:
from about 35% to about 65% of water by weight of the emulsion;
from about 10% to about 24% of an oil component by weight of the emulsion;
from about 1% to about 9% of an emulsifier component by weight of the emulsion;
from about 10% to about 35% of a solvent component by weight of the emulsion;
from about 0.05% to about 5% of a stabilizing agent component by weight of the emulsion; and
from 0.5% to 1.5% of ruxolitinib, or a pharmaceutically acceptable salt thereof, by weight of the emulsion on a free base basis.

In some embodiments, the emulsion comprises:
from about 40% to about 60% of water by weight of the emulsion;
from about 15% to about 30% of an oil component by weight of the emulsion;
from about 2% to about 6% of an emulsifier component by weight of the emulsion;
from about 15% to about 30% of a solvent component by weight of the emulsion;
from about 0.1% to about 2% of a stabilizing agent component by weight of the emulsion; and
from 0.5% to 1.5% of ruxolitinib, or a pharmaceutically acceptable salt thereof, by weight of the emulsion on a free base basis.

In some embodiments, the emulsion comprises:
from about 40% to about 60% of water by weight of the emulsion;
from about 15% to about 30% of an oil component by weight of the emulsion;
from about 2% to about 6% of an emulsifier component by weight of the emulsion;
from about 15% to about 24% of a solvent component by weight of the emulsion;
from about 0.1% to about 2% of a stabilizing agent component by weight of the emulsion; and
from 0.5% to 1.5% of ruxolitinib, or a pharmaceutically acceptable salt thereof, by weight of the emulsion on a free base basis.

In some embodiments, the emulsion comprises:
from about 45% to about 55% of water by weight of the emulsion;
from about 15% to about 24% of an oil component by weight of the emulsion;
from about 3% to about 5% of an emulsifier component by weight of the emulsion;
from about 20% to about 25% of a solvent component by weight of the emulsion;
from about 0.3% to about 0.5% of a stabilizing agent component by weight of the emulsion; and
from 0.5% to 1.5% of ruxolitinib, or a pharmaceutically acceptable salt thereof, by weight of the emulsion on a free base basis.

In some embodiments, the emulsion comprises:
from about 45% to about 55% of water by weight of the emulsion;
from about 15% to about 24% of an oil component by weight of the emulsion;
from about 4% to about 7% of an emulsifier component by weight of the emulsion;
from about 20% to about 25% of a solvent component by weight of the emulsion;
from about 0.3% to about 0.5% of a stabilizing agent component by weight of the emulsion; and
from 0.5% to 1.5% of ruxolitinib, or a pharmaceutically acceptable salt thereof, by weight of the emulsion on a free base basis.

In some embodiments:
the oil component comprises one or more substances independently selected from petrolatums, fatty alcohols, mineral oils, triglycerides, and dimethicones;
the emulsifier component comprises one or more substances independently selected from glyceryl fatty esters and sorbitan fatty esters;
the solvent component comprises one or more substances independently selected from alkylene glycols and polyalkylene glycols; and
the stabilizing agent component comprises one or more substances independently selected from polysaccharides.

In some embodiments:
the oil component comprises one or more substances independently selected from white petrolatum, cetyl alcohol, stearyl alcohol, light mineral oil, medium chain triglycerides, and dimethicone;
the emulsifier component comprises one or more substances independently selected from glyceryl stearate and polysorbate 20;
the solvent component comprises one or more substances independently selected from propylene glycol and polyethylene glycol; and
the stabilizing agent component comprises xanthan gum.

In some embodiments, the emulsion comprises:
from about 35% to about 65% of water by weight of the emulsion;
from about 2% to about 15% of an occlusive agent component by weight of the emulsion;
from about 2% to about 8% of a stiffening agent component by weight of the emulsion;
from about 5% to about 15% of an emollient component by weight of the emulsion;
from about 1% to about 9% of an emulsifier component by weight of the emulsion;
from about 0.05% to about 5% of a stabilizing agent component by weight of the emulsion;
from about 10% to about 35% of a solvent component by weight of the emulsion; and
from 0.5% to 1.5% of ruxolitinib, or a pharmaceutically acceptable salt thereof, by weight of the emulsion on a free base basis.

In some embodiments, the emulsion comprises:
from about 40% to about 60% of water by weight of the emulsion;
from about 5% to about 10% of an occlusive agent component by weight of the emulsion;
from about 2% to about 8% of a stiffening agent component by weight of the emulsion;
from about 7% to about 12% of an emollient component by weight of the emulsion;
from about 2% to about 6% of an emulsifier component by weight of the emulsion;
from about 0.1% to about 2% of a stabilizing agent by weight of the emulsion;
from about 15% to about 30% of a solvent component by weight of the emulsion; and
from 0.5% to 1.5% of ruxolitinib, or a pharmaceutically acceptable salt thereof, by weight of the emulsion on a free base basis.

In some embodiments, the emulsion comprises:
from about 45% to about 55% of water by weight of the emulsion;
from about 5% to about 10% of an occlusive agent component by weight of the emulsion;
from about 3% to about 6% of a stiffening agent component by weight of the emulsion;
from about 7% to about 13% of an emollient component by weight of the emulsion;
from about 3% to about 5% of an emulsifier component by weight of the emulsion;
from about 0.3% to about 0.5% of a stabilizing agent component by weight of the emulsion;
from about 20% to about 25% of a solvent component by weight of the emulsion; and
from 0.5% to 1.5% of ruxolitinib, or a pharmaceutically acceptable salt thereof, by weight of the emulsion on a free base basis.

In some embodiments, the emulsion comprises:
from about 45% to about 55% of water by weight of the emulsion;
from about 5% to about 10% of an occlusive agent component by weight of the emulsion;
from about 4% to about 7% of a stiffening agent component by weight of the emulsion;
from about 7% to about 13% of an emollient component by weight of the emulsion;
from about 4% to about 7% of an emulsifier component by weight of the emulsion;
from about 0.3% to about 0.5% of a stabilizing agent component by weight of the emulsion;
from about 20% to about 25% of a solvent component by weight of the emulsion; and
from 0.5% to 1.5% of ruxolitinib, or a pharmaceutically acceptable salt thereof, by weight of the emulsion on a free base basis.

In some embodiments, the emulsion comprises:
from about 45% to about 55% of water by weight of the emulsion;
about 7% of an occlusive agent component by weight of the emulsion;
from about 4.5% to about 5% of a stiffening agent component by weight of the emulsion;
about 10% of an emollient component by weight of the emulsion;
from about 4% to about 4.5% of an emulsifier component by weight of the emulsion;
about 0.4% of a stabilizing agent component by weight of the emulsion;
about 22% of a solvent component by weight of the emulsion; and
from 0.5% to 1.5% of ruxolitinib, or a pharmaceutically acceptable salt thereof, by weight of the emulsion on a free base basis.

In some embodiments, the ruxolitinib, or pharmaceutically acceptable salt thereof, is present as ruxolitinib phosphate.

In some embodiments, the emulsion comprises 1.5% of ruxolitinib, or a pharmaceutically acceptable salt thereof, by weight of the emulsion.

In some embodiments, the emulsion comprises 1.5% of ruxolitinib phosphate by weight of the emulsion.

In some embodiments, the emulsion comprises 0.75% of ruxolitinib, or a pharmaceutically acceptable salt thereof, by weight of the emulsion.

In some embodiments, the emulsion comprises 0.75% of ruxolitinib phosphate by weight of the emulsion.

In some embodiments, the combined amount of the stiffening agent component and the emulsifier component is at least about 8% by weight of the emulsion.

In some embodiments:
the occlusive agent component comprises a petrolatum;
the stiffening agent component comprises one or more substances independently selected from one or more fatty alcohols;
the emollient component comprises one or more substances independently selected from mineral oils and triglycerides;
the emulsifier component comprises one or more substances independently selected from glyceryl fatty esters and sorbitan fatty esters;
the stabilizing agent component comprises one or more substances independently selected from polysaccharides; and
the solvent component comprises one or more substances independently selected from alkylene glycols and polyalkylene glycols.

In some embodiments:
the occlusive agent component comprises white petrolatum;
the stiffening agent component comprises one or more substances independently selected from cetyl alcohol and stearyl alcohol;
the emollient component comprises one or more substances independently selected from light mineral oil, medium chain triglycerides, and dimethicone;

the emulsifier component comprises one or more substances independently selected from glyceryl stearate and polysorbate 20;

the stabilizing agent component comprises xanthan gum; and the solvent component comprises one or more substances independently selected from propylene glycol and polyethylene glycol.

In some embodiments, the emulsion further comprises an antimicrobial preservative component.

In some embodiments, the antimicrobial preservative component is present in an amount of about 0.05% to about 3% by weight of the emulsion.

In some embodiments, the antimicrobial preservative component is present in an amount of about 0.1% to about 1% by weight of the emulsion.

In some embodiments, the antimicrobial preservative component comprises one or more substances independently selected from alkyl parabens and phenoxyethanol.

In some embodiments, the antimicrobial preservative component comprises one or more substances independently selected from methyl paraben, propyl paraben, and phenoxyethanol.

In some embodiments, the emulsion further comprises a chelating agent component.

In some embodiments, the chelating agent component comprises edetate disodium.

Ruxolitinib can be prepared as described in U.S. Pat. No. 7,598,257 and U.S. Patent Publ. No. 2009/0181959, each of which is incorporated herein by reference in its entirety. The 1:1 phosphate salt of ruxolitinib can be prepared as described in U.S. Patent Publ. No. 2008/0312259, which is incorporated herein by reference in its entirety.

As will be appreciated, some components of the cream (emulsion) described herein can possess multiple functions. For example, a given substance may act as both an emulsifying agent component and a stabilizing agent. In some such cases, the function of a given component can be considered singular, even though its properties may allow multiple functionality. In some embodiments, each component of the formulation comprises a different substance or mixture of substances.

It is further appreciated that certain features of the disclosure, which are, for clarity, described in the context of separate embodiments, can also be provided in combination in a single embodiment. Conversely, various features of the disclosure which are, for brevity, described in the context of a single embodiment, can also be provided separately or in any suitable subcombination.

The following embodiments are provided:
1. A method of reducing itch in a human patient with atopic dermatitis, comprising administering to the skin of said human patient in need thereof, a cream formulation two times per day, wherein said cream formulation comprises 1.5% (w/w) on a free base basis of ruxolitinib phosphate, wherein said patient achieves a reduction in the itch Numerical Rating Scale score from baseline.
2. The method of embodiment 1, wherein said patient:
   is aged 18 to 70 years,
   has been diagnosed with atopic dermatitis for at least 2 years,
   has an IGA score of 2 to 3 at screening and baseline, and
   has a BSA of atopic dermatitis involvement (excluding face and intertriginous areas) of 3% to 20% at baseline.
3. The method of embodiment 1 or 2, wherein the patient is diagnosed with atopic dermatitis as defined by the Hanifin and Rajika criteria.
4. The method of any one of embodiments 1-3, wherein said the two administrations per day are at least 8 hours apart.
5. The method of any one of embodiments 1-4, wherein the cream formulation is an oil-in-water emulsion comprising said 1.5% (w/w) on a free base basis of ruxolitinib phosphate.
6. The method of any one of embodiments 1-5, wherein the cream formulation has a pH from about 2.8 to about 3.6.
7. The method of any one of embodiments 1-6, wherein the cream formulation is a solubilized cream.
8. The method of any one of embodiments 1-7, wherein the patient achieves a statistically significant reduction in itch Numerical Rating Scale score from baseline at day 2 of said administering compared to a patient administered placebo for the same period.
9. The method of any one of embodiments 1-8, wherein the patient achieves at least a 1.5 point reduction in itch Numerical Rating Scale score from baseline at day 2 of said administering.
10. The method of any one of embodiments 1-9, wherein the patient achieves a statistically significant reduction in itch Numerical Rating Scale score from baseline at week 2 of said administering compared to a patient administered placebo for the same period.
11. The method of any one of embodiments 1-10, wherein the patient achieves at least a 3 point reduction in itch Numerical Rating Scale score from baseline at week 2 of said administering.
12. The method of any one of embodiments 1-11, wherein the patient achieves a statistically significant reduction in itch Numerical Rating Scale score from baseline at week 4 of said administering compared to a patient administered placebo for the same period.
13. The method of any one of embodiments 1-12, wherein the patient achieves at least a 3 point reduction in itch Numerical Rating Scale score from baseline at week 4 of said administering.
14. The method of any one of embodiments 1-13, wherein the patient achieves a statistically significant reduction in itch Numerical Rating Scale score from baseline at week 8 of said administering compared to a patient administered placebo for the same period.
15. The method of any one of embodiments 1-14, wherein the patient achieves at least a 3 point reduction in itch Numerical Rating Scale score from baseline at week 8 of said administering.
16. The method of any one of embodiments 1-15, wherein the patient achieves at least a 4 point reduction in itch Numerical Rating Scale score from baseline at week 8 of said administering.
17. The method of any one of embodiments 1-16, wherein the patient achieves at least a 4.5 point reduction in itch Numerical Rating Scale score from baseline at week 12 of said administering.
18. The method of any one of embodiments 1-17, wherein said administering reverses the symptomatology of atopic dermatitis.
19. The method of any one of embodiments 1-18, wherein the patient achieves a statistically significant improvement in Eczema Area and Severity Index score from baseline at week 4 of said administering compared to a patient administered placebo for the same period.
20. The method of any one of embodiments 1-19, wherein the patient achieves a statistically significant improvement in Eczema Area and Severity Index score from baseline at week 8 of said administering compared to a patient administered placebo for the same period.

21. The method of any one of embodiments 1-20, wherein the patient achieves a 75% improvement in Eczema Area and Severity Index score from baseline at week 2 of said administering.

22. The method of any one of embodiments 1-21, wherein the patient achieves a 75% improvement in Eczema Area and Severity Index score from baseline at week 4 of said administering.

23. The method of any one of embodiments 1-22, wherein the patient achieves a 75% improvement in Eczema Area and Severity Index score from baseline at week 8 of said administering.

24. The method of any one of embodiments 1-23, wherein the patient achieves a 75% improvement in Eczema Area and Severity Index score from baseline at week 12 of said administering.

25. The method of any one of embodiments 1-24, wherein the patient achieves an Investigator's Global Assessment score of 0 or 1 with an improvement of at least 2 points from baseline at 2 weeks of said administering.

26. The method of any one of embodiments 1-25, wherein the patient achieves an Investigator's Global Assessment score of 0 or 1 with an improvement of at least 2 points from baseline at 4 weeks of said administering.

27. The method of any one of embodiments 1-26, wherein the patient achieves an Investigator's Global Assessment score of 0 or 1 with an improvement of at least 2 points from baseline at 8 weeks of said administering.

28. The method of any one of embodiments 1-27, wherein the patient achieves a clinically meaningful improvement in the PROMIS Short Form—Sleep Disturbances (8b) 24-hour recall score at Week 8.

29. The method of any one of embodiments 1-28, wherein said administering is maintained for at least 2 weeks.

30. The method of any one of embodiments 1-29, wherein said administering is maintained for at least 4 weeks.

31. The method of any one of embodiments 1-30, wherein said administering is maintained for at least 8 weeks.

32. The method of any one of embodiments 1-31, wherein said administering is maintained for at least 12 weeks.

33. The method of any one of embodiments 1-32, wherein the patient did not use topical treatments for atopic dermatitis, other than bland emollients, within 2 weeks of baseline; and did not use systemic immunosuppressive or systemic immunomodulating drugs within 4 weeks of baseline.

34. The method of any one of embodiments 1-33, wherein the patient is not administered other therapeutic agents used to treat atopic dermatitis.

35. A method of reducing itch in a human patient with atopic dermatitis, comprising administering to the skin of said human patient in need thereof, a cream formulation two times per day, wherein said cream formulation is an oil-in-water emulsion, comprising 1.5% (w/w) on a free base basis of ruxolitinib phosphate,
wherein said administering is maintained for at least 8 weeks,
wherein the patient achieves at least a 4 point reduction in itch NRS score from baseline at week 8 of said administering, and
wherein the patient achieves an Investigator's Global Assessment score of 0 or 1 with an improvement of at least 2 points from baseline at 8 weeks of said administering.

36. The method of embodiment 35, wherein the patient achieves an Investigator's Global Assessment score of 0 or 1 with an improvement of at least 2 points from baseline at 8 weeks of said administering.

37. The method of embodiment 35 or 36, wherein the patient is:
is aged 18 to 70 years,
has been diagnosed with atopic dermatitis for at least 2 years,
has an IGA score of 2 to 3 at screening and baseline, and
has a BSA of atopic dermatitis involvement (excluding face and intertriginous areas) of 3% to 20% at baseline.

38. A method of reducing itch in a human patient with atopic dermatitis, comprising administering to the skin of said human patient in need thereof, a cream formulation two times per day, wherein said cream formulation comprises 1.5% (w/w) on a free base basis of ruxolitinib, or a pharmaceutically acceptable salt thereof,
wherein said patient achieves a reduction in the itch Numerical Rating Scale score from baseline.

39. A method of reducing itch in a human patient with atopic dermatitis, comprising administering to the skin of said human patient in need thereof, a cream formulation two times per day, wherein said cream formulation comprises 0.75% (w/w) on a free base basis of ruxolitinib, or a pharmaceutically acceptable salt thereof,
wherein said patient achieves a reduction in the itch Numerical Rating Scale score from baseline.

40. The method of embodiment 38 or 39, wherein the ruxolitinib, or a pharmaceutically acceptable salt thereof, is ruxolitinib phosphate.

41. The method of any one of embodiments 38-40, wherein said patient:
is aged 18 to 70 years,
has been diagnosed with atopic dermatitis for at least 2 years,
has an Investigator's Global Assessment score of 2 to 3 at screening and baseline, and
has a BSA of atopic dermatitis involvement (excluding face and intertriginous areas) of 3% to 20% at baseline.

42. The method of any one of embodiments 38-41, wherein the patient is diagnosed with atopic dermatitis as defined by the Hanifin and Rajika criteria.

43. The method of any one of embodiments 38-42, wherein the patient achieves at least a 4 point improvement in improvement in itch Numerical Rating Scale score from baseline.

44. The method of any one of embodiments 38-43, wherein the patient achieves at least a 4 point improvement in improvement in itch Numerical Rating Scale score from baseline, wherein the patient has a baseline Numerical Rating Scale score of equal to or greater than 4.

45. The method of any one of embodiments 38-44, wherein the patient achieves at least a 4 point improvement in improvement in itch Numerical Rating Scale score from baseline after 2 weeks of said administering, wherein the patient has a baseline Numerical Rating Scale score of equal to or greater than 4.

46. The method of any one of embodiments 38-45, wherein the patient achieves at least a 4 point improvement in improvement in itch Numerical Rating Scale score from baseline after 4 weeks of said administering, wherein the patient has a baseline Numerical Rating Scale score of equal to or greater than 4.

47. The method of any one of embodiments 38-46, wherein the patient achieves at least a 4 point improvement in improvement in itch Numerical Rating Scale score from baseline after 8 weeks of said administering, wherein the patient has a baseline Numerical Rating Scale score of equal to or greater than 4.
48. The method of any one of embodiments 38-47, wherein the patient achieves at least a 2 point improvement in itch Numerical Rating Scale score from baseline at day 2 of said administering.
49. The method of any one of embodiments 38-49, wherein the patient achieves a prompt reduction of itch.
50. The method of any one of embodiments 38-49, wherein the patient achieves a statistically significant reduction of itch at day 1 of said administering.
51. The method of any one of embodiments 38-50, wherein the patient achieves a statistically significant reduction in itch Numerical Rating Scale score from baseline at day 1 of said administering compared to a patient administered placebo for the same period.
52. The method of any one of embodiments 38-51, wherein the patient achieves at least a 1 point reduction in itch Numerical Rating Scale score from baseline at day 1 of said administering.
53. The method of any one of embodiments 38-52, wherein the patient achieves a statistically significant reduction in itch Numerical Rating Scale score from baseline at day 2 of said administering compared to a patient administered placebo for the same period.
54. The method of any one of embodiments 38-53, wherein the patient achieves at least a 2 point reduction in itch Numerical Rating Scale score from baseline at day 2 of said administering.
55. The method of any one of embodiments 38-54, wherein the patient achieves at least a 3 point reduction in itch Numerical Rating Scale score from baseline at week 2 of said administering.
56. The method of any one of embodiments 38-55, wherein the patient achieves at least a 3 point reduction in itch Numerical Rating Scale score from baseline at week 4 of said administering.
57. The method of any one of embodiments 38-56, wherein the patient achieves at least a 3 point reduction in itch Numerical Rating Scale score from baseline at week 8 of said administering.
58. The method of any one of embodiments 38-57, wherein the patient achieves at least a 4 point reduction in itch Numerical Rating Scale score from baseline at week 2 of said administering.
59. The method of any one of embodiments 38-58, wherein the patient achieves at least a 4 point reduction in itch Numerical Rating Scale score from baseline at week 4 of said administering.
60. The method of any one of embodiments 38-59, wherein the patient achieves at least a 4 point reduction in itch Numerical Rating Scale score from baseline at week 8 of said administering.
61. The method of any one of embodiments 38-60, wherein said administering reverses the symptomatology of atopic dermatitis.
62. The method of any one of embodiments 38-61, wherein the patient achieves a statistically significant improvement in Eczema Area and Severity Index score from baseline at week 4 of said administering compared to a patient administered placebo for the same period.
63. The method of any one of embodiments 38-62, wherein the patient achieves a statistically significant improvement in Eczema Area and Severity Index score from baseline at week 8 of said administering compared to a patient administered placebo for the same period.
64. The method of any one of embodiments 38-63, wherein the patient achieves a 75% improvement in Eczema Area and Severity Index score from baseline at week 2 of said administering.
65. The method of any one of embodiments 38-64, wherein the patient achieves a 75% improvement in Eczema Area and Severity Index score from baseline at week 4 of said administering.
66. The method of any one of embodiments 38-65, wherein the patient achieves a 75% improvement in Eczema Area and Severity Index score from baseline at week 8 of said administering.
67. The method of any one of embodiments 38-66, wherein the patient achieves a 75% improvement in Eczema Area and Severity Index score from baseline at week 12 of said administering.
68. The method of any one of embodiments 38-67, wherein the patient achieves an Investigator's Global Assessment score of 0 or 1 with an improvement of at least 2 points from baseline at 2 weeks of said administering.
69. The method of any one of embodiments 38-68, wherein the patient achieves an Investigator's Global Assessment score of 0 or 1 with an improvement of at least 2 points from baseline at 4 weeks of said administering.
70. The method of any one of embodiments 38-69, wherein the patient achieves an Investigator's Global Assessment score of 0 or 1 with an improvement of at least 2 points from baseline at 8 weeks of said administering.
71. The method of any one of embodiments 38-70, wherein the patient achieves a clinically meaningful improvement in the PROMIS Short Form—Sleep Disturbances (8b) 24-hour recall score at Week 8.
72. The method of any one of embodiments 38-71, wherein said administering is maintained for at least 2 weeks.
73. The method of any one of embodiments 38-72, wherein said administering is maintained for at least 4 weeks.
74. The method of any one of embodiments 38-73, wherein said administering is maintained for at least 8 weeks.
75. The method of any one of embodiments 38-74, wherein said administering is maintained for at least 12 weeks.
76. The method of any one of embodiments 38-75, wherein the patient did not use topical treatments for atopic dermatitis, other than bland emollients, within 2 weeks of baseline; and did not use systemic immunosuppressive or systemic immunomodulating drugs within 4 weeks of baseline.
77. The method of any one of embodiments 38-76, wherein the patient is not administered other therapeutic agents used to treat atopic dermatitis.
78. The method of any one of embodiments 38-77 wherein said administering of said cream formulation does not result in a statistically significant reduction in hemoglobin or platelets.
79. The method of any one of embodiments 38-78, wherein said administering of said cream formulation does not result administration site burn.
80. The method of any one of embodiments 38-79, wherein the cream formulation is an oil-in-water emulsion comprising said ruxolitinib, or pharmaceutically acceptable salt thereof.
81. The method of any one of embodiments 38-80, wherein the cream formulation has a pH from about 2.8 to about 3.6.
82. The method of any one of embodiments 38-81, wherein the cream formulation is a solubilized cream.

83. The method of any one of embodiments 38-82, wherein said the two administrations per day are at least 8 hours apart.
84. A method of reducing itch in a human patient with atopic dermatitis, comprising administering to the skin of said human patient in need thereof, a cream formulation two times per day, wherein said cream formulation is an oil-in-water emulsion, comprising 1.5% (w/w) on a free base basis of ruxolitinib phosphate,
wherein said administering is maintained for at least 8 weeks,
wherein the patient achieves at least a 4 point reduction in itch NRS score from baseline at week 8 of said administering, and
wherein the patient achieves an Investigator's Global Assessment score of 0 or 1 with an improvement of at least 2 points from baseline at 8 weeks of said administering.
85. The method of embodiment 84, wherein the patient achieves an Investigator's Global Assessment score of 0 or 1 with an improvement of at least 2 points from baseline at 8 weeks of said administering.
86. The method of embodiment 84 or 85, wherein the patient is:
is aged 18 to 70 years,
has been diagnosed with atopic dermatitis for at least 2 years,
has an Investigator's Global Assessment score of 2 to 3 at screening and baseline, and
has a BSA of atopic dermatitis involvement (excluding face and intertriginous areas) of 3% to 20% at baseline.
87. A method of treating atopic dermatitis in a human patient, comprising administering to the skin of said human patient in need thereof, a cream formulation two times per day, wherein said cream formulation comprises 0.75% (w/w) on a free base basis of ruxolitinib, or a pharmaceutically acceptable salt thereof.
88. The method of embodiment 87, wherein the ruxolitinib, or a pharmaceutically acceptable salt thereof, is ruxolitinib phosphate.
89. The method of any one of embodiments 87-88, wherein the patient achieves Investigator's Global Assessment score of 0 or 1 with an improvement of at least 2 points from baseline.
90. The method of any one of embodiments 87-89, wherein the patient achieves an Investigator's Global Assessment score of 0 or 1 with an improvement of at least 2 points from baseline at 2 weeks of said administering.
91. The method of any one of embodiments 87-90, wherein the patient achieves an Investigator's Global Assessment score of 0 or 1 with an improvement of at least 2 points from baseline at 4 weeks of said administering.
92. The method of any one of embodiments 87-91, wherein the patient achieves an Investigator's Global Assessment score of 0 or 1 with an improvement of at least 2 points from baseline at 8 weeks of said administering.
93. The method of any one of embodiments 87-92, wherein the patient achieves a 75% improvement in Eczema Area and Severity Index score from baseline.
94. The method of any one of embodiments 87-93, wherein the patient achieves a statistically significant improvement in Eczema Area and Severity Index score from baseline at week 4 of said administering compared to a patient administered placebo for the same period.
95. The method of any one of embodiments 87-94, wherein the patient achieves a statistically significant improvement in Eczema Area and Severity Index score from baseline at week 8 of said administering compared to a patient administered placebo for the same period.
96. The method of any one of embodiments 87-95, wherein the patient achieves a 75% improvement in Eczema Area and Severity Index score from baseline at week 2 of said administering.
97. The method of any one of embodiments 87-96, wherein the patient achieves a 75% improvement in Eczema Area and Severity Index score from baseline at week 4 of said administering.
98. The method of any one of embodiments 87-97, wherein the patient achieves a 75% improvement in Eczema Area and Severity Index score from baseline at week 8 of said administering.
99. The method of any one of embodiments 87-98, wherein the patient achieves a 75% improvement in Eczema Area and Severity Index score from baseline at week 12 of said administering.
100. The method of any one of embodiments 87-99, wherein the patient achieves a clinically meaningful improvement in the PROMIS Short Form—Sleep Disturbances (8b) 24-hour recall score.
101. The method of any one of embodiments 87-100, wherein the patient achieves a clinically meaningful improvement in the PROMIS Short Form—Sleep Disturbances (8b) 24-hour recall score at Week 8.
102. The method of any one of embodiments 87-101, wherein said administering is maintained for at least 2 weeks.
103. The method of any one of embodiments 87-102, wherein said administering is maintained for at least 4 weeks.
104. The method of any one of embodiments 87-103, wherein said administering is maintained for at least 8 weeks.
105. The method of any one of embodiments 87-104, wherein said administering is maintained for at least 12 weeks.
106. The method of any one of embodiments 87-105, wherein the patient did not use topical treatments for atopic dermatitis, other than bland emollients, within 2 weeks of baseline; and did not use systemic immunosuppressive or systemic immunomodulating drugs within 4 weeks of baseline.
107. The method of any one of embodiments 87-106, wherein the patient is not administered other therapeutic agents used to treat atopic dermatitis.
108. The method of any one of embodiments 87-107, wherein said the two administrations per day are at least 8 hours apart.
109. The method of any one of embodiments 87-108, wherein the cream formulation is an oil-in-water emulsion comprising said 0.75% (w/w) on a free base basis of ruxolitinib phosphate.
110. The method of any one of embodiments 87-109, wherein the cream formulation has a pH from about 2.8 to about 3.6.
111. The method of any one of embodiments 87-110, wherein the cream formulation is a solubilized cream.
112. The method of any one of embodiments 87-111, wherein said patient:
is aged 18 to 70 years,
has been diagnosed with atopic dermatitis for at least 2 years,
has an Investigator's Global Assessment score of 2 to 3 at screening and baseline, and has a BSA of atopic dermatitis involvement (excluding face and intertriginous areas) of 3% to 20% at baseline.
113. The method of any one of embodiments 87-112, wherein the patient is diagnosed with atopic dermatitis as defined by the Hanifin and Rajika criteria.
114. The method of any one of embodiments 87-113, wherein the patient achieves at least a 4 point improvement in improvement in itch Numerical Rating Scale score from baseline.
115. The method of any one of embodiments 87-114, wherein the patient achieves at least a 4 point improvement in improvement in itch Numerical Rating Scale score from baseline, wherein the patient has a baseline Numerical Rating Scale score of equal to or greater than 4.
116. The method of any one of embodiments 87-115, wherein the patient achieves at least a 4 point improvement in improvement in itch Numerical Rating Scale score from baseline after 2 weeks of said administering, wherein the patient has a baseline Numerical Rating Scale score of equal to or greater than 4.
117. The method of any one of embodiments 87-116, wherein the patient achieves at least a 4 point improvement in improvement in itch Numerical Rating Scale score from baseline after 4 weeks of said administering, wherein the patient has a baseline Numerical Rating Scale score of equal to or greater than 4.
118. The method of any one of embodiments 87-117, wherein the patient achieves at least a 4 point improvement in improvement in itch Numerical Rating Scale score from baseline after 8 weeks of said administering, wherein the patient has a baseline Numerical Rating Scale score of equal to or greater than 4.
119. The method of any one of embodiments 87-118, wherein the patient achieves at least a 2 point improvement in itch Numerical Rating Scale score from baseline at day 2 of said administering.
120. The method of any one of embodiments 87-119, wherein said administering of said cream formulation does not result in a statistically significant reduction in hemoglobin or platelets.
121. The method of any one of embodiments 87-120, wherein said administering of said cream formulation does not result administration site burn.
122. A method of treating moderate atopic dermatitis in a human patient comprising administering to the skin of said human patient in need thereof, a topical formulation two times per day, wherein said topical formulation comprises 0.75% (w/w) or 1.5% (w/w) on a free base basis of ruxolitinib, or a pharmaceutically acceptable salt thereof.
123. A method of treating moderate to severe atopic dermatitis in a human patient comprising administering to the skin of said human patient in need thereof, a topical formulation two times per day, wherein said topical formulation comprises 0.75% (w/w) or 1.5% (w/w) on a free base basis of ruxolitinib, or a pharmaceutically acceptable salt thereof.
124. A method of treating atopic dermatitis in a human patient comprising administering to the skin of said human patient in need thereof, a topical formulation two times per day, wherein the topical formulation comprises 0.75% (w/w) or 1.5% (w/w) on a free base basis of ruxolitinib, or a pharmaceutically acceptable salt thereof, wherein said patient has:
an Eczema Area and Severity Index score of ≥16 at baseline; and
a Body Surface Area of atopic dermatitis involvement of ≥10% at baseline.
125. The method of any one of embodiments 122-124, wherein the topical formulation is a cream formulation.
126. The method of any one of embodiments 122-125, wherein the formulation comprises 0.75% (w/w) on a free base basis of ruxolitinib, or a pharmaceutically acceptable salt thereof.
127. The method of any one of embodiments 122-125, wherein the formulation comprises 1.5% (w/w) on a free base basis of ruxolitinib, or a pharmaceutically acceptable salt thereof.
128. The method of any one of embodiments 122-125, wherein the formulation comprises 0.75% (w/w) on a free base basis of ruxolitinib phosphate.
129. The method of any one of embodiments 122-125, wherein the formulation comprises 1.5% (w/w) on a free base basis of ruxolitinib phosphate.
130. The method of any one of embodiments 122-129, wherein the patient has an itch Numerical Rating scale of score of ≥4 at baseline.
131. The method of any one of embodiments 122-130, wherein the patient has an Investigator's Global Assessment score of 3 at baseline.
132. The method of any one of embodiments 122-130, wherein the patient has an Investigator's Global Assessment score of from 3 to 4 at baseline.
133. The method of any one of embodiments 122-129, wherein the patient:
has an Investigator's Global Assessment score of 3 at baseline; and
has an itch Numerical Rating scale of score of ≥4 at baseline.
134. The method of any one of embodiments 122-129, wherein the patient:
has an Investigator's Global Assessment score of from 3 to 4 at baseline; and
has an itch Numerical Rating scale of score of ≥4 at baseline.
135. The method of any one of embodiments 122-134, wherein the patient is aged ≥12 years.
136. The method of any one of embodiments 122-135, wherein the patient has a history of atopic dermatitis for at least 2 years.
137. The method of any one of embodiments 122-129, wherein the patient:
has an Investigator's Global Assessment score of 3 at baseline;
has a history of atopic dermatitis for at least 2 years; and
is aged ≥12 years.
138. The method of any one of embodiments 122-129, wherein the patient:
has an Investigator's Global Assessment score of from 3 to 4 at baseline;
has a history of atopic dermatitis for at least 2 years; and
is aged ≥12 years.
139. The method of any one of embodiments 122-129, wherein the patient:
has an Investigator's Global Assessment score of 3 at baseline;
has an itch Numerical Rating scale of score of ≥4 at baseline;
has a history of atopic dermatitis for at least 2 years; and
is aged ≥12 years.
140. The method of any one of embodiments 122-129, wherein the patient:

has an Investigator's Global Assessment score of from 3 to 4 at baseline;
has an itch Numerical Rating scale of score of ≥4 at baseline;
has a history of atopic dermatitis for at least 2 years; and is aged ≥12 years.

141. The method of any one of embodiments 122-129, wherein the patient has one or more of the following characteristics:
an Investigator's Global Assessment score of 3 at baseline;
an itch Numerical Rating scale of score of ≥4 at baseline;
a history of atopic dermatitis for at least 2 years; and aged ≥12 years.

142. The method of any one of embodiments 122-129, wherein the patient has one or more of the following characteristics:
an Investigator's Global Assessment score of from 3 to 4 at baseline;
an itch Numerical Rating scale of score of ≥4 at baseline;
a history of atopic dermatitis for at least 2 years; and aged ≥12 years.

143. The method of any one of embodiments 122-142, wherein the patient is diagnosed with atopic dermatitis as defined by the Hanifin and Rajika criteria.

144. The method of any one of embodiments 122-143, wherein said administering is maintained for at least 2 weeks.

145. The method of any one of embodiments 122-143, wherein said administering is maintained for at least 4 weeks.

146. The method of any one of embodiments 122-143, wherein said administering is maintained for at least 8 weeks.

147. The method of any one of embodiments 122-146, wherein the patient achieves Investigator's Global Assessment score of 0 or 1 with an improvement of at least 2 points from baseline.

148. The method of any one of embodiments 122-146, wherein the patient achieves an Investigator's Global Assessment score of 0 or 1 with an improvement of at least 2 points from baseline at 2 weeks of said administering.

149. The method of any one of embodiments 122-146, wherein the patient achieves an Investigator's Global Assessment score of 0 or 1 with an improvement of at least 2 points from baseline at 4 weeks of said administering.

150. The method of any one of embodiments 122-146, wherein the patient achieves an Investigator's Global Assessment score of 0 or 1 with an improvement of at least 2 points from baseline at 8 weeks of said administering.

151. The method of any one of embodiments 122-150, wherein the patient achieves a 75% improvement in Eczema Area and Severity Index score from baseline.

152. The method of any one of embodiments 122-151, wherein the patient achieves a statistically significant improvement in Eczema Area and Severity Index score from baseline at week 4 of said administering compared to a patient administered placebo for the same period.

153. The method of any one of embodiments 122-152, wherein the patient achieves a statistically significant improvement in Eczema Area and Severity Index score from baseline at week 8 of said administering compared to a patient administered placebo for the same period.

154. The method of any one of embodiments 122-153, wherein the patient achieves a 75% improvement in Eczema Area and Severity Index score from baseline at week 2 of said administering.

155. The method of any one of embodiments 122-153, wherein the patient achieves a 75% improvement in Eczema Area and Severity Index score from baseline at week 4 of said administering.

156. The method of any one of embodiments 122-153, wherein the patient achieves a 75% improvement in Eczema Area and Severity Index score from baseline at week 8 of said administering.

157. The method of any one of embodiments 122-156, wherein the patient achieves at least a 4 point improvement in improvement in itch Numerical Rating Scale score from baseline, wherein the patient has a baseline Numerical Rating Scale score of equal to or greater than 4.

158. The method of any one of embodiments 122-156, wherein the patient achieves at least a 4 point improvement in improvement in itch Numerical Rating Scale score from baseline after 2 weeks of said administering, wherein the patient has a baseline Numerical Rating Scale score of equal to or greater than 4.

159. The method of any one of embodiments 122-156, wherein the patient achieves at least a 4 point improvement in improvement in itch Numerical Rating Scale score from baseline after 4 weeks of said administering, wherein the patient has a baseline Numerical Rating Scale score of equal to or greater than 4.

160. The method of any one of embodiments 122-156, wherein the patient achieves at least a 4 point improvement in improvement in itch Numerical Rating Scale score from baseline after 8 weeks of said administering, wherein the patient has a baseline Numerical Rating Scale score of equal to or greater than 4.

161. The method of any one of embodiments 122-160, wherein the patient achieves at least a 2 point improvement in itch Numerical Rating Scale score from baseline at day 2 of said administering.

162. The method of any one of embodiments 122-161, wherein the patient achieves a clinically meaningful improvement in the PROMIS Short Form—Sleep Disturbances (8b) 24-hour recall score.

163. The method of any one of embodiments 122-162, wherein the patient achieves a clinically meaningful improvement in the PROMIS Short Form—Sleep Disturbances (8b) 24-hour recall score at Week 8.

164. The method of any one of embodiments 122-143, wherein:
the patient achieves at least a 4-point reduction in itch Numerical Rating Scale score from baseline at week 4 of said administering; and
the patient achieves an Investigator's Global Assessment score of 0 or 1 with an improvement of at least 2 points from baseline at week 4 of said administering.

165. The method of any one of embodiments 122-143, wherein:
the patient achieves at least a 4-point reduction in itch Numerical Rating Scale score from baseline at week 8 of said administering; and
the patient achieves an Investigator's Global Assessment score of 0 or 1 with an improvement of at least 2 points from baseline at week 8 of said administering.

166. The method of any one of embodiments 122-143, wherein:

the patient achieves at least a 4-point reduction in itch Numerical Rating Scale score from baseline at week 4 of said administering; and the patient achieves a 75% improvement in Eczema Area and Severity Index score from baseline at week 4 of said administering.

167. The method of any one of embodiments 122-143, wherein:
the patient achieves at least a 4-point reduction in itch Numerical Rating Scale score from baseline at week 8 of said administering; and
the patient achieves a 75% improvement in Eczema Area and Severity Index score from baseline at week 8 of said administering.

168. The method of any one of embodiments 122-143, wherein:
the patient achieves an Investigator's Global Assessment score of 0 or 1 with an improvement of at least 2 points from baseline at week 4 of said administering; and
the patient achieves a 75% improvement in Eczema Area and Severity Index score from baseline at week 4 of said administering.

169. The method of any one of embodiments 122-143, wherein:
the patient achieves an Investigator's Global Assessment score of 0 or 1 with an improvement of at least 2 points from baseline at week 8 of said administering; and
the patient achieves a 75% improvement in Eczema Area and Severity Index score from baseline at week 8 of said administering.

170. The method of any one of embodiments 122-143, wherein:
the patient achieves at least a 4-point reduction in itch Numerical Rating Scale score from baseline at week 4 of said administering;
the patient achieves an Investigator's Global Assessment score of 0 or 1 with an improvement of at least 2 points from baseline at week 4 of said administering; and
the patient achieves a 75% improvement in Eczema Area and Severity Index score from baseline at week 4 of said administering.

171. The method of any one of embodiments 122-143, wherein:
the patient achieves at least a 4-point reduction in itch Numerical Rating Scale score from baseline at week 8 of said administering;
the patient achieves an Investigator's Global Assessment score of 0 or 1 with an improvement of at least 2 points from baseline at week 8 of said administering; and
the patient achieves a 75% improvement in Eczema Area and Severity Index score from baseline at week 8 of said administering.

172. The method of any one of embodiments 122-171, wherein the patient did not use topical treatments for atopic dermatitis, other than bland emollients, within 2 weeks of baseline; and did not use systemic immunosuppressive or systemic immunomodulating drugs within 4 weeks of baseline.

173. The method of any one of embodiments 122-172, wherein the patient is not administered other therapeutic agents used to treat atopic dermatitis.

174. The method of any one of embodiments 122-173, wherein said the two administrations per day are at least 8 hours apart.

175. The method of any one of embodiments 122-174, wherein the formulation has a pH from about 2.8 to about 3.9.

176. The method of any one of embodiments 122-174, wherein the formulation has a pH from about 2.8 to about 3.6.

177. The method of any one of embodiments 122-176, wherein the formulation is a solubilized cream.

178. The method of any one of embodiments 122-177, wherein said administering of said formulation does not result in a statistically significant reduction in hemoglobin or platelets.

179. The method of any one of embodiments 122-178, wherein said administering of said formulation does not result administration site burn.

180. A method of treating moderate atopic dermatitis in a human patient comprising administering to the skin of said human patient in need thereof, a topical formulation two times per day, wherein said topical formulation comprises 1.5% (w/w) on a free base basis of ruxolitinib, or a pharmaceutically acceptable salt thereof.

181. The method of embodiment 180, wherein the ruxolitinib, or a pharmaceutically acceptable salt thereof, is ruxolitinib phosphate.

182. The method of embodiment 180, wherein the patient is aged 12 years or older.

183. The method of embodiment 180, wherein patient has a Body Surface Area of atopic dermatitis involvement of from 10% to 20% at baseline.

184. The method of embodiment 180, wherein the patient has an Eczema Area and Severity Index score of ≥16 at baseline.

185. The method of embodiment 180, wherein the patient achieves an Investigator's Global Assessment score of 0 or 1 with an improvement of at least 2 points from baseline.

186. The method of embodiment 180, wherein the patient achieves a 75% improvement in Eczema Area and Severity Index score from baseline.

187. The method of embodiment 180, wherein the patient achieves at least a 4 point improvement in improvement in itch Numerical Rating Scale score from baseline, and wherein the patient has a baseline Numerical Rating Scale score of equal to or greater than 4.

188. The method of embodiment 180, wherein the patient achieves:
an Investigator's Global Assessment score of 0 or 1 with an improvement of at least 2 points from baseline;
a 4 point improvement in improvement in itch Numerical Rating Scale score from baseline, wherein the patient has a baseline Numerical Rating Scale score of equal to or greater than 4; and
a 75% improvement in Eczema Area and Severity Index score from baseline.

189. The method of embodiment 180, wherein the patient achieves:
an Investigator's Global Assessment score of 0 or 1 with an improvement of at least 2 points from baseline at Week 4;
a 4 point improvement in improvement in itch Numerical Rating Scale score from baseline at Week 4, wherein the patient has a baseline Numerical Rating Scale score of equal to or greater than 4; and
a 75% improvement in Eczema Area and Severity Index score from baseline at Week 4.

190. The method of embodiment 180, wherein the patient achieves:
an Investigator's Global Assessment score of 0 or 1 with an improvement of at least 2 points from baseline at Week 8;

a 4 point improvement in improvement in itch Numerical Rating Scale score from baseline at Week 8, wherein the patient has a baseline Numerical Rating Scale score of equal to or greater than 4; and a 75% improvement in Eczema Area and Severity Index score from baseline at Week 8.

191. The method of embodiment 180, wherein the patient achieves at least a 2 point improvement in itch Numerical Rating Scale score from baseline at day 2 of said administering.

192. The method of embodiment 180, wherein the patient achieves a clinically meaningful improvement in the PROMIS Short Form—Sleep Disturbances (8b) 24-hour recall score at Week 8.

193. The method of embodiment 180, wherein the formulation is a cream formulation.

194. The method of embodiment 193, wherein the cream formulation is an oil-in-water emulsion.

195. The method of embodiment 194, wherein the cream formulation has a pH from about 2.8 to about 3.9.

196. The method of embodiment 195, wherein said administering of said formulation does not result in a statistically significant reduction in hemoglobin or platelets.

197. The method of embodiment 196, wherein said administering of said formulation does not result in administration site burn.

198. A method of treating atopic dermatitis in a human patient comprising administering to the skin of said human patient in need thereof, a topical formulation two times per day, wherein said topical formulation comprises 1.5% (w/w) on a free base basis of ruxolitinib phosphate, wherein said patient:
is aged 12 years or older;
has a Body Surface Area of atopic dermatitis involvement of from 10% to 20% at baseline; and
has an Investigator's Global Assessment score of 3 at baseline.

199. The method of embodiment 198, wherein the patient achieves Investigator's Global Assessment score of 0 or 1 with an improvement of at least 2 points from baseline.

200. The method of embodiment 198, wherein the patient achieves a 75% improvement in Eczema Area and Severity Index score from baseline.

201. The method of embodiment 198, wherein the patient achieves at least a 4 point improvement in improvement in itch Numerical Rating Scale score from baseline, and wherein the patient has a baseline Numerical Rating Scale score of equal to or greater than 4.

202. The method of embodiment 198, wherein the patient achieves:
an Investigator's Global Assessment score of 0 or 1 with an improvement of at least 2 points from baseline;
a 4 point improvement in improvement in itch Numerical Rating Scale score from baseline, wherein the patient has a baseline Numerical Rating Scale score of equal to or greater than 4; and
a 75% improvement in Eczema Area and Severity Index score from baseline.

203. The method of embodiment 198, wherein the patient achieves:
an Investigator's Global Assessment score of 0 or 1 with an improvement of at least 2 points from baseline at Week 4;
a 4 point improvement in improvement in itch Numerical Rating Scale score from baseline at Week 4, wherein the patient has a baseline Numerical Rating Scale score of equal to or greater than 4; and
a 75% improvement in Eczema Area and Severity Index score from baseline at Week 4.

204. The method of embodiment 198, wherein the patient achieves:
an Investigator's Global Assessment score of 0 or 1 with an improvement of at least 2 points from baseline at Week 8;
a 4 point improvement in improvement in itch Numerical Rating Scale score from baseline at Week 8, wherein the patient has a baseline Numerical Rating Scale score of equal to or greater than 4; and
a 75% improvement in Eczema Area and Severity Index score from baseline at Week 8.

205. The method of embodiment 198, wherein the formulation is a cream formulation.

206. The method of embodiment 205, wherein the cream formulation is an oil-in-water emulsion.

207. A method of reducing itch in a human patient with atopic dermatitis, comprising administering to the skin of said human patient in need thereof, a cream formulation two times per day, wherein said cream formulation comprises 1.5% (w/w) on a free base basis of ruxolitinib, or a pharmaceutically acceptable salt thereof;
wherein said patient achieves a statistically significant reduction in itch Numerical Rating Scale score from baseline within 36 hours of said administering.

208. A method of reducing itch in a human patient with atopic dermatitis, comprising administering to the skin of said human patient in need thereof, a cream formulation two times per day, wherein said cream formulation comprises 1.5% (w/w) on a free base basis of ruxolitinib, or a pharmaceutically acceptable salt thereof, wherein the patient achieves at least a 1 point reduction in itch Numerical Rating Scale score by day 2 of said administering.

209. The method of embodiment 208, wherein the ruxolitinib, or a pharmaceutically acceptable salt thereof, is ruxolitinib phosphate.

210. The method of embodiment 208, wherein the patient achieves a statistically significant reduction in the itch Numerical Rating Scale score from baseline within 12 hours of said administering.

211. The method of embodiment 208, wherein the patient achieves a 2 point improvement in itch Numerical Rating Scale score within 12 hours of said administering.

212. The method of embodiment 208, wherein the patient achieves a 2 point improvement in itch Numerical Rating Scale score within 36 hours of said administering.

213. The method of embodiment 208, wherein the patient achieves a 4 point improvement in itch Numerical Rating Scale score within 36 hours of said administering.

214. The method of embodiment 208, wherein the patient achieves at least a 2 point reduction in itch Numerical Rating Scale score at week 1 of said administering.

215. The method of embodiment 208, wherein the patient achieves at least a 3 point reduction in itch Numerical Rating Scale score at week 3 of said administering.

216. The method of embodiment 208, wherein the patient achieves a minimal clinically important difference in itch Numerical Rating Scale score within 36 hours of said administering, wherein said minimal clinically important difference in itch Numerical Rating Scale score is a 2 to 3 point reduction in itch Numerical Rating Scale score versus baseline, wherein the patient has a baseline Numerical Rating Scale score of equal to or greater than 2.

217. The method of embodiment 208, wherein the patient achieves a clinically relevant improvement in itch Numerical Rating Scale score within 36 hours of said administering, wherein said clinically relevant improvement in itch Numerical Rating Scale score is a ≥4 point reduction in itch Numerical Rating Scale score versus baseline, wherein the patient has a baseline Numerical Rating Scale score of equal to or greater than 4.

218. The method of embodiment 208, wherein said patient is aged 12 or older.

219. The method of embodiment 218, wherein said patient has a Body Surface Area (BSA) of atopic dermatitis involvement (excluding scalp) of 3% to 20% at baseline.

220. The method of embodiment 219, wherein said patient has an Investigator's Global Assessment score of 2 to 3 at baseline.

221. The method of embodiment 220, wherein the patient has been diagnosed with atopic dermatitis for at least 2 years.

222. The method of embodiment 221, wherein the patient is diagnosed with atopic dermatitis as defined by the Hanifin and Rajika criteria.

223. The method of embodiment 222, wherein the patient did not use topical treatments for atopic dermatitis, other than emollients, within 2 weeks of baseline.

224. The method of embodiment 208, wherein the patient achieves at least a 4 point reduction in itch Numerical Rating Scale score from baseline at week 2 of said administering.

225. The method of embodiment 208, wherein the patient achieves at least a 4 point reduction in itch Numerical Rating Scale score from baseline at week 4 of said administering.

226. The method of embodiment 208, wherein the patient achieves at least a 4 point reduction in itch Numerical Rating Scale score from baseline at week 8 of said administering.

227. The method of embodiment 208, wherein the patient achieves a 75% improvement in Eczema Area and Severity Index score from baseline at week 2 of said administering.

228. The method of embodiment 208, wherein the patient achieves a 75% improvement in Eczema Area and Severity Index score from baseline at week 4 of said administering.

229. The method of embodiment 208, wherein the patient achieves a 75% improvement in Eczema Area and Severity Index score from baseline at week 8 of said administering.

230. The method of embodiment 208, wherein the patient achieves an Investigator's Global Assessment score of 0 or 1 with an improvement of at least 2 points from baseline at week 2 of said administering.

231. The method of embodiment 208, wherein the patient achieves an Investigator's Global Assessment score of 0 or 1 with an improvement of at least 2 points from baseline at week 4 of said administering.

232. The method of embodiment 208, wherein the patient achieves an Investigator's Global Assessment score of 0 or 1 with an improvement of at least 2 points from baseline at week 8 of said administering.

233. The method of embodiment 209, wherein the cream formulation is an oil-in-water emulsion.

234. The method of embodiment 233, wherein the cream formulation has a pH from about 2.8 to about 3.6.

235. A method of reducing itch in a human patient with atopic dermatitis, comprising administering to the skin of said human patient in need thereof, a cream formulation two times per day, wherein said cream formulation comprises 1.5% (w/w) on a free base basis of ruxolitinib phosphate;
wherein the patient:
is aged 12 years or older;
has an Investigator's Global Assessment score of 2 to 3 at baseline;
has a Body Surface Area of atopic dermatitis involvement (excluding scalp) of 3% to 20% at baseline; and
achieves a minimal clinically important difference in itch Numerical Rating Scale score within 36 hours of said administering, wherein said minimal clinically important difference in the itch Numerical Rating Scale score is a 2 to 3 point reduction in itch Numerical Rating Scale score versus baseline, wherein the patient has a baseline itch Numerical Rating Scale score of ≥2.

236. A method of reducing itch in a human patient with atopic dermatitis, comprising administering to the skin of said human patient in need thereof, a cream formulation two times per day, wherein said cream formulation comprises 1.5% (w/w) on a free base basis of ruxolitinib phosphate;
wherein the patient:
is aged 12 years or older;
has an Investigator's Global Assessment score of 2 to 3 at baseline;
has a Body Surface Area of atopic dermatitis involvement (excluding scalp) of 3% to 20% at baseline; and
achieves a clinically relevant improvement in itch Numerical Rating Scale score within 36 hours of said administering, wherein the clinically relevant improvement in the itch Numerical Rating Scale score is a ≥4 point reduction in the itch Numerical Rating Scale score versus baseline, wherein the patient has a baseline Numerical Rating Scale score of ≥4.

237. A method of treating atopic dermatitis in a human patient, comprising administering to the skin of the human patient in need thereof, a cream formulation two times per day, wherein the cream formulation comprises 0.75% (w/w) on a free base basis of ruxolitinib, or a pharmaceutically acceptable salt thereof.

238. The method of embodiment 237, wherein the ruxolitinib, or a pharmaceutically acceptable salt thereof, is ruxolitinib phosphate.

239. The method of embodiment 237, wherein the patient achieves Investigator's Global Assessment score of 0 or 1 with an improvement of at least 2 points from baseline.

240. The method of embodiment 237, wherein the patient achieves an Investigator's Global Assessment score of 0 or 1 with an improvement of at least 2 points from baseline at week 2 of the administering.

241. The method of embodiment 237, wherein the patient achieves an Investigator's Global Assessment score of 0 or 1 with an improvement of at least 2 points from baseline at week 4 of the administering.

242. The method of embodiment 237, wherein the patient achieves an Investigator's Global Assessment score of 0 or 1 with an improvement of at least 2 points from baseline at week 8 of the administering.

243. The method of embodiment 237, wherein the patient achieves a 75% improvement in Eczema Area and Severity Index score from baseline.

244. The method of embodiment 237, wherein the patient achieves a 75% improvement in Eczema Area and Severity Index score from baseline at week 2 of the administering.
245. The method of embodiment 237, wherein the patient achieves a 75% improvement in Eczema Area and Severity Index score from baseline at week 4 of the administering.
246. The method of embodiment 237, wherein the patient achieves a 75% improvement in Eczema Area and Severity Index score from baseline at week 8 of the administering.
247. The method of embodiment 237, wherein the patient achieves at least a 4 point improvement in improvement in itch Numerical Rating Scale score from baseline.
248. The method of embodiment 237, wherein the patient achieves at least a 4 point improvement in improvement in itch Numerical Rating Scale score from baseline, and wherein the patient has a baseline Numerical Rating Scale score of equal to or greater than 4.
249. The method of embodiment 237, wherein the patient achieves at least a 4 point improvement in improvement in itch Numerical Rating Scale score from baseline at week 2 of the administering, and wherein the patient has a baseline Numerical Rating Scale score of equal to or greater than 4.
250. The method of embodiment 237, wherein the patient achieves at least a 4 point improvement in improvement in itch Numerical Rating Scale score from baseline at week 4 of the administering, and wherein the patient has a baseline Numerical Rating Scale score of equal to or greater than 4.
251. The method of embodiment 237, wherein the patient achieves at least a 4 point improvement in improvement in itch Numerical Rating Scale score from baseline at week 8 of the administering, and wherein the patient has a baseline Numerical Rating Scale score of equal to or greater than 4.
252. The method of embodiment 237, wherein the patient achieves a minimal clinically important difference in itch Numerical Rating Scale score within 36 hours of the administering wherein the minimal clinically important difference in itch Numerical Rating Scale score is a 2 to 3 point reduction in itch Numerical Rating Scale score versus baseline, wherein the patient has a baseline Numerical Rating Scale score of equal to or greater 2.
253. The method of embodiment 237, wherein the patient achieves a clinically relevant improvement in itch Numerical Rating Scale score within 36 hours of the administering, wherein the clinically relevant improvement in itch Numerical Rating Scale score is a ≥4 point reduction in itch Numerical Rating Scale score versus baseline, wherein the patient has a baseline Numerical Rating Scale score of equal to or greater 4.
254. The method of embodiment 237, wherein the administering is maintained for at least 2, 4, or 8 weeks.
255. The method of embodiment 237, wherein the patient is aged 12 or older.
256. The method of embodiment 255, wherein the patient has a Body Surface Area (BSA) of atopic dermatitis involvement (excluding scalp) of 3% to 20% at baseline.
257. The method of embodiment 256 wherein the patient has an Investigator's Global Assessment score of 2 to 3 at baseline.
258. The method of embodiment 257, wherein the patient has been diagnosed with atopic dermatitis for at least 2 years.
259. The method of embodiment 258, wherein the patient is diagnosed with atopic dermatitis as defined by the Hanifin and Rajika criteria.
260. The method of embodiment 259, wherein the patient did not use topical treatments for atopic dermatitis, other than emollients, within 2 weeks of baseline.
261. The method of embodiment 238, wherein the cream formulation is an oil-in-water emulsion.
262. The method of embodiment 261, wherein the cream formulation is a solubilized cream.
263. The method of embodiment 262, wherein the cream formulation has a pH from about 2.8 to about 3.6.
264. A method of treating atopic dermatitis in a human patient, comprising administering to the skin of the human patient in need thereof, a cream formulation two times per day, wherein the cream formulation comprises 0.75% (w/w) on a free base basis of ruxolitinib, or a pharmaceutically acceptable salt thereof, wherein the patient:
is aged 12 years or older;
has an Investigator's Global Assessment score of 2 to 3 at baseline;
has a Body Surface Area of atopic dermatitis involvement (excluding scalp) of 3% to 20% at baseline; and
achieves an Investigator's Global Assessment score of 0 or 1 with an improvement of at least 2 points from baseline at week 8 of the administering.
265. A method of treating atopic dermatitis in a human patient, comprising administering to the skin of the human patient in need thereof, a cream formulation two times per day, wherein the cream formulation comprises 0.75% (w/w) on a free base basis of ruxolitinib, or a pharmaceutically acceptable salt thereof, wherein the patient:
is aged 12 years or older;
has an Investigator's Global Assessment score of 2 to 3 at baseline;
has a Body Surface Area of atopic dermatitis involvement (excluding scalp) of 3% to 20% at baseline; and
achieves a 75% improvement in Eczema Area and Severity Index score from baseline at week 8 of the administering.

The invention will be described in greater detail by way of specific examples. The following examples are offered for illustrative purposes, and are not intended to limit the invention in any manner. Those of skill in the art will readily recognize a variety of non-critical parameters, which can be changed or modified to yield essentially the same results. In some embodiments, the present disclosure provides pharmaceutical formulations comprising the components specified in the example formulations (e.g., Example 3), wherein the components are present in about the amounts in Tables 2-5.

EXAMPLES

Example 1

Preparation of Oil-In-Water Cream Formulations of Ruxolitinib (INCB018424) Phosphate First, in order to determine the solubility of ruxolitinib (free base) or its 1:1 phosphate salt, approximately 5 mL of a potential solvent was added to approximately 50 mg of the API or its salt at room temperature. The mixtures were suspended and rotated on a wheel. If the mixtures became clear solutions, more solid material was added. The suspensions were then suspended over 24 hours. The samples were filtered through 0.2 micron filters. The liquid portions were collected and diluted with 50/50 water methanol/water. The concentrations of the diluted samples were analyzed by HPLC. When the free base or salt was fairly insoluble, the results are approximate only.

TABLE 1

| Potential Solvent | Solubility of Phosphate Salt (mg/mL) | Solubility of Free Base (mg/mL) |
|---|---|---|
| Water | 2.7 | 2.0 |
| pH 4, citric buffer, 0.1M | 1.5 | 1.1 |
| pH 6, citric buffer, 0.1M | 0.2 | 0.15 |
| Ethanol | 7.3 | 5.5 |
| Isopropanol | 0.6 | 0.45 |
| Benzyl alcohol | 3 | 2.3 |
| Propylene glycol | 24 | 18.2 |
| PEG 200 | 23 | 17.4 |
| PEG 300 | 14 | 10.6 |
| Glycerin | 11 | 8.3 |
| Transcutol | 10 | 7.6 |
| Trolamine | 51 | 38.6 |
| Water/PEG 200 (50/50) | 23 | 17.4 |
| Water/glyercin (50/50) | 21 | 15.9 |
| Water/glycerin/trolamine (40/40/20) | 18 | 13.6 |
| Isopropyl myristate | <0.1 | 0.08 |
| Isosorbide dimethyl ether | 0.4 | 0.3 |
| Mineral oil | <0.1 | 0.08 |
| Olelyl alcohol | 0.1 | 0.08 |
| Dimethicone | <0.2 | 0.15 |
| $C_{12-15}$ alcohol benzoate | <0.2 | 0.15 |
| Caprylic triglyceride | <0.2 | 0.15 |

An oil-in-water cream formulation was prepared for 1:1 ruxolitinib phosphoric acid salt at 0.5, 1.0 and 1.5% by weight of the formulation (free base equivalent). The compositions for a 15 gram tube are provided in Table 2 below. The formulation for three strengths were identical except for adjustments to the purified water quantity based on the amount of active ingredient. All excipients used in the formulation were compendial grade (i.e., USP/NF or BP) or are approved for use in topical products.

The quantitative formulae for representative 400 kg batches of the cream formulation at 0.5, 1.0 and 1.5% are also provided in Tables 3, 4, and 5, respectively.

The oil-in-water cream formulations were synthesized according to the following procedure at either a 3.5 kg or 400 kg scale (when made at a 3.5 kg batch size, the amounts in Tables 3-5 were scaled appropriately). Some batches were subject to minor changes associated with scale-up, such as the size of mixing vessels and mixers. Generally, overhead mixer with high and low shear mixing blades are suitable for the process.

Procedure

1. A paraben phase was prepared by mixing methyl and propyl parabens with a portion of the propylene glycol (see % in Tables 2-5).

2. Next, a xanthan gum phase was prepared by mixing xanthan gum with propylene glycol (see % in Table 2-5).

3. An oil phase was then prepared by mixing light mineral oil, glyceryl stearate, polysorbate 20, white petrolatum, cetyl alcohol, stearyl alcohol, dimethicone and medium chain triglycerides. The phase is heated to 70-80° C. to melt and form a uniform mixture.

4. The aqueous phase was next prepared by mixing purified water, polyethylene glycol, and disodium EDTA. The phase is heated to 70-80° C.

5. The aqueous phase of step 4, paraben phase of step 1, and Example 2 (phosphate salt of API) were combined to form a mixture.

6. The xanthan gum phase from step 2 was then added to the mixture from step 5.

7. The oil phase from step 3 was then combined under high shear mixing with the mixture from step 6 to form an emulsion.

8. Phenoxyethanol was then added to the emulsion from step 7. Mixing was continued, and then the product was cooled under low shear mixing.

TABLE 2

| PHASE | FORMULA COMPONENT | Function | Percentage of Total (% w/w) | Grams/Tube |
|---|---|---|---|---|
| Paraben | Propylene Glycol USP | Solvent | 10.00 | 1.5 |
| | Methyl Paraben NF | Antimicrobial preservative | 0.10 | 0.015 |
| | Propyl Paraben NF | Antimicrobial preservative | 0.05 | 0.0075 |
| Xanthan Gum | Propylene Glycol USP | Solvent | 5.00 | 0.75 |
| | Xanthan Gum NF | Suspending, stabilizing, viscosity-increasing agent | 0.40 | 0.06 |
| Oil | Light Mineral Oil NF | Emollient, solvent | 4.00 | 0.6 |
| | Glyceryl Stearate SE | Emulsifier | 3.00 | 0.45 |
| | Polysorbate 20 NF | Emulsifying/stabilizing agent | 1.25 | 0.1875 |
| | White Petrolatum USP | Occlusive agent | 7.00 | 1.05 |
| | Cetyl Alcohol NF | Stiffening agent, consistency improver | 3.00 | 0.45 |
| | Stearyl Alcohol NF | Stiffening agent | 1.75 | 0.2625 |
| | Dimethicone 360 NF | Skin protectant | 1.00 | 0.15 |
| | Medium Chain Triglyceride NF | Emollient, solvent | 5.00 | 0.75 |

TABLE 2-continued

| PHASE | FORMULA COMPONENT | Function | Percentage of Total (% w/w) | Grams/Tube |
|---|---|---|---|---|
| Aqueous/ Active | Purified Water USP | Solvent | 50.24 – 48.92 | 7.536 – 7.338 |
| | Edetate Disodium USP | Chelating agent | 0.05 | 0.0075 |
| | Polyethylene Glycol USP | Solvent | 7.00 | 1.05 |
| Final | Example 2 * | Active | 0.66 – 1.98 | 0.099 – 0.297 |
| | Phenoxyethanol BP | Antimicrobial preservative | 0.50 | 0.075 |
| | Total | | 100.00% | 15 |

TABLE 3

| Ingredient | Kilograms | Percentage (w/w) |
|---|---|---|
| Ruxolitinib phosphate | 2.64 (phosphate salt)/ 2.0 (free base) | 0.66 (phosphate salt)/ 0.5 (free base) |
| Propylene Glycol USP | 40.0 | 10.00 |
| Methyl Paraben NF | 0.4 | 0.10 |
| Propyl Paraben NF | 0.2 | 0.05 |
| Propylene Glycol USP | 20.0 | 5.00 |
| Xanthan Gum NF | 1.6 | 0.40 |
| Light Mineral Oil NF | 16.0 | 4.00 |
| Glyceryl Stearate SE | 12.0 | 3.00 |
| Polysorbate 20 NF | 5.0 | 1.25 |
| White Petrolatum USP | 28.0 | 7.00 |
| Cetyl alcohol NF | 12.0 | 3.00 |
| Stearyl alcohol NF | 7.0 | 1.75 |
| Dimethicone 360 NF | 4.0 | 1.00 |
| Medium Chain Triglycerides NF | 20.0 | 5.00 |
| Purified Water USP (approximate) | 201 | 50.25 |
| Edetate Disodium USP | 0.2 | 0.05 |
| Polyethylene Glycol USP | 28.0 | 7.00 |
| Phenoxyethanol BP | 2.0 | 0.5 |
| Total (approximate) | 400.0 | 100 |

TABLE 4

| Ingredient | Kilograms | Percentage (w/w) |
|---|---|---|
| Ruxolitinib phosphate | 5.28 (phosphate salt)/ 4.0 (free base) | 1.32 (phosphate salt)/ 1.00 (free base) |
| Propylene Glycol USP | 40.0 | 10.00 |
| Methyl Paraben NF | 0.4 | 0.10 |
| Propyl Paraben NF | 0.2 | 0.05 |
| Propylene Glycol USP | 20.0 | 5.00 |
| Xanthan Gum NF | 1.6 | 0.40 |
| Light Mineral Oil NF | 16.0 | 4.00 |
| Glyceryl Stearate SE | 12.0 | 3.00 |
| Polysorbate 20 NF | 5.0 | 1.25 |
| White Petrolatum USP | 28.0 | 7.00 |
| Cetyl alcohol NF | 12.0 | 3.00 |
| Stearyl alcohol NF | 7.0 | 1.75 |
| Dimethicone 360 NF | 4.0 | 1.00 |
| Medium Chain Triglycerides NF | 20.0 | 5.00 |
| Purified Water USP (approximate) | 198.5 | 49.6 |
| Edetate Disodium USP | 0.2 | 0.05 |
| Polyethylene Glycol USP | 28.0 | 7.00 |
| Phenoxyethanol BP | 2.0 | 0.5 |
| Total (approximate) | 400.0 | 100 |

TABLE 5

| Ingredient | Kilograms | Percentage (w/w) |
|---|---|---|
| Ruxolitinib phosphate | 7.92 (phosphate salt)/ 6.0 (free base) | 1.98 (phosphate salt)/ 1.5 (free base) |
| Propylene Glycol USP | 40.0 | 10.00 |
| Methyl Paraben NF | 0.4 | 0.10 |
| Propyl Paraben NF | 0.2 | 0.05 |
| Propylene Glycol USP | 20.0 | 5.00 |
| Xanthan Gum NF | 1.6 | 0.40 |
| Light Mineral Oil NF | 16.0 | 4.00 |
| Glyceryl Stearate SE | 12.0 | 3.00 |
| Polysorbate 20 NF | 5.0 | 1.25 |
| White Petrolatum USP | 28.0 | 7.00 |
| Cetyl alcohol NF | 12.0 | 3.00 |
| Stearyl alcohol NF | 7.0 | 1.75 |
| Dimethicone 360 NF | 4.0 | 1.00 |
| Medium Chain Triglycerides NF | 20.0 | 5.00 |
| Purified Water USP (approximate) | 195.5 | 48.9 |
| Edetate Disodium USP | 0.2 | 0.05 |
| Polyethylene Glycol USP | 28.0 | 7.00 |
| Phenoxyethanol BP | 2.0 | 0.5 |
| Total (approximate) | 400.0 | 100 |

More consistent batches at larger scales (e.g., 140 kg) could be obtained by adding ruxolitinib phosphate gradually to the aqueous phase and then combining with the other phases. Similarly, more consistent batches could be obtained by slower cooling (e.g., by using room temperature water in the outer jacket of the reactor, rather than lower temperature water.

Table 5A shows the 0.75% and 1.5% ruxolitinib cream formulation used in Example 3.

TABLE 5A

| | 0.75% Cream | | 1.5% Cream | |
|---|---|---|---|---|
| Component | wt % | g per 60 g tube | wt % | g per 60 g tube |
| Ruxolitinib Phosphate | 0.99 (0.751)) | 0.594 | 1.98 (1.50[b]) | 1.188 |
| Propylene Glycol | 15.0 | 9.00 | 15.0 | 9.00 |
| Methylparaben | 0.10 | 0.06 | 0.10 | 0.06 |
| Propylparaben | 0.05 | 0.03 | 0.05 | 0.03 |
| Xanthan Gum | 0.40 | 0.24 | 0.40 | 0.24 |
| Light Mineral Oil | 4.00 | 2.40 | 4.00 | 2.40 |
| Glyceryl Stearate SE | 3.00 | 1.80 | 3.00 | 1.80 |
| Polysorbate 20 | 1.25 | 0.75 | 1.25 | 0.75 |
| White Petrolatum | 7.00 | 4.20 | 7.00 | 4.20 |
| Cetyl Alcohol | 3.00 | 1.80 | 3.00 | 1.80 |
| Stearyl Alcohol | 1.75 | 1.05 | 1.75 | 1.05 |
| Dimethicone 360 | 1.00 | 0.60 | 1.00 | 0.60 |

TABLE 5A-continued

|  | 0.75% Cream | | 1.5% Cream | |
|---|---|---|---|---|
| Component | wt % | g per 60 g tube | wt % | g per 60 g tube |
| Triglycerides, Medium Chain | 5.00 | 3.00 | 5.00 | 3.00 |
| Purified Water | 49.91 | 29.95 | 48.92 | 29.36 |
| Edetate Disodium | 0.05 | 0.03 | 0.05 | 0.03 |
| Polyethylene Glycol 200 | 7.00 | 4.20 | 7.00 | 4.20 |
| Phenoxyethanol | 0.50 | 0.30 | 0.50 | 0.30 |
| Total | 100% | 60 g | 100% | 60 g |

The batches were tested for stability at 25° C. and found to be stable up to 24 months with a pH consistent with the pH range described supra (see Table 7, 9, 11, 12, 13, 15, 17, and 19 in U.S. Patent Publ. No. 2015/0250790, which is incorporated herein by reference in its entirety). The viscosity of the cream formulations (e.g., containing 0.75% or 1.5% ruxolitinib phosphate on a free base basis) had a viscosity of ≥17,000 cPs on release and a shelf-life viscosity of ≥10,000 cPs.

Example 2

Phase 2, Randomized, Dose-Ranging, Vehicle-Controlled and Triamcinolone 0.1% Cream—Controlled Study to Evaluate the Safety and Efficacy of Ruxolitinib (INCB018424) Phosphate Cream Applied Topically to Adults with Atopic Dermatitis This was a randomized, vehicle- and active (triamcinolone 0.1% cream)-controlled study in subjects with mild to moderate atopic dermatitis (AD). The study was double-blinded for vehicle, ruxolitinib cream doses, and active control. 307 subjects were randomized 1:1:1:1:1:1 to 1.5% ruxolitinib cream BID, 1.5% ruxolitinib cream QD, 0.5% ruxolitinib cream QD, 0.15% ruxolitinib cream QD, vehicle BID, and active control (triamcinolone 0.1% cream BID) and stratified by EASI score (≤7 and >7). The ruxolitinib in the ruxolitinib cream was present as ruxolitinib phosphate with the percentages as % w/w on a free base basis. The ruxolitinib cream formulations were oil-in-water cream formulations prepared as described in Example 1 (see also U.S. Patent Publ. No. 2015/0250790), which is incorporated herein by reference in its entirety.

Subjects receiving QD regimens applied vehicle at the evening application. Subjects received blinded study drug for 8 weeks. Subjects were randomized to triamcinolone applied triamcinolone 0.1% cream BID for 4 weeks and vehicle cream for 4 weeks to not exceed the allowable triamcinolone application duration.

1.5% ruxolitinib cream, 0.5% ruxolitinib cream, and 0.15% ruxolitinib cream were supplied and applied topically as a thin film to the affected areas in the morning and in the evening at least 1 hour before bedtime. For each 1% of BSA (palm with fingers) to be treated with study drug, approximately 2 inches (5 cm) of study drug were used. Subjects were to be advised to limit use to no more than 1 tube per application. If sunscreen, makeup, or other cream were to be applied to the areas to be treated, subjects were to be instructed to wash the treatment areas with mild soap and water and pat dry before application of study drug. If used, topical anti infectives or other topical treatments were to be avoided for at least 1 hour before and after application of study drug to an area. Subjects were to be cautioned to avoid excessive exposure to either natural or artificial sunlight (including tanning booths, sun lamps, etc.) and, when outdoors, were to be advised to wear loose-fitting clothing that protects the treated area from the sun.

Vehicle cream was matching in appearance to the ruxolitinib creams, except it did not contain active drug. Vehicle cream and triamcinolone 0.1% cream were applied in the same manner as ruxolitinib cream. Triamcinolone 0.1% cream treatment of 4 weeks was followed by vehicle treatment for 4 weeks. Subjects receiving QD regimens of ruxolitinib cream received vehicle cream at the evening application.

At Week 8, subjects who meet criteria received open-label treatment with 1.5% ruxolitinib cream BID for 4 weeks.

Subjects who developed additional areas of AD after the initiation of treatment were allowed to treat these additional areas (except the face and intertriginous areas) provided the total treated BSA did not exceed 20% and there are no safety concerns regarding the additional application of study drug.

The study population were men or women, aged 18 to 70 years, who had been diagnosed with atopic dermatitis (AD) for at least 2 years, with an Investigator's Global Assessment (IGA) score of 2 to 3, and body surface area (BSA) involvement (excluding the face and intertriginous areas) of 3% to 20%.

Subjects who met all of the following key inclusion criteria could be included in the study: (i) men and women aged 18 to 70 years, inclusive; (ii) diagnosed with AD as defined by the Hanifin and Rajka criteria; (iii) history of AD for at least 2 years; (iv) an IGA score of 2 to 3 at screening and baseline; (v) BSA of AD involvement, excluding the face and intertriginous areas, of 3% to 20% at screening and baseline; and (vi) agreement to discontinue all agents used to treat AD from screening through the final follow up visit.

Subjects who met any of the following key exclusion criteria were excluded from the study: (i) evidence of active acute or chronic infections; (ii) use of topical treatments for AD (other than bland emollients) within 2 weeks of baseline; (iii) use of systemic immunosuppressive or immunomodulating drugs (e.g., oral or injectable corticosteroids, methotrexate, cyclosporine, mycophenolate mofetil, azathioprine) within 4 weeks or 5 half-lives of baseline (whichever is longer); (iv) subjects with other dermatologic disease besides AD whose presence or treatments could complicate the assessment of disease (e.g., psoriasis); (v) a history of other diseases besides dermatologic disorders (e.g., other autoimmune diseases) taking treatments that could complicate assessments; (vi) subjects with cytopenias at screening, defined as leukocytes <3.0×10$^9$/L, neutrophils <lower limit of normal, hemoglobin <10 g/dL. Lymphocytes <0.8×109/L, platelets <100×109/L; (vii) subjects with severely impaired liver function (Child-Pugh Class C) or end-stage renal disease on dialysis or at least 1 of the following: serum creatinine >1.5 mg/dL, alanine aminotransferase or aspartate aminotransferase ≥1.5× upper limit of normal; (viii) subjects taking potent systemic cytochrome P450 3A4 inhibitors or fluconazole within 2 weeks or 5 half-lives, whichever is longer, before the baseline visit (topical agents with limited systemic availability are permitted); and (ix) subjects who have previously received Janus kinase inhibitors, systemic or topical (e.g., ruxolitinib, tofacitinib, baricitinib, filgotinib, lestaurtinib, or pacritinib).

The primary endpoint of the study was the percentage change from baseline in EASI score at Week 4 in subjects treated with 1.5% ruxolitinib cream BID compared with subjects treated with vehicle cream BID.

Secondary endpoints included the mean percentage change from baseline in EASI score at Week 4 in subjects treated with ruxolitinib cream compared with subjects treated with vehicle cream BID; the mean percentage change from baseline in EASI score at Week 4 in subjects treated with ruxolitinib cream compared with subjects treated with triamcinolone 0.1% cream BID; the mean percentage change from baseline in EASI score at Week 2 and Week 8; the proportion of subjects who achieve a ≥50% improvement from baseline in EASI (EASI-50) at Weeks 2, 4, and 8; assessment of dose response based on percentage change from baseline in EASI score at Week 4; time to achieve EASI-50; proportion of subjects achieving IGA score of 0 to 1 who have an improvement of ≥2 points from baseline at Weeks 2, 4, and 8; the mean change from baseline in the Itch Numerical Rating Scale (NRS) score at Weeks 2, 4, and 8; and safety and tolerability assessed by monitoring the frequency, duration, and severity of adverse events (AEs); performing physical examinations; collecting vital signs; and collecting laboratory data for hematology, serum chemistry, and urinalysis.

Other secondary endpoints included change from baseline in quality of life based on the Skindex-16 (overall, each question, and specified groupings) at Weeks 2, 4, 8, 10, and 12. Skindex-16 (Atherton PJ, et al, *Support Care Cancer*. 2012 August; 20(8): 1729-1735) is a 16-question quality-of-life assessment that asks how much the subject has been bothered by various aspects of their skin condition during the past week. Patients answered questions regarding the effect of various AD symptoms during the past week on a scale of 0 (never bothered) to 6 (always bothered). Patients were assessed at baseline and Weeks 2, 4, 8, 10, and 12.

Results

Patient demographics are shown in Table 6. Baseline clinical characteristics are shown in Table 7. Skindex-16 overall score was 3.7±1.3 at baseline.

TABLE 6

| Demographic | Total (N = 307) |
|---|---|
| Age, median (range), years | 35.0 (18.0-70.0) |
| Female, n (%) | 168 (54.7) |
| Race, n (%) | |
| White | 172 (56.0) |
| Black | 85 (27.7) |
| Asian | 41 (13.4) |
| Other | 9 (2.9) |

TABLE 7

| Clinical Characteristic | Total (N = 307) |
|---|---|
| BSA, mean ± SD, % | 9.6 ± 5.4 |
| Baseline EASI, mean ± SD | 8.4 ± 4.7 |
| ≤7, n (%) | 147 (47.9) |
| ≤7, n (%) | 159 (51.8) |
| Missing, n (%) | 1 (0.3) |
| Baseline IGA, n (%) | |
| 2 | 95 (31) |
| 3 | 210 (69) |
| Itch NRS score, * mean ± SD | 6.0 ± 2.1 |
| Duration of disease, median (range), years | 20.8 (0.1-66.1) |
| Number of flares in last 12 months, mean ± SD | 7.3 ± 23.3 |

In Figures showing a triamcinolone result, the triamcinolone (TAC) arm received 0.1% triamcinolone cream through Week 4 and vehicle thereafter.

Figure 2:
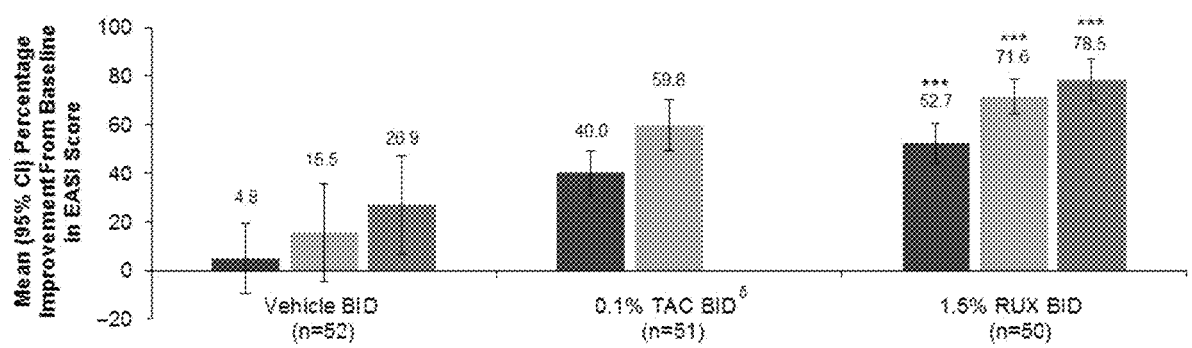
FIG. 2 shows a graph of mean percentage improvement from baseline in EASI scores for vehicle (BID), triamcinolone (0.1% BID), and ruxolitinib cream (1.5% BID) at week 2 (first graph bar of each set), week 4 (second graph bar of each set) and week 8 (third graph bar of each set). 0.1% TAC does not show a bar because TAC was only administered for 4 weeks.

As shown in FIG. 1, ruxolitinib cream showed significant improvement of EASI scores in a dose- and time-dependent manner across all concentrations compared to vehicle control. As shown in FIG. 2, 1.5% ruxolitinib cream showed the highest efficacy among all treatment arms (across all efficacy endpoints), while 1.5% ruxolitinib cream BID demonstrated noninferiority to triamcinolone (TAC) in EASI scores (Weeks 2 and 4) with numerically greater rates of improvement.

Further, increasing numbers of patients achieved EASI-75 (at least a 75% improvement in EASI from baseline) in a dose- and time-dependent manner (see FIG. 3) with more patients achieving EASI-75 with 1.5% ruxolitinib cream BID at week 4 than with 0.1% TAC.

Figure 4:
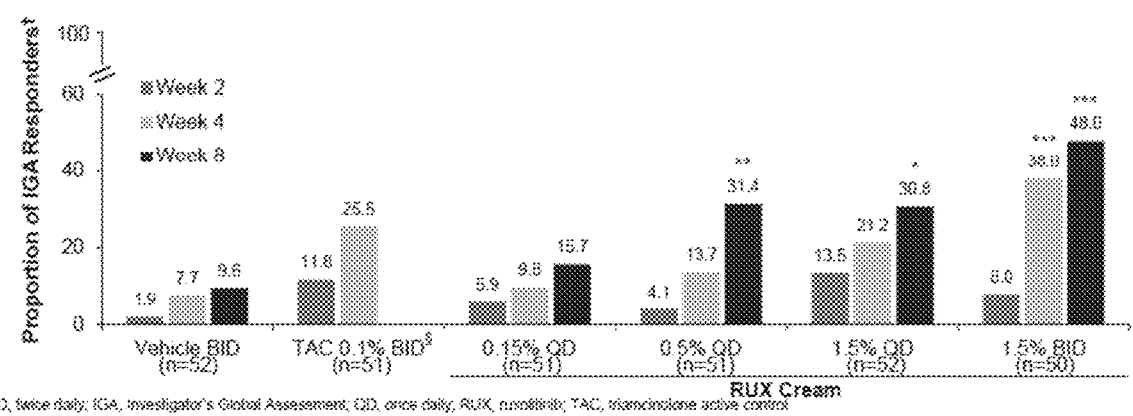
FIG. 4 shows a graph of proportion of IGA response (a responder was a patient achieving an IGA score of 0-1 with an improvement of ≥2 points from baseline) for vehicle (BID), triamcinolone (0.1% BID), and ruxolitinib cream (0.15% QD, 0.5% QD, 1.5% QD, and 1.5% BID) at week 2 (first graph bar of each set), week 4 (second graph bar of each set) and week 8 (third graph bar of each set). 0.1% TAC does not show a bar because TAC was only administered for 4 weeks.

As shown in FIG. 4, ruxolitinib cream demonstrated significant improvement in IGA response (an IGA responder was a patient achieving an IGA score of 0-1 with an improvement of ≥2 points from baseline) in a dose- and time-dependent manner. Further, 1.5% ruxolitinib cream BID showed significantly more IGA responders vs. vehicle at weeks 4 and 8 (FIG. 4) and greater response than 0.1% TAC at week 4.

Figure 5:
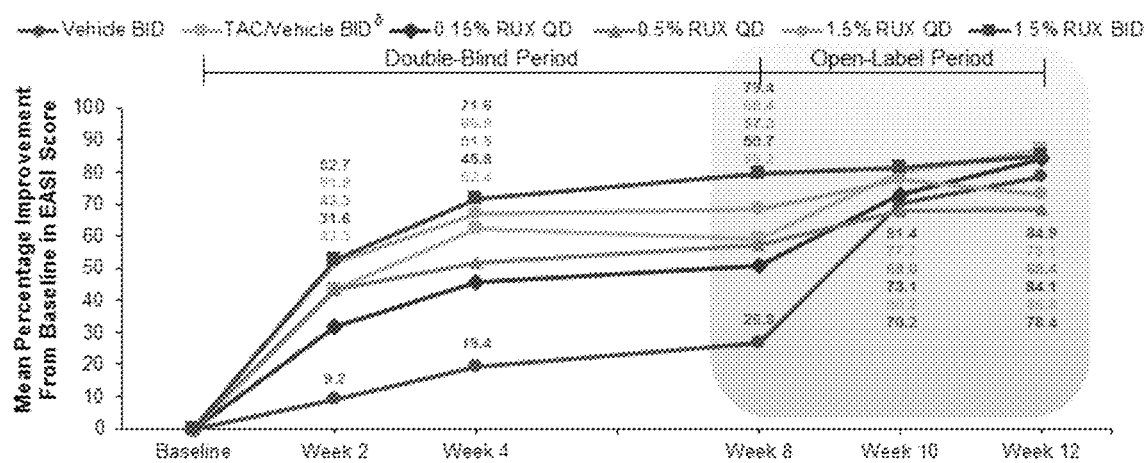
FIG. 5 shows a graph of mean percentage improvement from baseline in EASI scores for vehicle, triamcinolone, and ruxolitinib cream in 12 weeks. The open-label period was from week 8 to week 12, wherein 1.5% ruxolitinib cream was administered.
Figure 6:
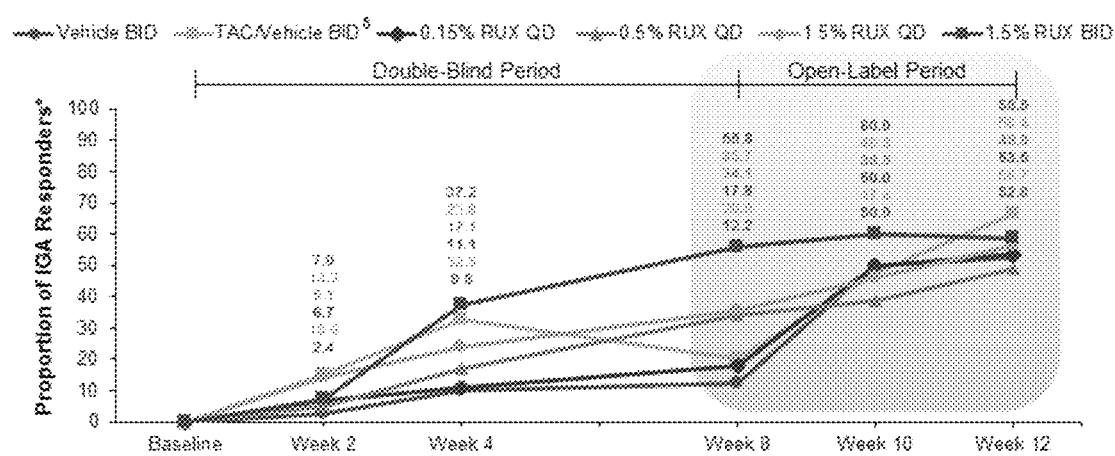
FIG. 6 shows a graph of proportion of IGA response for vehicle, triamcinolone, and ruxolitinib cream in 12 weeks. The open-label period was from week 8 to week 12, wherein 1.5% ruxolitinib cream was administered.

As shown in FIG. 5, transitioning to 1.5% ruxolitinib cream BID at week 8 was associated with substantial improvement in EASI scores. Similarly, switching to 1.5% ruxolitinib cream BID at week 8 was associated with substantial improvement in all treatment arm in IGA response (see FIG. 6).

Figure 7:
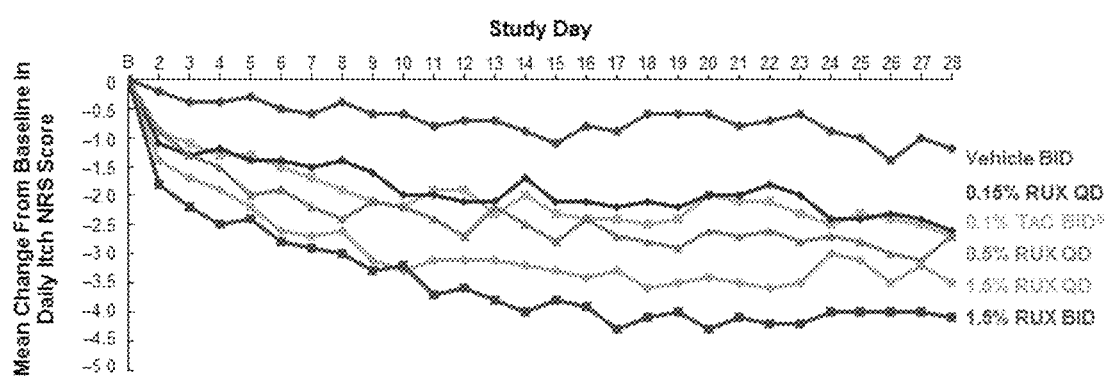
FIG. 7 shows a graph of mean change from baseline in daily itch NRS scores (NRS score has a range of 0-10 with 0 being no itch and 10 being the worst possible itch) for vehicle (BID), triamcinolone (0.1% BID), and ruxolitinib cream (0.15% QD, 0.5% QD, 1.5% QD, and 1.5% BID) in 28 days.
Figure 8:
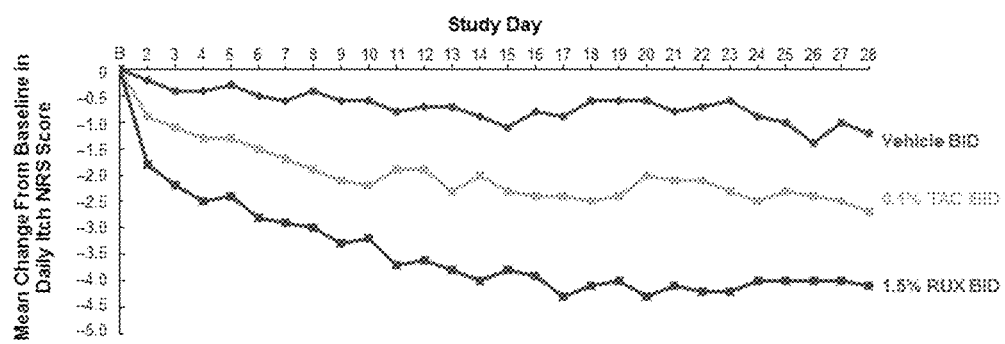
FIG. 8 shows a graph of mean change from baseline in daily itch NRS scores for vehicle (BID), triamcinolone (0.1% BID), and ruxolitinib cream (1.5% BID) in 28 days.
Figure 9:
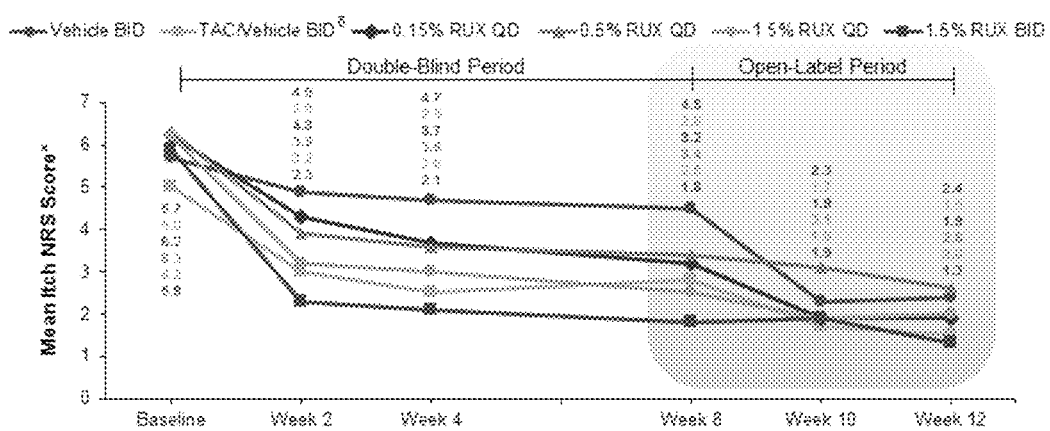
FIG. 9 shows a graph of mean itch NRS scores for vehicle, triamcinolone, and ruxolitinib cream in 12 weeks. The open-label period was from week 8 to week 12, wherein 1.5% ruxolitinib cream was administered.

Further, as shown in FIG. 7, ruxolitinib cream was associated with a rapid and sustained reduction in itch NRS scores (NRS score has a range of 0-10 with 0 being no itch and 10 being the worst possible itch). In particular, as shown in FIG. 8 and Table 8, significant reductions in itch NRS scores were observed with 1.5% ruxolitinib cream BID within 36 hours of first application (i.e., after 2 days) vs. vehicle (−1.8 vs. 0.2; p<0.0001). Further, as shown in FIG. 9 and Table 8, transitioning to 1.5% ruxolitinib cream BID at week 8 was associated with additional and sustained improvement in itch.

Clinically meaningful reductions in itch NRS scores were observed within 36 hours after first application of 1.5% ruxolitinib cream BID versus vehicle (−1.8 vs −0.2; P<0.0001). Decreases in itch NRS scores noted within the first 2 weeks of treatment for all ruxolitinib cream regimens were sustained through the double-blind period. At Week 4, both 1.5% ruxolitinib cream regimens produced a more pronounced alleviation in itch (mean percent change from baseline, −64.6 for 1.5% BID and −54.0 for 1.5% QD) compared with triamcinolone (−50.3); the difference was statistically significant for 1.5% ruxolitinib BID versus triamcinolone by mean change from baseline (−4.0 vs −2.5, respectively; P=0.003). Improvements from baseline in itch NRS scores were treatment regimen dependent, with 68.5% mean improvement in patients treated with 1.5% ruxolitinib cream BID at Week 8, which was significantly better than vehicle (17.6%; P<0.0001).

In patients eligible for CRI analysis (baseline itch NRS of ≥4; n=232), a considerably higher proportion of patients on ruxolitinib cream achieved CRI response after just a single day of therapy than those on vehicle (Day 2 response rates for 1.5% ruxolitinib cream BID vs vehicle, 10.5% vs 2.9%); Day 4 response rates for 1.5% ruxolitinib cream BID and vehicle were 26.3% and 2.9, respectively (P<0.05). At Week 2, significantly more patients achieved CRI with 1.5% ruxolitinib BID (47.5%; P<0.001), 1.5% ruxolitinib QD (32.4%; P<0.01), and 0.5% ruxolitinib QD (25.0%; P<0.05) versus vehicle (5.4%; FIG. 1). Response rates observed with 1.5% ruxolitinib cream BID at Week 2 were also significantly higher compared with triamcinolone (19.4%, P<0.05). Cumulative incidence rates for time to first CRI response were substantially higher in all ruxolitinib cream groups (log-rank P<0.001) versus vehicle. Shorter median time to first response was noted in 1.5% ruxolitinib cream BID and QD treatment groups (8 and 12.5 days, respectively) versus vehicle (response not reached).

Similarly, among patients eligible for MCID analysis (baseline itch NRS of ≥2; n=272), higher rates of MCID were observed as early as Day 2 (within 36 hours of treatment initiation) with 1.5% ruxolitinib cream BID (42.5%; P<0.01) and QD (37.2%; P<0.05) versus vehicle (13.6%); significantly higher rates of MCID were also observed for 1.5% ruxolitinib cream BID compared with triamcinolone at Day 2 (20.5%; P<0.05).

Strikingly, reductions in itch with ruxolitinib cream in the study appeared greater via indirect comparison than reported improvement in patients treated with dupilumab in phase 3 trials for patients with moderate-to-severe AD, although baseline itch NRS scores were slightly higher in dupilumab studies (Simpson EL, et al. "Two phase 3 trials of dupilumab versus placebo in atopic dermatitis," *N Engl J Med* 2016; 375:2335-48).

Itch NRS scores and Skindex-16 scores were correlated at baseline. Reduction in itch was positively associated with decreased QoL burden (Pearson correlation, 0.67; P<0.001).

TABLE 8

| Time Point | Mean itch NRS score (1.5% ruxolitinib cream BID) | Change in mean itch NRS score from baseline (1.5% ruxolitinib cream BID) | Mean itch NRS score (vehicle) | Mean itch NRS score (vehicle arm transitioned to 1.5% ruxolitinib cream at week 8) |
|---|---|---|---|---|
| Baseline | 5.9 |  | 5.7 | — |
| 2 Weeks | 2.3 | −3.6 | 4.9 | — |
| 4 Weeks | 2.1 | −3.8 | 4.7 | — |
| 8 Weeks | 1.8 | −4.1 | 4.5 | — |
| 10 Weeks | 1.9 | −4 | — | 2.3 |
| 12 Weeks | 1.3 | −4.6 | — | 2.4 |

Figure 10:
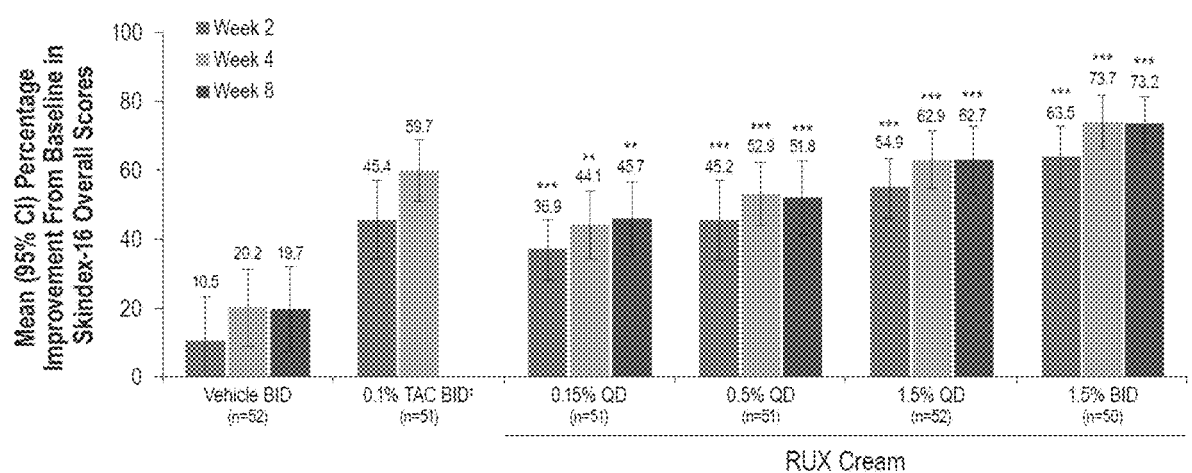
FIG. 10 shows a graph of mean percentage improvement from baseline in Skindex-16 overall score for vehicle (BID), triamcinolone (0.1% BID), and ruxolitinib cream (0.15% QD, 0.5% QD, 1.5% QD, and 1.5% BID) at week 2 (first graph bar of each set), week 4 (second graph bar of each set) and week 8 (third graph bar of each set). 0.1% TAC does not show a bar because TAC was only administered for 4 weeks.  indicates P<0.01 vs vehicle; * indicates P<0.001 vs vehicle. † indicates TAC arm received 0.1% TAC cream through Week 4 and vehicle thereafter.

Significant improvements in QoL were noted for all ruxolitinib cream regimens. The improvements were treatment regimen-dependent (FIG. 10). Mean percentage improvement from baseline in Skindex-16 overall scores in patients treated with 1.5% ruxolitinib cream BID was 63.5% at Week 2 (vehicle, 10.5%; P<0.001) and 73.2% at Week 8 (vehicle, 19.7%; P<0.001). At Week 4, the mean percentage improvement in overall score was significantly greater with 1.5% ruxolitinib cream BID (73.7%; P=0.02) compared with triamcinolone (59.7%). Itch NRS scores and Skindex-16 scores were correlated at baseline. Reduction in itch was positively associated with decreased QoL burden (Pearson correlation, 0.67; P<0.001).

As shown in Table 9 (double blind period), ruxolitinib cream was well tolerated and no associated with clinically significant site reaction either in double-blind and open-label periods. There were no serious treatment emergent adverse events (TEAEs) or discontinuations due to TEAEs during the open-label period. All treatment-related adverse events were mild or moderate in severity.

TABLE 9

| | Safety in the Open-Label Period by Initial Treatment Group | | | | | |
|---|---|---|---|---|---|---|
| | Vehicle BID (n = 41) | 0.1% TAC BID (n = 40) | 0.15% RUX QD (n = 45) | 0.5% RUX QD (n = 41) | 1.5% RUX QD (n = 42) | 1.5% RUX BID (n = 43) |
| Days in study, median (range) | 28.0 (0-66.0) | 28.0 (12-38.0) | 28.0 (10.0-51.0) | 28.0 (13.0-40.0) | 28.0 (20.0-36.0) | 28.0 (50.0-106.0) |
| Patients with TEAE, n (%) | 5(12.2) | 11 (27.5) | 11 (24.2) | 8 (19.5) | 11 (26.2) | 17 (39.5) |
| Most common TEAEs* | | | | | | |
| Nasopharyngitis | 1(2.4) | 1 (2.5) | 4 (8.9) | 1 (2.4) | 2 (4.8) | 4 (9.3) |
| Upper respiratory tract infection | 1(2.4) | 2 (5.0) | 0 | 1 (2.4) | 2 (4.8) | 1 (2.3) |
| AD | 1(2.4) | 1 (2.5) | 0 | 0 | 1 (2.4) | 1 (2.3) |
| Headache | 0 | 0 | 1 (2.2) | 1 (2.4) | 0 | 2 (4.7) |
| Treatment-relatedTEAE, n (%) | 0 | 0 | 0 | 1 (2.4) | 1 (2.4) | 2 (4.7) |

TEAE, treatment emergent adverse event.
*Occurring in >1% of the total patient population.

In summary, ruxolitinib cream demonstrated improvement in EASI score, IGA response, and itch NRS score in a dose- and time-dependent manner. Responses to 1.5% ruxolitinib cream BID in the double-blind period were sustained in the open-label period (at Week 12: mean 84.9% improvement from baseline in EASI score; 58.5% IGA responders). Patients who crossed over to 1.5% ruxolitinib cream BID in the open-label period experienced substantial improvements. The 1.5% ruxolitinib cream BID regimen brought about a prompt and sustained relief in itch that was significantly greater than that of triamcinolone at Week 4. Finally, ruxolitinib cream was well tolerated with no serious TEAEs related to the study drug and no patients discontinued because of TEAEs.

Example 3

Two Phase 3, Double-Blind, Randomized, 8-Week, Vehicle-Controlled Efficacy and Safety Studies of Ruxolitinib Cream Followed by a Long-Term Safety Extension Period in Adolescents and Adults With Atopic Dermatitis Two randomized, vehicle-control (VC) study were conducted in adolescent and adult (≥12 years old) participants with AD eligible for topical therapy. Approximately 600 participants were randomized in each study 2:2:1 to ruxolitinib 0.75% cream BID, ruxolitinib 1.5% cream BID, or vehicle cream. In addition, approximately 20% of the overall study population consisted of adolescents. Participants with baseline IGA score of 2 constituted approximately 25% of the overall study population. Participants with AD involvement of 3% to 20% BSA and IGA score of 2 to 3 received blinded study treatment for 8 weeks.

The ruxolitinib in the creams is present as ruxolitinib phosphate and the percentages are % (w/w) on a free base basis. The ruxolitinib cream formulations were oil-in-water cream formulations prepared as described in Example 1 (see Table 5 of U.S. Patent Publ. No. 2015/0250790; the 0.75% ruxolitinib cream was made by the method in Example 1 by adjusting for the mass of the API in the formulation with water), which is incorporated herein by reference in its entirety.

For participants who met all study inclusion criteria and none of the exclusion criteria, study drug assignment was obtained. Key entry criteria for participants to be eligible for the 8-week VC treatment period was a diagnosis of AD (as defined by the Hanifin and Rajka criteria) with a duration of disease for at least 2 years, IGA score of 2 to 3, and a % BSA involvement of 3% to 20% (excluding scalp) at screening and baseline.

Participants who developed additional areas of AD were allowed to treat these additional areas with approval by the investigator as long as the total treated BSA did not exceed 20%, and there were no safety concerns regarding the additional application of study drug. Approval to treat additional areas was to occur via telephone during the VC period, although the investigator, at his/her discretion, could ask the participant to return for an unscheduled visit. Through Week 8, participants continued to treat areas identified for treatment at baseline even if the areas began to improve.

At Week 8, the study's primary endpoint, participants were assessed for efficacy with a percentage of participants achieving a treatment response in IGA score. Participants were also assessed for safety and tolerability by monitoring the frequency, duration, and severity of AEs; performing physical examinations; and collecting vital signs and clinical/laboratory assessments at various timepoints during the study.

Participants who completed Week 8 assessments with no additional safety concerns will be offered to continue into the long-term safety (LTS) period with the same treatment regimen, except for those initially on vehicle, who will be equally assigned at Week 8 to 1 of the 2 active treatment groups. At that time, the IGA score required for the participants to enter the LTS period is 0 to 4. With regard to % BSA, there is no required lower limit; participants may have BSA in the range of 0% to 20%.

In the LTS period, participants will have study visits every 4 weeks until the end of the study (52 weeks total). At those visits, AD lesions will be evaluated by the investigator to confirm if the participant still requires continuation of therapy (IGA ≥1) or can otherwise (re)enter the observation/no treatment cycle (IGA=0).

During the LTS period (i.e., after the Week 8 visit), participants will self-evaluate recurrence of AD and will treat areas of the skin with active AD changes (not to exceed 20% BSA). If lesions clear between study visits, participants will stop treatment applications 3 days after they have disappeared. Participants will restart treatment of their AD at the first sign of recurrence. In the event that new lesions are outside of the usual location and/or are more wide spread than at baseline, the participant is required to contact the site for approval.

Participants will be on study for a duration of up to 60 weeks (28 days screening, 8 weeks of treatment in the VC period, 44 weeks of treatment in the LTS period, and a 30 (+7)-day safety follow-up.

The primary endpoint of the study was the proportion of patients achieving IGA-TS at Week 8. The key secondary endpoints of the study were: (i) the proportion of participants who achieve EASI-75 at Week 8; (ii) the proportion of participants with a ≥4 point improvement in itch NRS score from baseline at Week 8; and (iii) the proportion of participants with a clinically meaningful improvement in the PROMIS Short Form—Sleep Disturbance (8b) 24-hour recall score at Week 8.

Other secondary endpoints included: (i) the frequency, duration, and severity of adverse events; performing physical examinations; collecting vital signs; and collecting laboratory data for hematology, serum chemistry, and urinalysis; (ii) proportion of participants achieving an IGA-TS at Weeks 2 and 4; (iii) proportion of participants achieving an IGA of 0 or 1 at each visit; (iv) proportion of participants with a ≥4 point improvement in Itch NRS score from baseline to Weeks 2 and 4; (v) proportion of participants who achieve EASI50 at each visit during the VC period; (vi) proportion of participants who achieve EASI75 at Weeks 2 and 4; (vii) proportion of participants who achieve EASI90 at each visit during the VC period; (viii) mean percentage change from baseline in EASI score at each visit during the VC period; (ix) mean percentage change from baseline in SCORAD score at each visit during the VC period; (x) change from baseline in Itch NRS score at each visit during the VC period; (xi) time to achieve Itch NRS score improvement of at least 2, 3, or 4 points; (xii) change from baseline in Skin Pain NRS score at each visit during the VC period; (xiii) proportion of participants with a clinically meaningful improvement in the PROMIS Short Form—Sleep-Related Impairment (8a) 24-hour recall score at Weeks 2, 4, and 8; (xiv) change from baseline in PROMIS Short Form—Sleep Related Impairment (8a) 24-hour recall and Short Form—Sleep Disturbance (8b) 24-hour recall score at Weeks 2, 4, and 8; (xv) PROMIS Short Form—Sleep-Related Impairment (8a) 7 day recall and Short Form—Sleep Disturbance (8b) 7 day recall score at Weeks 8, 12, 24, and 52; (xvi) change from baseline in AD afflicted % BSA at every visit; (xvii) change from baseline in POEM score at each visit; (xviii) change from baseline in DLQI score at Weeks 2, 4, 8, 12, 24, and 52 and at unscheduled visits; (xix) mean PGIC score at Weeks 2, 4, and 8; (xx) proportion of participants with each score on the PGIC at Weeks 2, 4, and 8; (xxi) proportion of participants with a score of either 1 or 2 on the PGIC at Weeks 2, 4, and 8; (xxii) change from baseline in EQ-5D-5L score during the VC period; (xxiii) change from baseline in WPAI-SHP v2.0 at Weeks 2, 4, 8, 12, 24, 36, and 52; (xxiv) trough plasma concentrations of ruxolitinib at all study visits.

Subjects who met all of the following key inclusion criteria are eligible to be included in the study: (i) adolescents aged ≥12 to 17, inclusive, and men and women aged ≥18 years; (ii) diagnosed with AD as defined by the Hanifin and Rajka criteria; (iii) history of AD for at least 2 years; (iv) for the vehicle-control period, an IGA score of 2 to 3 at screening and baseline; for the long-term safety period, an IGA score of 0 to 4; (v) for the vehicle-control period, % BSA of AD involvement, excluding the scalp, of 3% to 20% at screening and baseline; for the long-term safety period, % BSA of AD involvement, excluding scalp, of 0% to 20%; (vi) agreement to discontinue all agents used to treat AD from screening through the final follow up visit; (vi) having at least 1 target lesion (which is representative of the participant's disease state and not present on the hands, feet or genitalia) that measures about 10 cm$^2$ or more at screening and baseline; (vii) willingness to avoid pregnancy or fathering of children based on specified criteria; and (viii) ability to comprehend and willingness to sign informed consent form or written informed consent from parent(s) or legal guardian and written assent from participants when possible.

Subjects who met any of the following key exclusion criteria were excluded from the study: (i) Participants who have an unstable course of AD (spontaneously improving or rapidly deteriorating) as determined by the investigator in the 4 weeks prior to baseline; (ii) Participants with concurrent conditions and history of other diseases: (a) Immunocompromised (e.g., lymphoma, acquired immunodeficiency syndrome, Wiskott-Aldrich syndrome); (b) chronic or acute infection requiring treatment with systemic antibiotics, antivirals, antiparasitics, antiprotozoals, or antifungals within 2 weeks before baseline; (c) active acute bacterial, fungal, or viral skin infection (e.g., herpes simplex, herpes zoster, chicken pox) within 1 week before baseline; (d) any other concomitant skin disorder (e.g., generalized erythroderma such as Netherton syndrome), pigmentation, or extensive scarring that, in the opinion of the investigator, may interfere with the evaluation of AD lesions or compromise participant safety; (e) presence of AD lesions only on the hands or feet without prior history of involvement of other classical areas of involvement such as the face or the folds; (f) other types of eczema; (iii) participants with any serious illness or medical, physical, or psychiatric condition(s) that, in the investigator's opinion, would interfere with full participation in the study, including administration of study drug and attending required study visits; pose a significant risk to the participant; or interfere with interpretation of study data. For example: (a) clinically significant or uncontrolled cardiac disease, including unstable angina, acute myocardial infarction within 6 months from Day 1 of study drug administration, New York Heart Association Class III or IV congestive heart failure, and arrhythmia requiring therapy or uncontrolled hypertension (blood pressure >150/90 mmHg) unless approved by medical monitor/sponsor; (b) participants with a history of malignancy in the 5 years preceding enrollment into this study, except for adequately treated, nonmetastatic malignancies; (c) low hemoglobin (<10 g/dL); (d) severe renal disease on dialysis (serum creatinine >2 mg/dL); (e) current and/or liver disease history, including known hepatitis B or C, with hepatic or biliary abnormalities; (iv) participants using any of the following treatments within the indicated washout period before baseline: (a) 5 half-lives or 12 weeks, whichever is longer—biologic agents (e.g., dupilumab); (b) 4 weeks—systemic corticosteroids or adrenocorticotropic hormone analogs, cyclosporin, methotrexate, azathioprine, or other systemic immunosuppressive or immunomodulating agents (e.g., mycophenolate or tacrolimus); (c) 2 weeks—immunizations and sedating antihistamines, unless on long-term stable regimen (nonsedating antihistamines are permitted); (d) 1 week—use of other topical treatments for AD (other than bland emollients), such as corticosteroids, calcineurin inhibitors, coal tar (shampoo), antibiotics, antibacterial cleansing body wash/soap. Diluted sodium hypochlorite "bleach" baths are allowed as long as they do not exceed 2 baths per week and their frequency remains the same throughout the study; (v) participants who have previously received JAK inhibitors, systemic or topical; (vi) ultraviolet light therapy or prolonged exposure to natural or artificial sources of UV radiation (e.g., sunlight or tanning booth) within 2 weeks prior to baseline and/or intention to have such exposure during the study, which is thought by the investigator to potentially impact the participant's AD; (vii) positive serology test results at screening for HIV antibody; (viii) liver function tests: AST or ALT ≥2×ULN; alkaline phosphatase and/or bilirubin >1.5×ULN (isolated bilirubin >1.5×ULN is acceptable if bilirubin is fractionated and direct bilirubin<35%); (ix) pregnant or lactating participants, or those considering pregnancy; (x) history of alcoholism or drug addiction within 1 year before screening or current alcohol or drug use that, in the opinion of the investigator, will interfere with the participant's ability to comply with the administration schedule and study assessments; (xi) current treatment or treatment within 30 days or 5 half-lives (whichever is longer) before baseline with another investigational medication or current enrollment in another investigational drug protocol; (xii) participants who, in the opinion of the investigator, are unable or unlikely to comply with the administration schedule and study evaluations; (xiii) participants who are committed to a mental health institution by virtue of an order issued either by the judicial or the administrative authorities; (xiv) employees of the sponsor or investigator or are otherwise dependents of them.

SCORAD is a tool to assess the extent and severity (i.e., intensity) of eczema and will be completed before, during, and after treatment has begun to determine whether the treatment has been effective (Oakley, 2009. https://www-.dermnetnz.org/topics/scorad/. Accessed Nov. 1, 2018.). This was be performed during all VC study visits, starting at baseline. To determine extent, the rule of 9 or handprint method was used to calculate the eczema affected area (A) as a percentage of the whole body. Scores were added up to give a possible maximum of 100%. To determine intensity, a representative area of eczema was selected (see below for target lesion). The intensity of each of the following signs of redness, swelling, oozing/crusting, scratch marks, skin thickening (lichenification), dryness (this is assessed in an area where there is no inflammation) was assessed as follows: None (0); Mild (1); Moderate (2); Severe (3). Intensity scores are added together to give "B" (maximum score of 18). Subjective symptoms, that is, itch and sleeplessness, are scored by the participant using a visual analogue scale where "0" is no itch (or no sleeplessness) and "10" is the worst imaginable itch (or sleeplessness). These scores were added to give "C" (maximum score of 20). Total score gave approximate weights of 60% to intensity and 20% each to extent and subjective signs (i.e., insomnia, etc.) for the participant and were calculated as follows: A/5+7B/2+C.

Target lesion assessment was performed as follows. At baseline, a lesion that is representative of the participant's overall disease and is to be treated with study drug was selected as the target lesion. This lesion was identified, measured, and documented in the participant's medical record at each subsequent visit during the VC period. A note should be made in their medical record, and baseline photographs could be marked with the location of the target lesion. The target lesion should not have been on the hands, feet, or genitalia. The target lesion should have had an area of approximately 10 cm$^2$ or more in size. The longest diameter and the measurement perpendicular to the longest diameter were measured in millimeters. The skin stripping (with tape discs), lesional skin S. aureus swabs, and TEWL assessments were taken from the target lesion after photographs are taken and before study treatment was applied.

Total % BSA afflicted by AD was estimated at each visit in the VC period. Body surface area assessment was approximated to the nearest 0.1% using the Palmar Method as guides, the palm plus 5 digits, with fingers tucked together and thumb tucked to the side (handprint), as 1% BSA and the thumb as 0.1% BSA.

Various patient-reported outcomes were assessed, including quality of life (QoL) using the following tools: DQLI (Dermatology Life Quality Index), PGIC (Patient Global Impression of Change), POEM (Patient-Oriented Eczema Measure), EQ-5D-5L (EQ-5D is a validated, self-administered, generic, utility questionnaire wherein participants will rate their current health state based on the following criteria: mobility, self-care, usual activities, pain/discomfort, and anxiety/depression), WPAI:SHP (Work Productivity and Activity Impairment Questionnaire: Specific Health Problem Version 2.0), Itch NRS, Skin Pain NRS (Skin Pain Numerical Rating Scale), PROMIS Short Form—Sleep-Related Impairment (8a), and PROMIS Short Form—Sleep Disturbance (8b). In order to avoid bias in the participants' responses to the questionnaires, all these assessments were completed before any other evaluations or study procedures on the day of the study visit and prior to discussions with the investigator or study site staff. At the baseline visit, all patient-reported outcomes were completed before the participant's first study drug application.

Participants were issued a paper questionnaire or handheld device (eDiary) for daily assessments. The participant was instructed to complete the diary during specific timepoints needed for each assessment beginning on the day of screening through Week 8 or treatment discontinuation. Daily assessments was performed by participants via a diary starting at the screening visit and all visits during the VC period: The participant rated (during the past 24 hours) the following: Itch NRS—the worst level of itch will be recorded in the evening; Skin Pain NRS—the worst level of pain will be recorded in the evening; PROMIS questionnaires; Short Form—Sleep-Related Impairment (8a) will be completed in the evening; Short Form—Sleep-Disturbance (8b) will be assessed in the morning.

During all VC site visits, the following was assessed: EQ-5D-5L—starts at screening; WPAI:SHP—starts at screening; DLQI/CDLQI—starts at Day 1; POEM—starts at Day 1; PGIC—starts at Week 2.

During the LTS period, the following will be assessed: EQ-5D-5L; WPAI:SHP; DLQI/CDLQI; POEM; PROMIS Short Form—Sleep-Related Impairment (8a) and Short Form—Sleep-Disturbance (8b):

The DLQI is a simple, 10-question validated questionnaire to measure how much the skin problem has affected the participant over the previous 7 days as outlined in the SoAs (Finlay A Y, Khan G K, "Dermatology Life Quality Index (DLQI)-a simple practical measure for routine clinical use," Clin Exp Dermatol 1994; 19:210-216.). The participant, aged ≥16 years and over, answered the questionnaire with either (1) very much, (2) a lot, (3) a little, or (4) not at all. The questionnaire was analyzed under 6 headings as follows: Symptoms and feelings (Questions 1 and 2); Daily activities (Questions 3 and 4); Leisure (Questions 5 and 6); Work and school (Question 7); Personal relations (Questions 8 and 9); Treatment (Question 10).

CDLQI is the youth/children's version of the DLQI and was completed by adolescents aged ≥12 years to <16 years. It is self-explanatory and could be simply given to the participant who was asked to fill it in and who could ask the help of the parent or guardian. The questionnaire was analyzed under 6 headings as follows: Symptoms and feelings (Questions 1 and 2); Leisure (Questions 4, 5, and 6); School or holidays (Question 7); Personal relationships (Questions 3 and 8); Sleep (Question 9); Treatment (Question 10); Patient Global Impression of Change The PGIC is a participants' self-reporting measure that reflects their belief about the efficacy of treatment. The PGIC is a 7-point scale depicting a participant's rating of overall improvement and will be captured during site visits during the VC period (Hurst H, Bolton J. "Assessing the clinical significance of change scores recorded on subjective outcome measures," J Manipulative Physiol Ther 2004; 27:26-35). The participant will answer the following: "Since the start of the treatment you've received in this study, your atopic dermatitis in areas treated with the study drug is: (1) very much improved, (2) much improved, (3) minimally improved, (4) no change, (5) minimally worse, (6) much worse, and (7) very much worse."

The POEM is a 7-question quality-of-life assessment that asks how many days the participant has been bothered by various aspects of their skin condition during the past 7 days obtained as outlined in the SoAs (Charman CR, et al., Arch Dermatol 2004, 140:1513-1519).

The EQ-5D-5L: The EQ-5D is a validated, self-administered, generic utility questionnaire wherein participants (adolescents and adults) rate their current health state based on the following criteria (dimensions): mobility, self-care, usual activities, pain/discomfort, and anxiety/depression. The 5L indicates that for each dimension, there are 5 levels, which are as follows: no problems, slight problems, moderate problems, severe problems, and extreme problems. During all VC period study visits (starting at screening) and at specific LTS visits (Weeks 12, 24, 36, 52, and follow-up visit), the participant was asked to indicate his/her health state over the past 7 days, by ticking the box next to the most appropriate statement in each of the 5 dimensions. The digits for the 5 dimensions can be combined into a 5-digit number that describes the participant's health state (EuroQol Research Foundation. EQ-5D-5L. 2017. https://euroqol.org/eq-5d-instruments/eq-5d-5l-about/. Accessed Jul. 17, 2018).

The WPAI:SHP v2.0 questionnaire is a validated 6-item instrument, completed during all site visits starting at screening, during the VC period, and at specific LTS visits (Weeks 12, 24, 36, 52 and follow-up visit) that measures the effect of overall health and specific symptoms on productivity at work and regular activities outside of it during the past 7 days (Reilly M C, Zbrozek A S, Dukes E M, "The validity and reproducibility of a work productivity and activity impairment instrument," *PharmacoEconomics* 1993; 4:353-365).

The Itch NRS is a daily patient-reported measure (24-hour recall) of the worst level of itch intensity. Participants were asked to rate the itching severity because of their AD by selecting a number from 0 (no itch) to 10 (worst imaginable itch) that best describes their worst level of itching in the past 24 hours. Participants were issued a diary in which to record itch severity. The participants was instructed to complete the diary each night beginning on the day of screening through the last application of study drug in the VC period.

The Skin Pain NRS is a daily patient-reported measure (24-hour recall) of the worst level of pain intensity from 0 (no pain) to 10 (worst imaginable pain). Participants were asked, "Rate the pain severity from your atopic dermatitis skin changes by selecting a number that best describes your worst level of pain in the past 24 hours," as outlined in the SoA.

Participants were issued a diary in which to record skin pain severity each evening, rating the worst pain in the past 24-hours. The participants were instructed to complete the diary each night beginning on the day of screening through the last application of study drug in the VC period.

PROMIS® (Patient-Reported Outcomes Measurement Information System) is a set of widely used and accepted patient-reported outcome measurements that have been developed with strong clinical outcome assessment development methods and are psychometrically supported. The selected PROMIS Short Form—Sleep-Related Impairment (8a) and Short Form—Sleep-Disturbance (8b) questionnaires were modified to be completed with a diary on a daily basis with a 24-hour recall: Short Form—Sleep-Related Impairment (8a) is collected in the evening, and Short Form—Sleep-Disturbance (8b) is collected in the morning during the VC period. Starting at Week 8 and during the LTS period, these were/will be done with a 7-day recall period and be completed at the site during study visits.

The PROMIS Short Form—Sleep-Related Impairment (8a) questionnaire, was completed in the evening during the VC period. This assessment focuses on self-reported perceptions of alertness, sleepiness, and tiredness during usual waking hours and the perceived functional impairments during wakefulness associated with sleep problems or impaired alertness (Buysse, *Sleep* 2010; 33:781-792). The questionnaire has 8 simple questions with a 5-point scale with a range in score from 8 to 40, with higher scores indicating greater severity of sleep-related impairment. Each item asks the participant to rate the severity of the participant's sleep impairment. The recall period was the past 24 hours for the VC period and the past 7 days for the LTS period.

The PROMIS Short Form—Sleep Disturbance (8b) questionnaire was completed in the morning during the VC period. This assessment is self-reported perceptions of sleep quality, sleep depth, and restoration associated with sleep. Sleep disturbance does not focus on symptoms of specific sleep disorders and does not provide subjective estimates of sleep quantities (e.g., total amount of sleep, time to fall asleep, amount of wakefulness during sleep; Buysse et al 2010). The sleep disturbance short form is generic rather than disease-specific. The questionnaire is also 5-point scale with a range in score from 8 to 40, with higher scores indicating greater severity of sleep disturbance. Each item asked the participant to rate the severity of the participant's sleep disturbance. The recall period was the past 24 hours for the VC period and the past 7 days for the LTS period.

Results from the VC Period

In TRuE-AD1 (Study 303), 631 patients were randomized (vehicle, n=126; 0.75% BID, n=252; 1.5% BID, n=253); the median (range) age was 32.0 (12-85) years and 62.0% of patients were female. Seventy-three patients (11.6%) discontinued from the study. In TRuE-AD2 (Study 304), 618 patients were randomized (vehicle, n=124; 0.75% BID, n=248; 1.5% BID, n=246); the median (range) age was 33.0 (12-85) years and 61.5% were female. Fifty-seven patients (9.2%) discontinued from the study. The full demographics for TRuE-AD1 and TRuE-AD2 are shown in Tables 10 and 11, respectively. Mean baseline itch NRS score for the pooled TRuE-AD1 and TRuE-AD2 populations for vehicle, 0.75% BID, and 1.5% BID populations were 5.15, 5.14, and 5.09, respectively.

TABLE 10

| Parameters | Total | Parameters | Total |
|---|---|---|---|
| Age | | Race n (%) | |
| Mean (SD) | 35.2 (18.15) | White | 431 (68.3) |
| Median (Min-Max) | 32 (12-85) | Black | 140 (22.2) |
| 12-17 n (%) | 123 (19.5) | Asian | 32 (5.1) |
| >=18 n (%) | 508 (80.5) | Others | 28 (4.5) |
| Sex n (%) | | Region n (%) | |
| Male | 240 (38) | North America | 440 (69.7) |
| Female | 391 (62) | Europe | 191 (30.3) |
| Baseline IGA n (%) | | Baseline EASI n (%) | |
| 2 | 152 (24.1) | <=7 | 318 (50.4) |
| 3 | 479 (75.9) | >7 | 313 (49.6) |

TABLE 11

| Parameters | Total | Parameters | Total |
|---|---|---|---|
| Age | | Race n (%) | |
| Mean (SD) | 36.4 (18.38) | White | 436 (70.6) |
| Median (Min-Max) | 33 (12-85) | Black | 152 (24.6) |
| 12-17 n (%) | 122 (19.7) | Asian | 14 (2.3) |
| >=18 n (%) | 496 (80.3) | Others | 16 (2.6) |
| Sex n (%) | | Region n (%) | |
| Male | 238 (38.5) | North America | 415 (67.2) |
| Female | 380 (61.5) | Europe | 203 (32.8) |
| Baseline IGA n (%) | | Baseline EASI n (%) | |
| 2 | 160 (25.9) | <=7 | 302 (48.9) |
| 3 | 458 (74.1) | >7 | 316 (51.1) |

The efficacy population consisted of 631 patients for TRuE-AD1 (all randomized patients), and 577 patients for TRuE-AD2 (vehicle, n=118; 0.75% BID, n=231; 1.5% BID, n=228). All patients who received ≥1 dose of treatment (all randomized patients) were included in the safety population in both studies.

A summary of the primary and major secondary efficacy endpoints for TRuE-AD1 (Study 303) and TRuE-AD2 (Study 304) are shown in Tables 12 and 13.

TABLE 12

|  | Vehicle | 0.75% BID | 1.5% BID |
|---|---|---|---|
| N | 126 | 252 | 253 |
| IGA-TS | 15.1% | 50% ** | 53.8% ** |
| EASI75 | 24.6% | 56.0% ** | 62.1% ** |
| ITCH4 | 15.4% | 40.4% ** | 52.2% **^ |
| PROMIS6 8b | 9.5% | 21% * | 22.3% * |
| PROMIS6 8a | 13.2% | 20.2% | 21.6% |

** p < 0.0001, Rux vs. vehicle;
* p < 0.01 Rux vs. vehicle;
^ p = 0.04, 1.5% BID vs 0.75% BID

TABLE 13

|  | Vehicle | 0.75% BID | 1.5% BID |
|---|---|---|---|
| N | 118 | 231 | 228 |
| IGA-TS | 7.6% | 39.0% ** | 51.3% **^^ |
| EASI75 | 14.4% | 51.5% ** | 61.8% **^ |
| ITCH4 | 16.3% | 42.7% ** | 50.7% ** |
| PROMIS6 8b | 19.1% | 20.7% | 25.6% |
| PROMIS6 8a | 13.5% | 20.0% | 23.1% |

Figure 11:
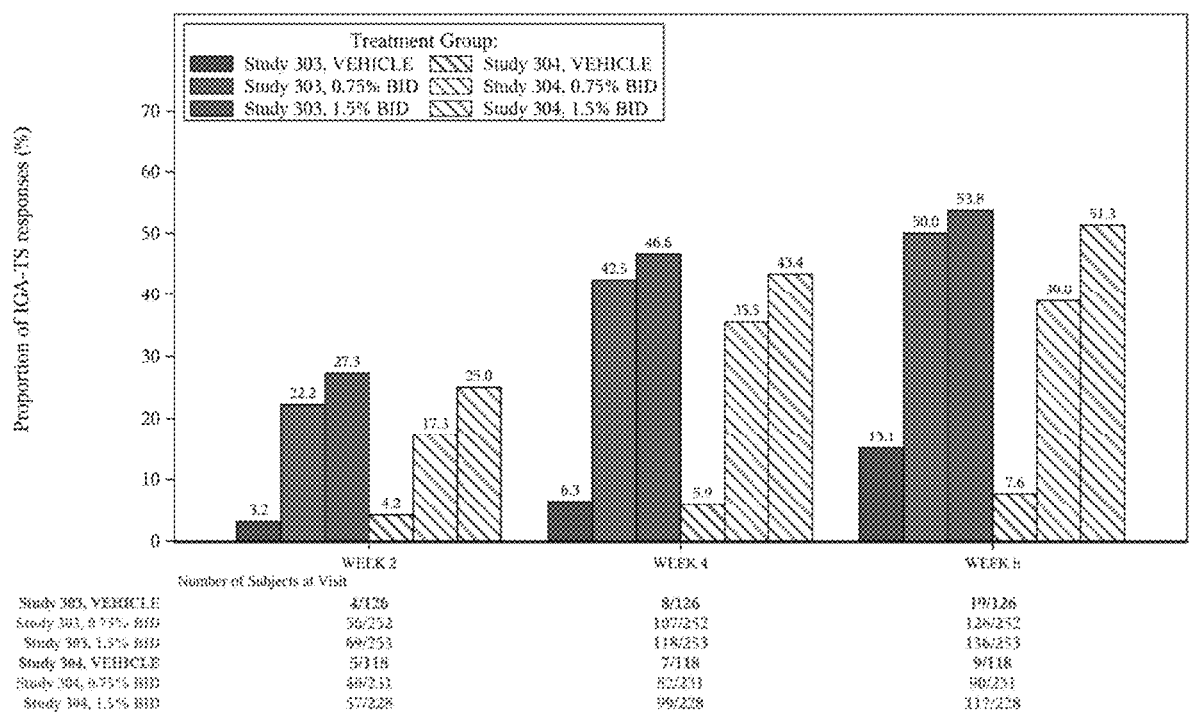
FIG. 11 depicts the proportion of participants that achieved IGA-TS in the vehicle control period at Week 2, Week 4, and Week 8 for TRuE-AD1 (Study 303) (solid bars) and TRuE-AD2 (Study 304) (striped bars) for vehicle, 0.75% BID ruxolitinib cream, and 1.5% BID ruxolitinib cream (first bar of each set is vehicle; second bar of each set is 0.75% BID ruxolitinib cream; and third bar of each set is 1.5% ruxolitinib cream).

** p < 0.0001, Rux vs. vehicle;
* p < 0.01 Rux vs. vehicle;
^ p = 0.04, 1.5% BID vs 0.75% BID In TRuE-AD1 and TRuE-AD2, respectively, significantly more patients treated with ruxolitinib cream achieved IGA treatment success (0.75% BID, 50.0% and 39.0%; 1.5% BID, 53.8% and 51.3%) vs vehicle (15.1% and 7.6%; all P<0.0001) (FIG. 11).

Figure 12:
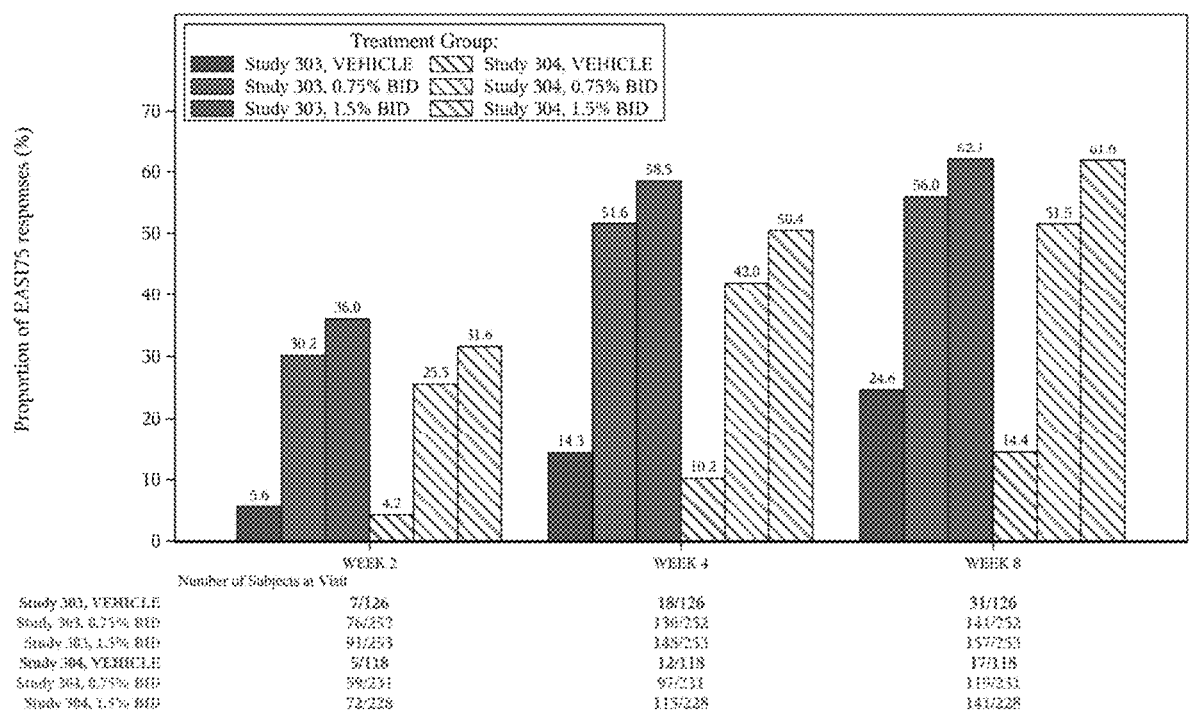
FIG. 12 depicts the proportion of participants that achieved EASI75 in the vehicle control period at Week 2, Week 4, and Week 8 for TRuE-AD1 (Study 303) (solid bars) and TRuE-AD2 (Study 304) (striped bars) for vehicle, 0.75% BID ruxolitinib cream, and 1.5% BID ruxolitinib cream (first bar of each set is vehicle; second bar of each set is 0.75% BID ruxolitinib cream; and third bar of each set is 1.5% ruxolitinib cream).
Figure 31:
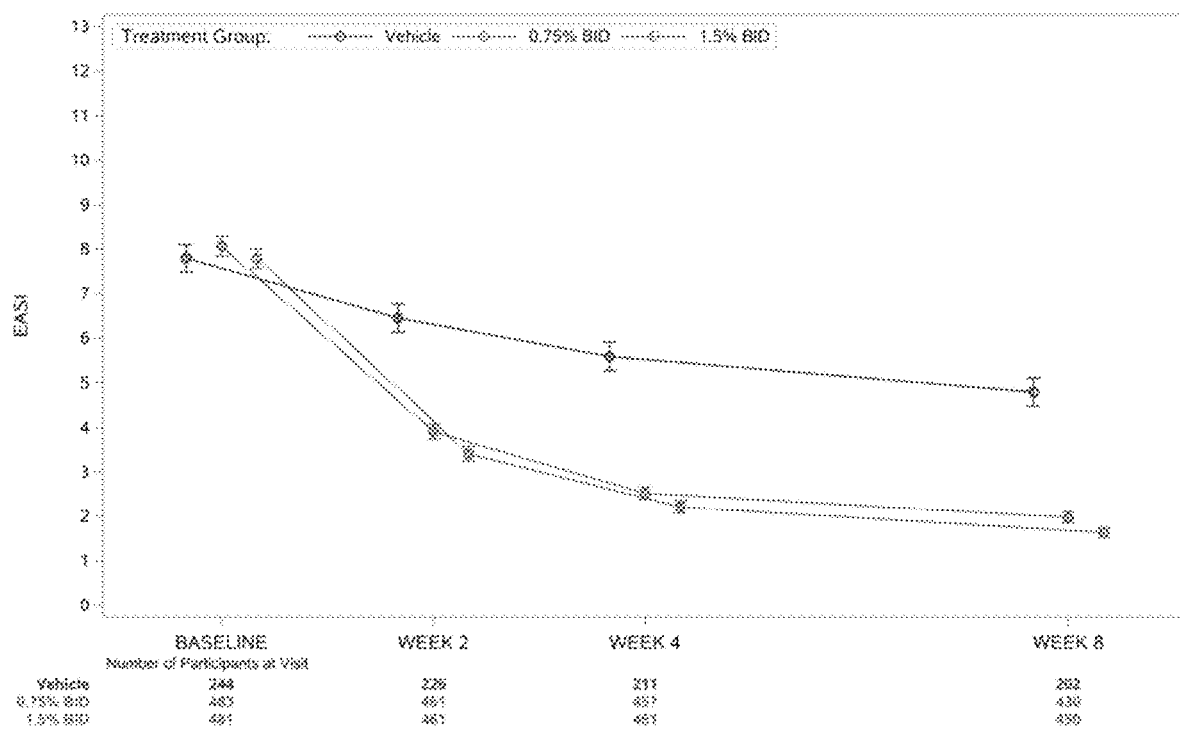
FIG. 31 shows a graph of mean in EASI scores in the vehicle control period at Baseline, Week 2, Week 4, and Week 8 for the pooled TRuE-AD1(Study 303) and TRuE-AD2 (Study 304) (top line (vehicle), middle line (0.75% BID ruxolitinib cream), and bottom line (1.5% BID ruxolitinib cream).
Figure 32:
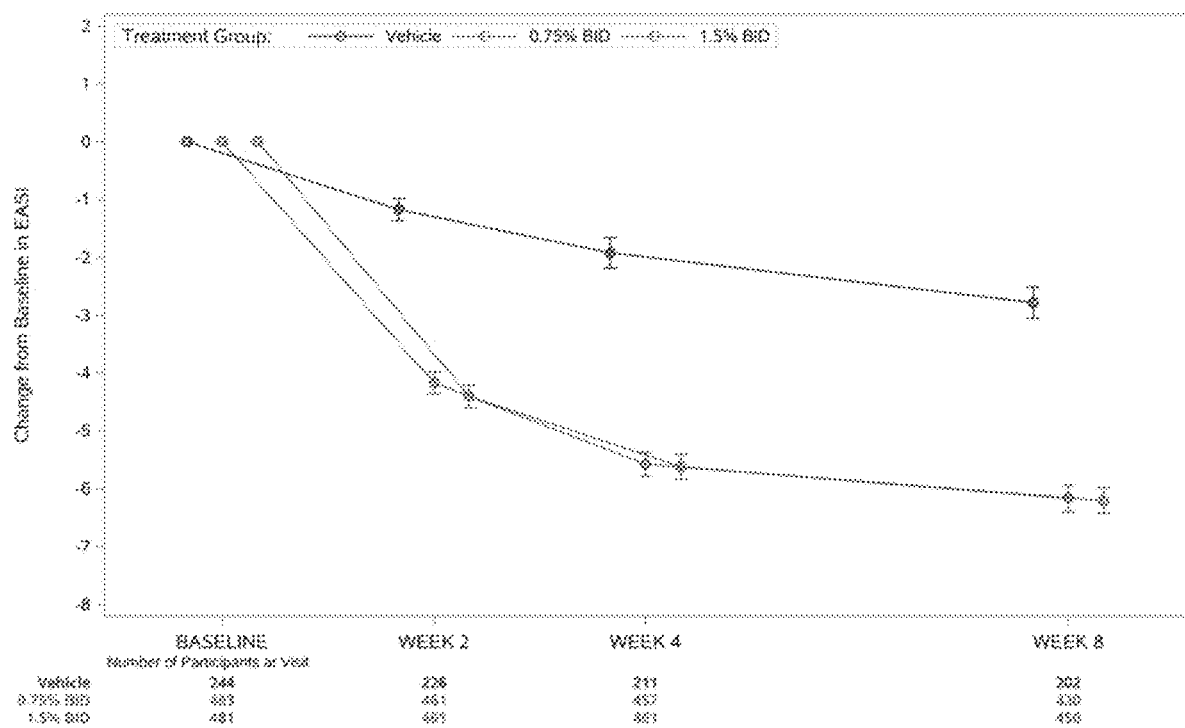
FIG. 32 shows a graph of mean score change from baseline in EASI scores in the vehicle control period at Baseline, Week 2, Week 4, and Week 8 for the pooled TRuE-AD1 (Study 303) and TRuE-AD2 (Study 304) (top line (vehicle), middle line (1.5% BID ruxolitinib cream), and bottom line (0.75% BID ruxolitinib cream).
Figure 33:
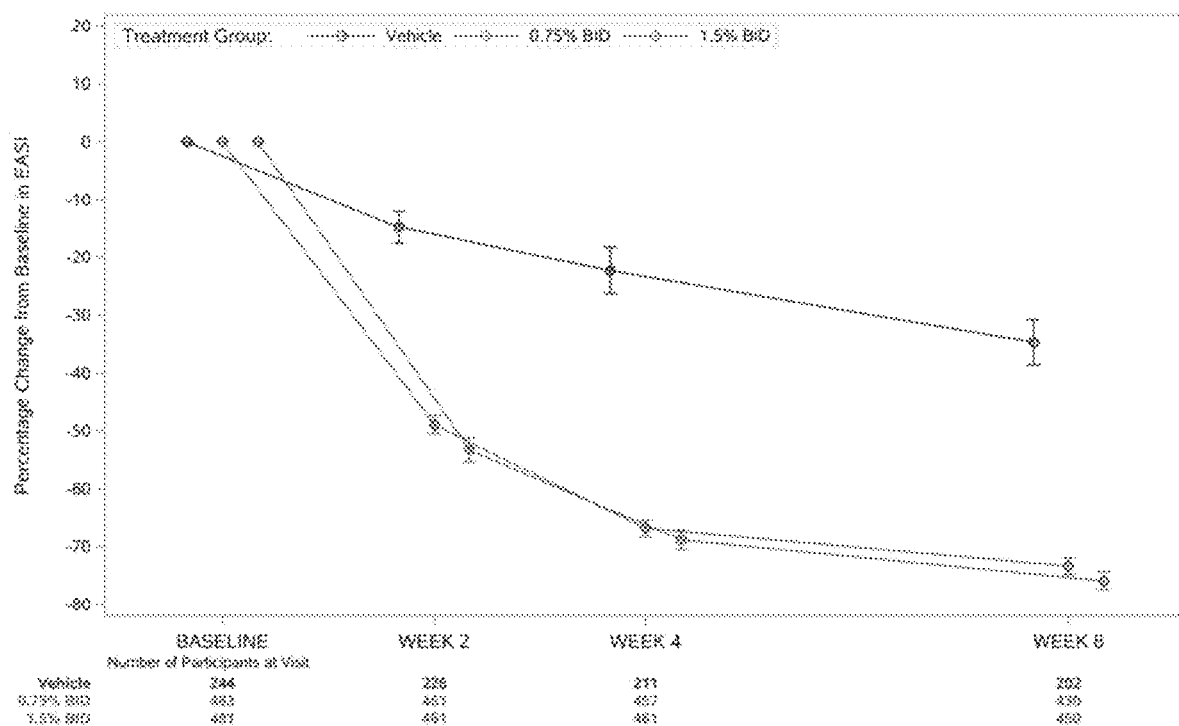
FIG. 33 shows a graph of mean percentage change from baseline in EASI scores in the vehicle control period at Baseline, Week 2, Week 4, and Week 8 for the pooled TRuE-AD1(Study 303) and TRuE-AD2 (Study 304) (top line (vehicle), middle line (1.5% BID ruxolitinib cream), and bottom line (0.75% BID ruxolitinib cream).

EASI-75 was achieved by 56.0% and 51.5% of patients applying ruxolitinib cream 0.75% BID, as well as 62.1% and 61.8% on 1.5% BID vs 24.6% and 14.4% on vehicle (all P<0.0001) in TRuE-AD1 and TRuE-AD2, respectively (FIG. 12). In TRuE-AD1 (Study 303), Eczema Area and Severity Index scores decreased over time with clear separation for both active treatment groups from the vehicle treatment group by Week 2. In the pooled TRuE-AD1 (Study 303) and TRuE-AD2 (Study 304) studies, Eczema Area and Severity Index scores decreased over time with clear separation for both active treatment groups from the vehicle treatment group by Week 2 (see FIGS. 31, 32, and 33).

Figure 13:
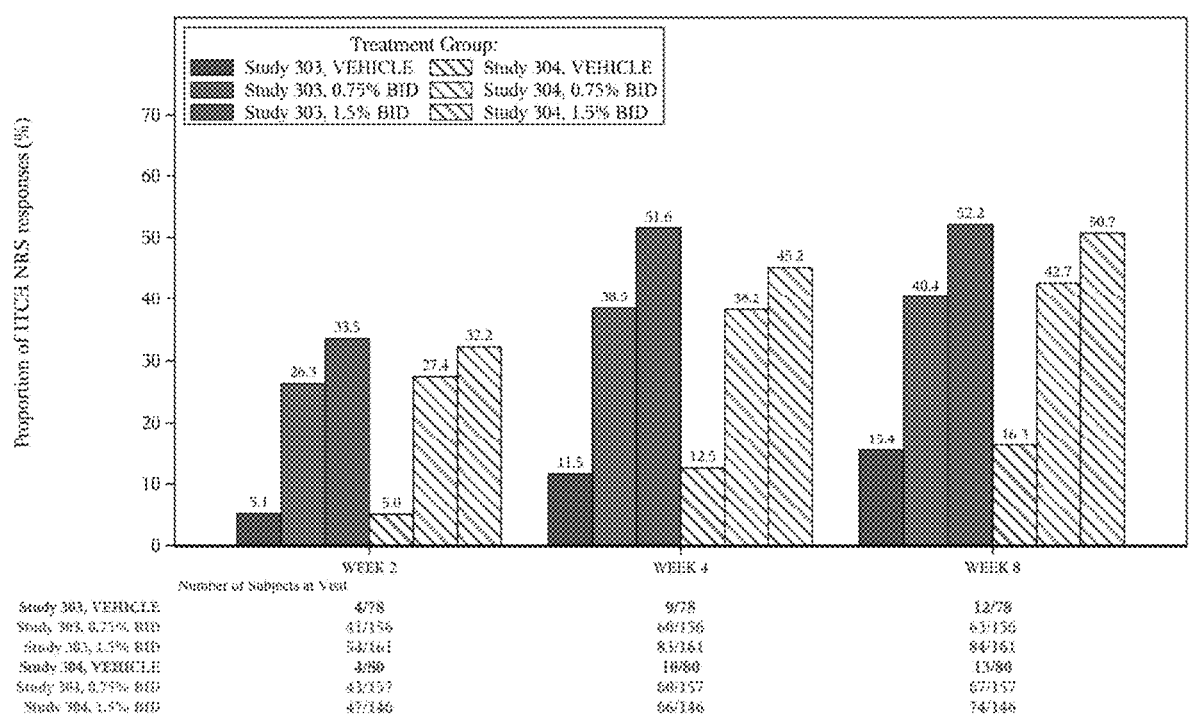
FIG. 13 depicts the proportion of participants that achieved a ≥4-point improvement in itch NRS score in the vehicle control period at Week 2, Week 4, and Week 8 for TRuE-AD1 (Study 303) (solid bars) and TRuE-AD2 (Study 304) (striped bars) for vehicle, 0.75% BID ruxolitinib cream, and 1.5% BID ruxolitinib cream for patients having baseline itch NRS ≥4 (first bar of each set is vehicle; second bar of each set is 0.75% BID ruxolitinib cream; and third bar of each set is 1.5% ruxolitinib cream).
Figure 14:
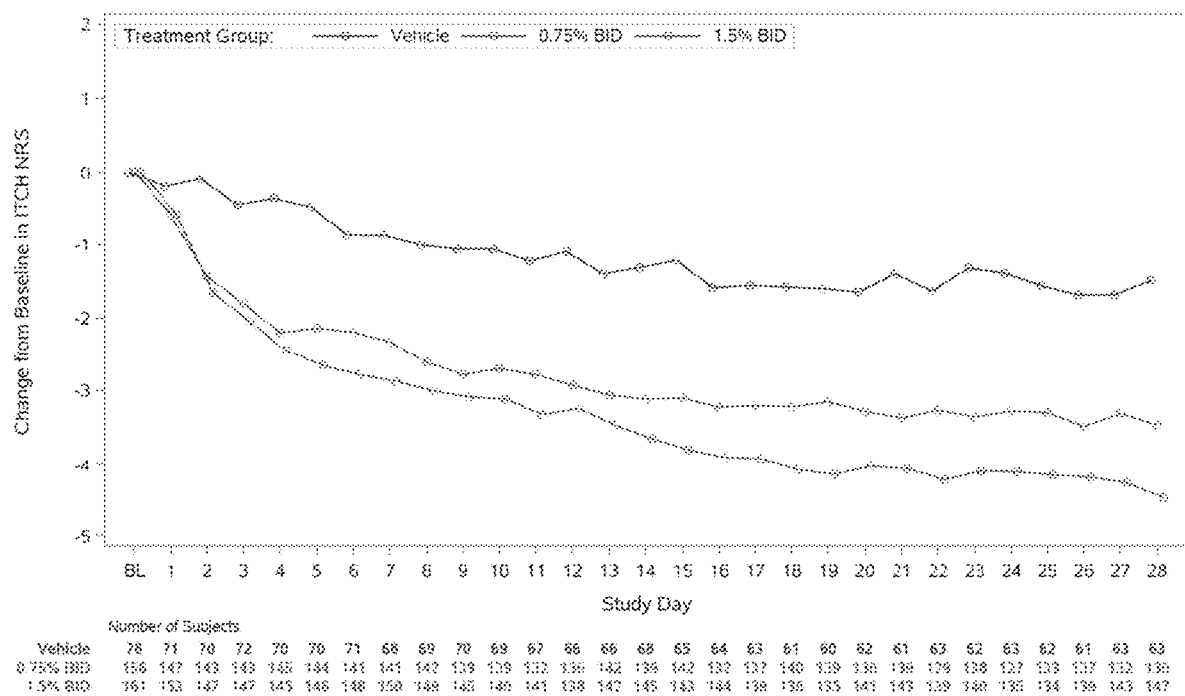
FIG. 14 depicts the mean change from baseline in daily itch NRS score from Day 1 to Day 28 for TRuE-AD1 (Study 303) for vehicle (top line), 0.75% BID ruxolitinib cream (middle line), and 1.5% BID ruxolitinib cream (bottom line) for patients having baseline itch NRS ≥4.
Figure 15:
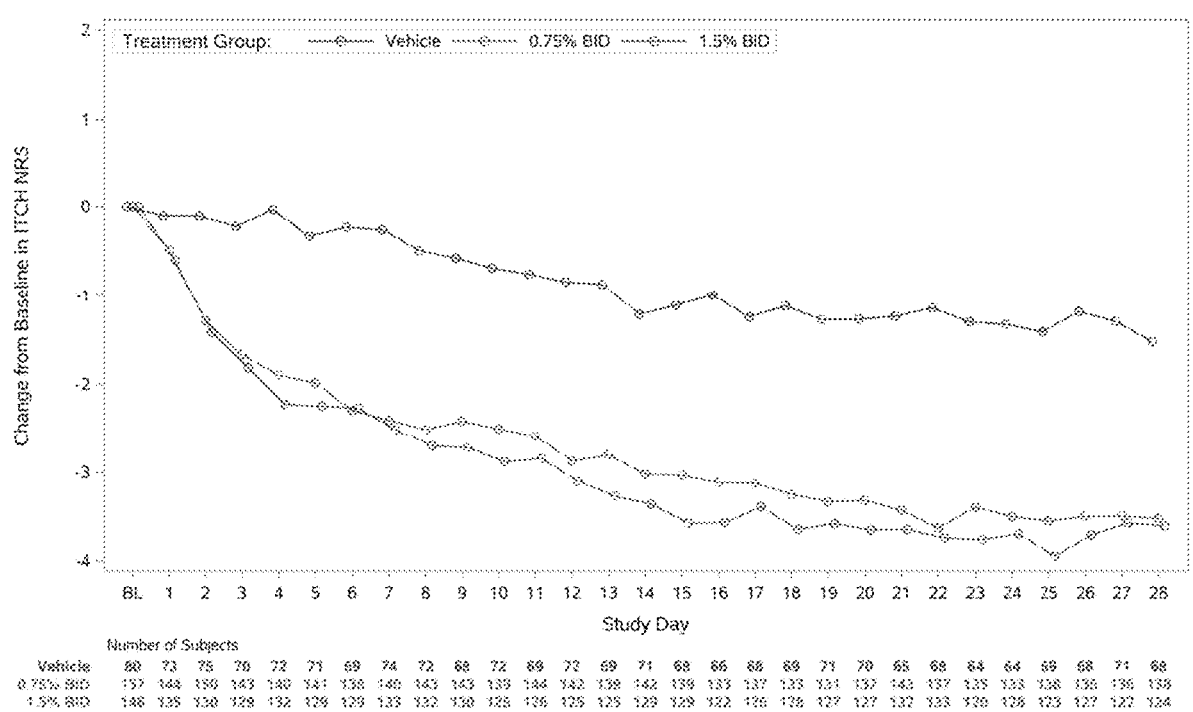
FIG. 15 depicts the mean change from baseline in daily itch NRS score from Day 1 to Day 28 for TRuE-AD2 (Study 304) for vehicle (top line), 0.75% BID ruxolitinib cream (middle line), and 1.5% BID ruxolitinib cream (bottom line) for patients having baseline itch NRS ≥4.

In both studies, patients who applied ruxolitinib cream (0.75% BID or 1.5% BID) achieved statistically significant itch reductions (NRS4) compared with vehicle at Week 8 (FIG. 13; numbers are for patients with baseline itch NRS score ≥4). In addition to attaining sustained itch reduction at Week 8, patients who applied ruxolitinib cream (0.75% BID or 1.5% BID) also experienced rapid reduction in itch within 1-2 days (FIG. 14 and FIG. 15; Table 14 (TRuE-AD1; mean baseline itch NRS score 6.39, 6.44, and 6.45 for vehicle, 0.75% BID, and 1.5% BID, respectively); Table 15 (TRuE-AD2; mean baseline itch NRS score 6.42, 6.38, and 6.38 for vehicle, 0.75% BID, and 1.5% BID, respectively); numbers are for patients with baseline itch NRS score ≥4).

TABLE 14

| | Mean change from baseline itch NRS score | | | | |
|---|---|---|---|---|---|
| Day | Vehicle | 0.75% BID | p-value | 1.5% BID | p-value |
| N | 78 | 156 | | 161 | |
| 1 | −0.21 | −0.61 | | −0.60 | |

TABLE 14-continued

| | Mean change from baseline itch NRS score | | | | |
|---|---|---|---|---|---|
| Day | Vehicle | 0.75% BID | p-value | 1.5% BID | p-value |
| 2 | −0.11 | −1.43 | <0.0001 | −1.66 | <0.0001 |
| 3 | −0.46 | −1.81 | <0.0001 | −2.05 | <0.0001 |
| 4 | −0.38 | −2.21 | <0.0001 | −2.45 | <0.0001 |
| 5 | −0.5 | −2.14 | <0.0001 | −2.66 | <0.0001 |
| 6 | −0.88 | −2.20 | <0.0001 | −2.79 | <0.0001 |
| 7 | −0.88 | −2.33 | <0.0001 | −2.88 | <0.0001 |
| 14 | −1.32 | −3.12 | <0.0001 | −3.66 | <0.0001 |
| 21 | −1.40 | −3.38 | <0.0001 | −4.06 | <0.0001 |
| 28 | −1.49 | −3.47 | <0.0001 | −4.46 | <0.0001 |
| 35 | −1.91 | −3.65 | <0.0001 | −4.73 | <0.0001 |
| 42 | −1.83 | −3.51 | <0.0001 | −4.52 | <0.0001 |
| 49 | −2.22 | −3.65 | <0.0001 | −4.80 | <0.0001 |
| 56 | −2.16 | −3.52 | <0.0001 | −4.64 | <0.0001 |

*p-value between the ruxolitinib cream group and vehicle

TABLE 15

| | Mean change from baseline itch NRS score | | | | |
|---|---|---|---|---|---|
| Day | Vehicle | 0.75% BID | p-value | 1.5% BID | p-value |
| N | 80 | 157 | | 146 | |
| 1 | −0.10 | −0.48 | 0.0598 | −0.60 | 0.0159 |
| 2 | −0.10 | −1.29 | <0.0001 | −1.42 | <0.0001 |
| 3 | −0.22 | −1.67 | <0.0001 | −1.82 | <0.0001 |
| 4 | −0.03 | −1.90 | <0.0001 | −2.23 | <0.0001 |
| 5 | −0.33 | −1.99 | <0.0001 | −2.25 | <0.0001 |
| 6 | −0.23 | −2.30 | <0.0001 | −2.27 | <0.0001 |
| 7 | −0.26 | −2.41 | <0.0001 | −2.51 | <0.0001 |
| 14 | −1.22 | −3.02 | <0.0001 | −3.36 | <0.0001 |
| 21 | −1.24 | −3.43 | <0.0001 | −3.65 | <0.0001 |
| 28 | −1.53 | −3.52 | <0.0001 | −3.61 | <0.0001 |
| 35 | −1.59 | −3.94 | <0.0001 | −3.80 | <0.0001 |
| 42 | −1.59 | −3.95 | <0.0001 | −3.87 | <0.0001 |
| 49 | −1.70 | −3.94 | <0.0001 | −3.82 | <0.0001 |
| 56 | −1.77 | −3.88 | <0.0001 | −3.89 | <0.0001 |

* p-value between the ruxolitinib cream group and vehicle

In both TRuE-AD1 and TRuE-AD2, significantly greater itch reduction as compared to vehicle was observed by day 2 (within 12 hours of first application of ruxolitinib cream) for patients receiving 1.5% ruxolitinib cream BID (Tables 16 (TRuE-AD1) and Table 17 (TRuE-AD2), as measured for the entire patient population). Mean baseline itch NRS score for vehicle, 0.75% BID, and 1.5% BID for Table 16 was 5.06, 5.13, and 5.15, respectively. Mean baseline itch NRS score for vehicle, 0.75% BID, and 1.5% BID for Table 17 was 5.25, 5.15, and 5.02, respectively. By day 2 (within 36 hours of the first application of ruxolitinib cream), patients achieved significantly greater itch reduction for 0.75% BID ruxolitinib cream in both studies.

TABLE 16

| | Mean change from baseline itch NRS score | | | | |
|---|---|---|---|---|---|
| Day | Vehicle | 0.75% BID | p-value | 1.5% BID | p-value |
| N | 126 | 252 | | 253 | |
| 1 | −0.09 | −0.41 | 0.0512 | −0.48 | 0.0161 |
| 2 | −0.03 | −1.12 | <0.0001 | −1.27 | <0.0001 |
| 3 | −0.09 | −1.49 | <0.0001 | −1.61 | <0.0001 |
| 4 | 0.06 | −1.33 | <0.0001 | −1.90 | <0.0001 |
| 5 | −0.16 | −1.78 | <0.0001 | −2.07 | <0.0001 |
| 6 | −0.45 | −1.81 | <0.0001 | −2.18 | <0.0001 |
| 7 | −0.43 | −1.93 | <0.0001 | −2.23 | <0.0001 |
| 14 | −0.78 | −2.60 | <0.0001 | −2.81 | <0.0001 |
| 21 | −0.98 | −2.72 | <0.0001 | −3.08 | <0.0001 |

TABLE 16-continued

Mean change from baseline itch NRS score

| Day | Vehicle | 0.75% BID | p-value | 1.5% BID | p-value |
|---|---|---|---|---|---|
| 28 | −1.03 | −2.81 | <0.0001 | −3.39 | <0.0001 |
| 35 | −1.32 | −2.99 | <0.0001 | −3.69 | <0.0001 |
| 42 | −1.24 | −2.83 | <0.0001 | −3.44 | <0.0001 |
| 49 | −1.41 | −2.98 | <0.0001 | −3.65 | <0.0001 |
| 56 | −1.51 | −2.97 | <0.0001 | −3.53 | <0.0001 |

* p-value between the ruxolitinib cream group and vehicle

TABLE 17

Mean change from baseline itch NRS score

| Day | Vehicle | 0.75% BID | p-value | 1.5% BID | p-value |
|---|---|---|---|---|---|
| N | 118 | 231 | | 228 | |
| 1 | −0.12 | −0.35 | 0.1713 | −0.48 | 0.0290 |
| 2 | −0.08 | −1.12 | <0.0001 | −1.21 | <0.0001 |
| 3 | −0.20 | −1.42 | <0.0001 | −1.45 | <0.0001 |
| 4 | −0.02 | −1.60 | <0.0001 | −1.81 | <0.0001 |
| 5 | −0.24 | −1.65 | <0.0001 | −1.84 | <0.0001 |
| 6 | −0.22 | −1.94 | <0.0001 | −1.83 | <0.0001 |
| 7 | −0.24 | −2.00 | <0.0001 | −2.07 | <0.0001 |
| 14 | −0.94 | −2.52 | <0.0001 | −2.75 | <0.0001 |
| 21 | −1.00 | −2.79 | <0.0001 | −2.95 | <0.0001 |
| 28 | −1.09 | −2.89 | <0.0001 | −2.88 | <0.0001 |
| 35 | −1.29 | −3.15 | <0.0001 | −3.10 | <0.0001 |
| 42 | −1.23 | −3.21 | <0.0001 | −3.03 | <0.0001 |
| 49 | −1.40 | −3.13 | <0.0001 | −3.01 | <0.0001 |
| 56 | −1.33 | −3.04 | <0.0001 | −3.17 | <0.0001 |

*p-value between the ruxolitinib cream group and vehicle

Figure 25:
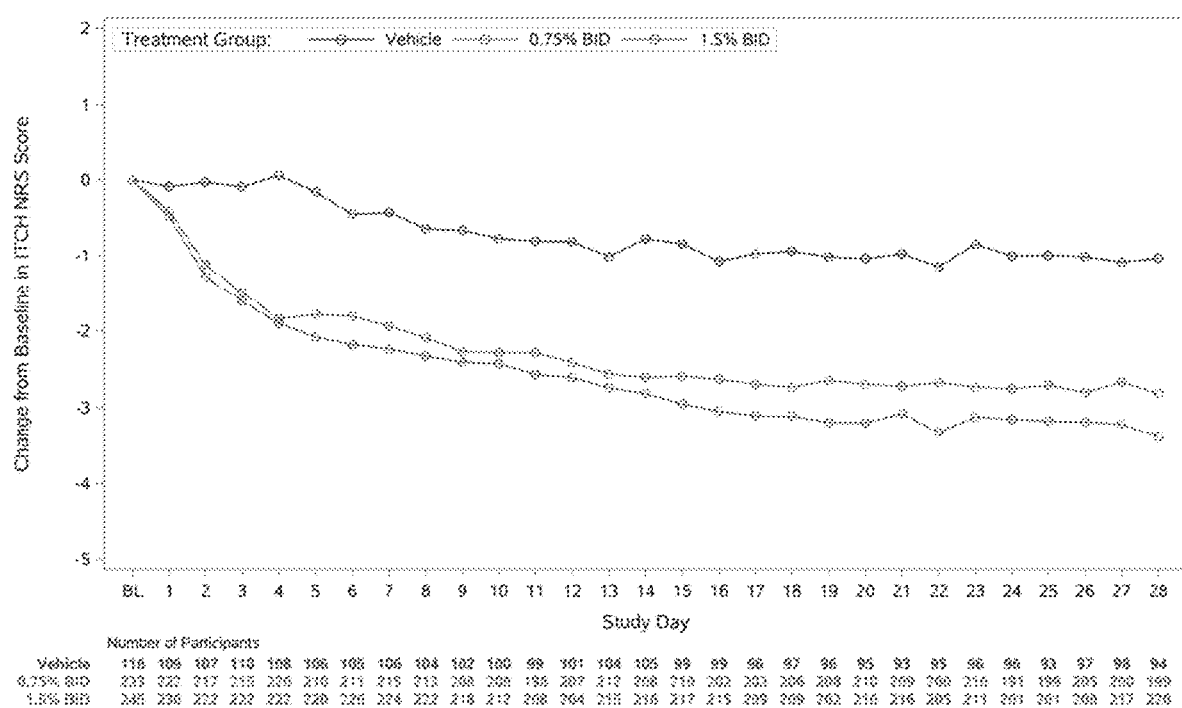
FIG. 25 depicts mean change from baseline in daily itch NRS scores from day 1 to day 28 (patients having a baseline itch NRS score of ≥4) for the pooled TRuE-AD1 (Study 303) and TRuE-AD2 (Study 304) studies (top line (vehicle), middle line (0.75% BID ruxolitinib cream), and bottom line (1.5% BID ruxolitinib cream).

The pooled data for the TRuE-AD1 and TRuE-AD2 studies for mean change from baseline in daily itch NRS score is shown in Table 18 and in FIG. 25. The p-values show that the differences for 0.75% and 1.5% ruxolitinib cream become significant by day 1 (within 12 hours). The mean change from baseline in daily itch NRS score at day 1 (within 12 hours) for 0.75% and 1.5% ruxolitinib cream is −0.38 and −0.48, respectively. The mean change from baseline in daily itch NRS score at day 2 (within 36 hours) for 0.75% and 1.5% ruxolitinib cream is −1.12 and −1.24, respectively.

TABLE 18

| Study Day | Mean change from baseline in daily itch NRS score | | | | |
|---|---|---|---|---|---|
| | Vehicle | 0.75% BID | p-value | 1.5% BID | p-value |
| 1 | −0.10 | −0.38 | 0.0180 | −0.48 | 0.0011 |
| 2 | −0.06 | −1.12 | <0.0001 | −1.24 | <0.0001 |
| 3 | −0.14 | −1.45 | <0.0001 | −1.53 | <0.0001 |
| 4 | 0.02 | −1.72 | <0.0001 | −1.86 | <0.0001 |
| 5 | −0.20 | −1.72 | <0.0001 | −1.96 | <0.0001 |
| 6 | −0.34 | −1.87 | <0.0001 | −2.01 | <0.0001 |
| 7 | −0.34 | −1.97 | <0.0001 | −2.15 | <0.0001 |
| 8 | −0.53 | −2.09 | <0.0001 | −2.30 | <0.0001 |
| 9 | −0.53 | −2.13 | <0.0001 | −2.36 | <0.0001 |
| 10 | −0.66 | −2.19 | <0.0001 | −2.39 | <0.0001 |
| 11 | −0.67 | −2.17 | <0.0001 | −2.45 | <0.0001 |
| 12 | −0.75 | −2.38 | <0.0001 | −2.59 | <0.0001 |
| 13 | −0.86 | −2.46 | <0.0001 | −2.67 | <0.0001 |
| 14 | −0.86 | −2.56 | <0.0001 | −2.78 | <0.0001 |
| 15 | −0.91 | −2.54 | <0.0001 | −2.92 | <0.0001 |
| 16 | −1.00 | −2.58 | <0.0001 | −2.97 | <0.0001 |
| 17 | −0.96 | −2.63 | <0.0001 | −2.93 | <0.0001 |
| 18 | −0.94 | −2.68 | <0.0001 | −3.03 | <0.0001 |
| 19 | −1.04 | −2.64 | <0.0001 | −3.09 | <0.0001 |
| 20 | −1.08 | −2.66 | <0.0001 | −3.11 | <0.0001 |
| 21 | −0.99 | −2.75 | <0.0001 | −3.02 | <0.0001 |
| 22 | −1.09 | −2.78 | <0.0001 | −3.18 | <0.0001 |
| 23 | −0.97 | −2.74 | <0.0001 | −3.05 | <0.0001 |
| 24 | −1.01 | −2.78 | <0.0001 | −3.05 | <0.0001 |
| 25 | −1.05 | −2.78 | <0.0001 | −3.17 | <0.0001 |
| 26 | −0.95 | −2.79 | <0.0001 | −3.11 | <0.0001 |
| 27 | −1.06 | −2.75 | <0.0001 | −3.06 | <0.0001 |
| 28 | −1.06 | −2.85 | <0.0001 | −3.16 | <0.0001 |

In patients having baseline itch NRS score of ≥2, the number of responders reaching a ≥2-point improvement in itch NRS score became statistically significant by day 2 (within 36 hours of the first application of ruxolitinib cream) for patients receiving 0.75% and 1.5% BID ruxolitinib cream (Table 19 (TRuE-AD1) and Table 20 (TRuE-AD2).

TABLE 19

Participants achieving a ≥2-point reduction in itch NRS score - Number of responders out of total (%)

| Day | Vehicle | 0.75% BID | p-value | 1.5% BID | p-value |
|---|---|---|---|---|---|
| 1 | 9 of 96 (9.4%) | 31 of 201 (15.4%) | 0.2030 | 28 of 207 (13.5%) | 0.4099 |
| 2 | 8 of 95 (8.4%) | 64 of 197 (32.5%) | <0.0001 | 78 of 199 (39.2%) | <0.0001 |
| 3 | 16 of 97 (16.5%) | 72 of 195 (36.9%) | 0.0003 | 91 of 199 (45.7%) | <0.0001 |
| 4 | 13 of 95 (13.7%) | 96 of 199 (48.2%) | <0.0001 | 105 of 198 (53.0%) | <0.0001 |
| 5 | 12 of 94 (12.8%) | 92 of 193 (47.7%) | <0.0001 | 115 of 198 (58.1%) | <0.0001 |
| 6 | 22 of 92 (23.9%) | 99 of 192 (51.6%) | <0.0001 | 121 of 203 (59.6%) | <0.0001 |
| 7 | 19 of 93 (20.4%) | 101 of 194 (52.1%) | <0.0001 | 116 of 203 (57.4%) | <0.0001 |
| 8 | 20 of 91 (22.0%) | 108 of 194 (55.7%) | <0.0001 | 116 of 200 (58.0%) | <0.0001 |
| 9 | 23 of 91 (25.3%) | 115 of 188 (61.2%) | <0.0001 | 115 of 197 (58.4%) | <0.0001 |
| 10 | 23 of 90 (25.6%) | 110 of 188 (58.5%) | <0.0001 | 123 of 191 (64.4%) | <0.0001 |
| 11 | 24 of 87 (27.6%) | 110 of 179 (61.5%) | <0.0001 | 121 of 187 (64.7%) | <0.0001 |
| 12 | 24 of 89 (27.0%) | 121 of 188 (64.4%) | <0.0001 | 119 of 184 (64.7%) | <0.0001 |
| 13 | 28 of 91 (30.8%) | 119 of 193 (61.7%) | <0.0001 | 129 of 193 (66.8%) | <0.0001 |
| 14 | 26 of 92 (28.3%) | 124 of 189 (65.6%) | <0.0001 | 134 of 196 (68.4%) | <0.0001 |

TABLE 20

Participants achieving a ≥2-point reduction in itch NRS score - Number of responders out of total (%)

| Day | Vehicle | 0.75% BID | p-value | 1.5% BID | p-value |
|---|---|---|---|---|---|
| 1 | 4 of 92 (4.3%) | 30 of 174 (17.2%) | 0.0032 | 22 of 175 (12%) | 0.0447 |
| 2 | 7 of 91 (7.7%) | 51 of 180 (28.3%) | <0.0001 | 51 of 172 (29.7%) | <0.0001 |
| 3 | 12 of 88 (13.6%) | 59 of 174 (33.9%) | 0.0004 | 64 of 170 (37.6%) | <0.0001 |
| 4 | 10 of 88 (11.4%) | 59 of 166 (35.5%) | <0.0001 | 81 of 172 (47.1%) | <0.0001 |
| 5 | 12 of 89 (13.5%) | 76 of 172 (44.2%) | <0.0001 | 80 of 170 (47.1%) | <0.0001 |
| 6 | 10 of 87 (11.5%) | 81 of 167 (48.5%) | <0.0001 | 82 of 170 (48.2%) | <0.0001 |
| 7 | 13 of 92 (14.1%) | 89 of 172 (51.7%) | <0.0001 | 94 of 175 (53.7%) | <0.0001 |
| 8 | 13 of 90 (14.4%) | 96 of 174 (55.2%) | <0.0001 | 97 of 171 (56.7%) | <0.0001 |
| 9 | 13 of 84 (15.5%) | 94 of 170 (55.3%) | <0.0001 | 88 of 165 (53.3%) | <0.0001 |
| 10 | 18 of 90 (20.0%) | 93 of 166 (56.0%) | <0.0001 | 95 of 165 (57.6%) | <0.0001 |
| 11 | 17 of 87 (20.2%) | 94 of 174 (54.0%) | <0.0001 | 94 of 167 (56.3%) | <0.0001 |
| 12 | 21 of 90 (23.3%) | 100 of 172 (58.1%) | <0.0001 | 104 of 164 (63.4%) | <0.0001 |
| 13 | 20 of 86 (23.3%) | 100 of 167 (59.9%) | <0.0001 | 102 of 166 (61.4%) | <0.0001 |
| 14 | 24 of 88 (27.3%) | 105 of 170 (61.8%) | <0.0001 | 107 of 170 (62.9%) | <0.0001 |

In patients having baseline itch NRS score of ≥2, the number of responders reaching a ≥2-point improvement in itch NRS score became statistically significant by day 2 (within 36 hours of the first application of ruxolitinib cream) for patients receiving 0.75% and 1.5% BID ruxolitinib cream (Table 21 (TRuE-AD1 and TRuE-AD2)). The difference between 0.75% and 1.5% ruxolitinib cream versus vehicle became statistically significant at day 1 (within 12 hours).

TABLE 21

Participants achieving a ≥2-point reduction in itch NRS score - Number of responders out of total (%)

| Day | Vehicle | 0.75% BID | p-value | 1.5% BID | p-value |
|---|---|---|---|---|---|
| 1 | 13 of 188 (0.7%) | 61 of 375 (2.7%) | 0.0021 | 50 of 382 (3.1%) | 0.0300 |
| 2 | 15 of 186 (8.1%) | 115 of 377 (30.5%) | <0.0001 | 129 of 371 (34.8%) | <0.0001 |
| 3 | 28 of 185 (15.1%) | 131 of 369 (35.5%) | <0.0001 | 155 of 369 (42.0%) | <0.0001 |
| 4 | 23 of 183 (12.6%) | 155 of 365 (42.5%) | <0.0001 | 186 of 370 (50.3%) | <0.0001 |
| 5 | 24 of 183 (13.1%) | 168 of 365 (46.0%) | <0.0001 | 195 of 368 (53.0%) | <0.0001 |
| 6 | 32 of 179 (17.9%) | 180 of 359 (50.1%) | <0.0001 | 203 of 373 (54.4%) | <0.0001 |
| 7 | 32 of 185 (17.3%) | 190 of 366 (51.9%) | <0.0001 | 210 of 377 (55.7%) | <0.0001 |

Figure 26:
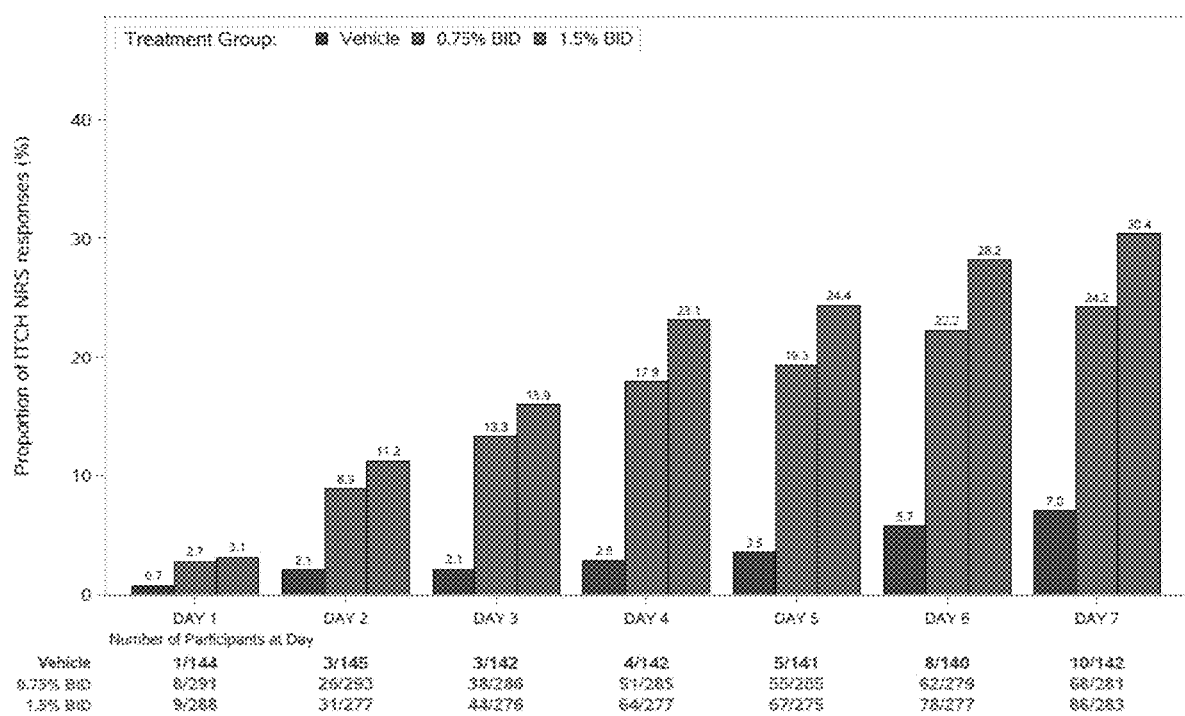
FIG. 26 depicts proportion of patients achieving an itch NRS score of ≥4-point improvement in itch NRS score for day 1 to day 7 (patients having a baseline itch NRS score of ≥4) for the pooled TRuE-AD1 (Study 303) and TRuE-AD2 (Study 304) studies (first bar (vehicle), second bar (0.75% BID ruxolitinib cream), and third bar (1.5% BID ruxolitinib cream).

In patients having baseline itch NRS score of ≥4, the number of responders reaching a ≥4-point improvement in itch NRS score became statistically significant by day 4 of the first application of ruxolitinib cream for patients receiving 0.75% BID ruxolitinib cream and by day 3 of the first application of ruxolitinib cream for patients receiving 1.5% BID ruxolitinib cream (Table 22 (TRuE-AD1 and TRuE-AD2 and FIG. 26)).

TABLE 22

Participants achieving a ≥4-point reduction in itch NRS score - Number of responders out of total (%)

| Day | Vehicle | 0.75% BID | p-value | 1.5% BID | p-value |
|---|---|---|---|---|---|
| 1 | 1 of 144 (0.7%) | 8 of 291 (2.7%) | 0.0807 | 9 of 288 (3.1%) | 0.1290 |
| 2 | 3 of 145 (2.1%) | 26 of 293 (8.9%) | 0.0042 | 31 of 277 (11.2%) | 0.0012 |
| 3 | 3 of 142 (2.1%) | 38 of 286 (13.3%) | 0.0002 | 44 of 276 (15.9%) | <0.0001 |
| 4 | 4 of 142 (2.8%) | 51 of 285 (17.9%) | <0.0001 | 64 of 277 (23.1%) | <0.0001 |
| 5 | 5 of 141 (3.5%) | 55 of 285 (19.3%) | <0.0001 | 67 of 275 (24.4%) | <0.0001 |
| 6 | 8 of 140 (5.7%) | 62 of 279 (22.2%) | <0.0001 | 78 of 277 (28.2%) | <0.0001 |
| 7 | 10 of 142 (7.0%) | 68 of 281 (24.2%) | <0.0001 | 86 of 283 (30.4%) | <0.0001 |

Patients achieve an IGA score of 0 or 1 by Week 2 for patients receiving 0.75% and 1.5% BID ruxolitinib cream on TRuE-AD1 study (Table 23). Patients achieve an IGA score of 0 or 1 by Week 2 for patients receiving 1.5% BID ruxolitinib cream and by Week 4 for patients receiving 0.75% BID ruxolitinib cream on TRuE-AD2 study (Table 24).

Figure 17:
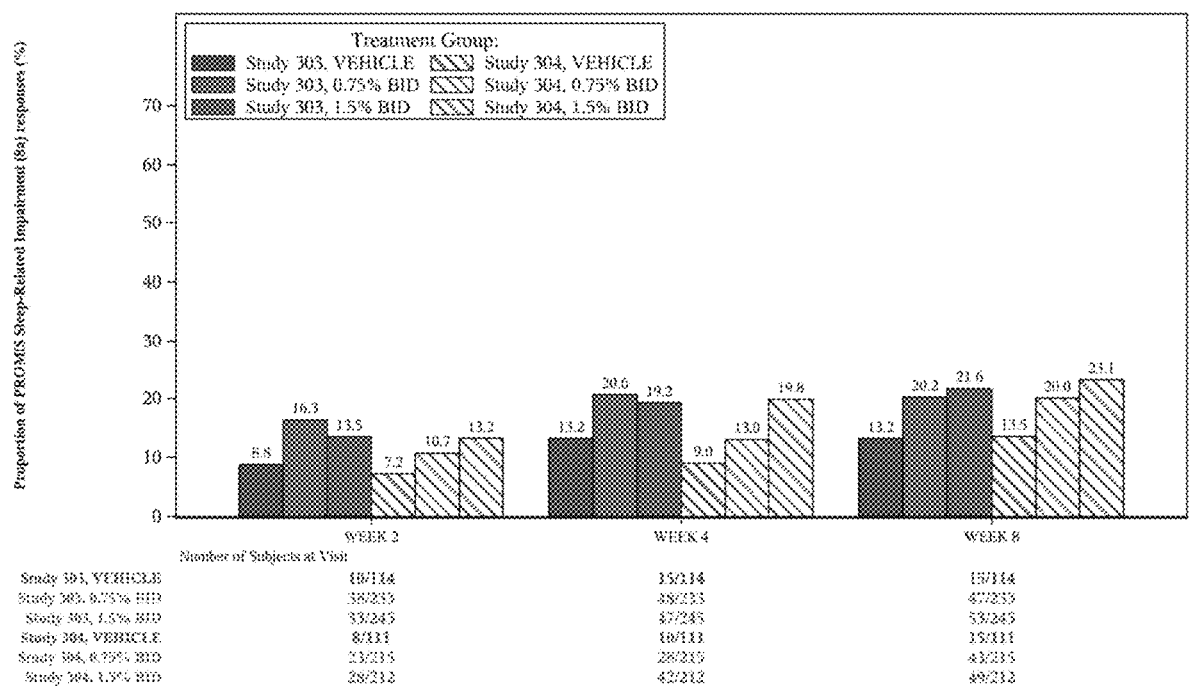
FIG. 17 depicts the proportion of participants that achieved a ≥6-point improvement in the PROMIS sleep impairment score (8a) in the vehicle control period at Week 2, Week 4, and Week 8 for TRuE-AD1 (Study 303) (solid bars) and TRuE-AD2 (Study 304) (striped bars) for vehicle, 0.75% BID ruxolitinib cream, and 1.5% BID ruxolitinib cream (first bar of each set is vehicle; second bar of each set is 0.75% BID ruxolitinib cream; and third bar of each set is 1.5% ruxolitinib cream).
Figure 18:
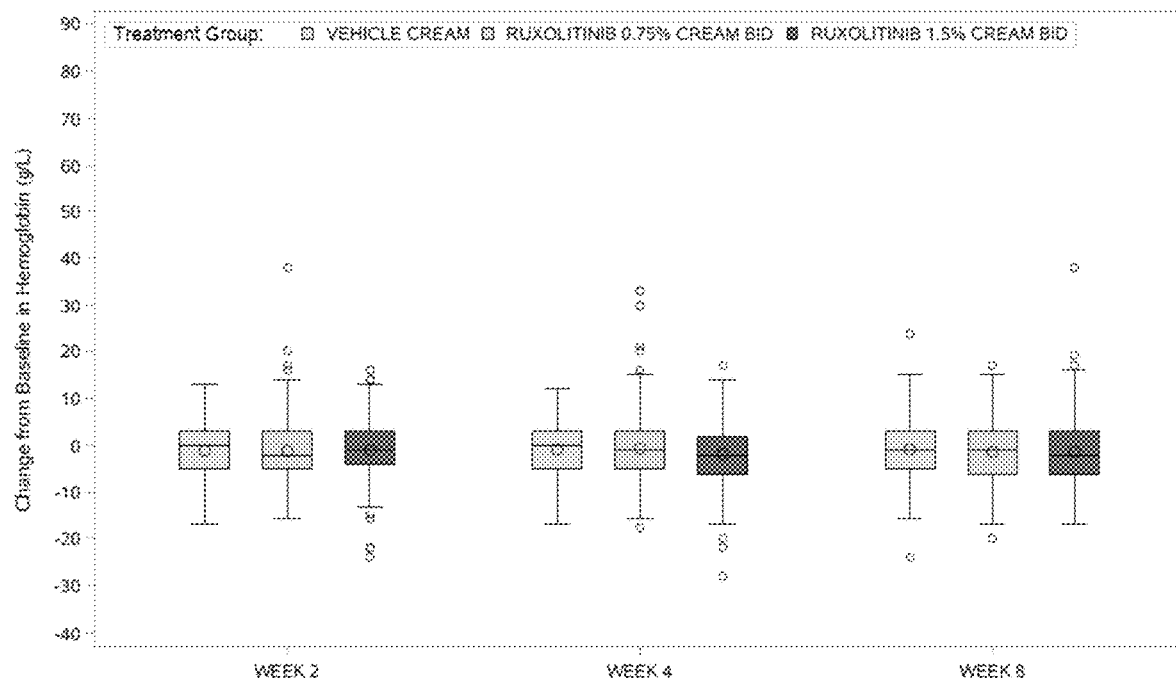
FIG. 18 shows a box plot of change from baseline in hemoglobin (g/L) in the vehicle control period at Week 2, Week 4, and Week 8 for TRuE-AD1 (Study 303) for vehicle, 0.75% BID ruxolitinib cream, and 1.5% BID ruxolitinib cream (first bar of each set is vehicle; second bar of each set is 0.75% BID ruxolitinib cream; and third bar of each set is 1.5% ruxolitinib cream).
Figure 19:
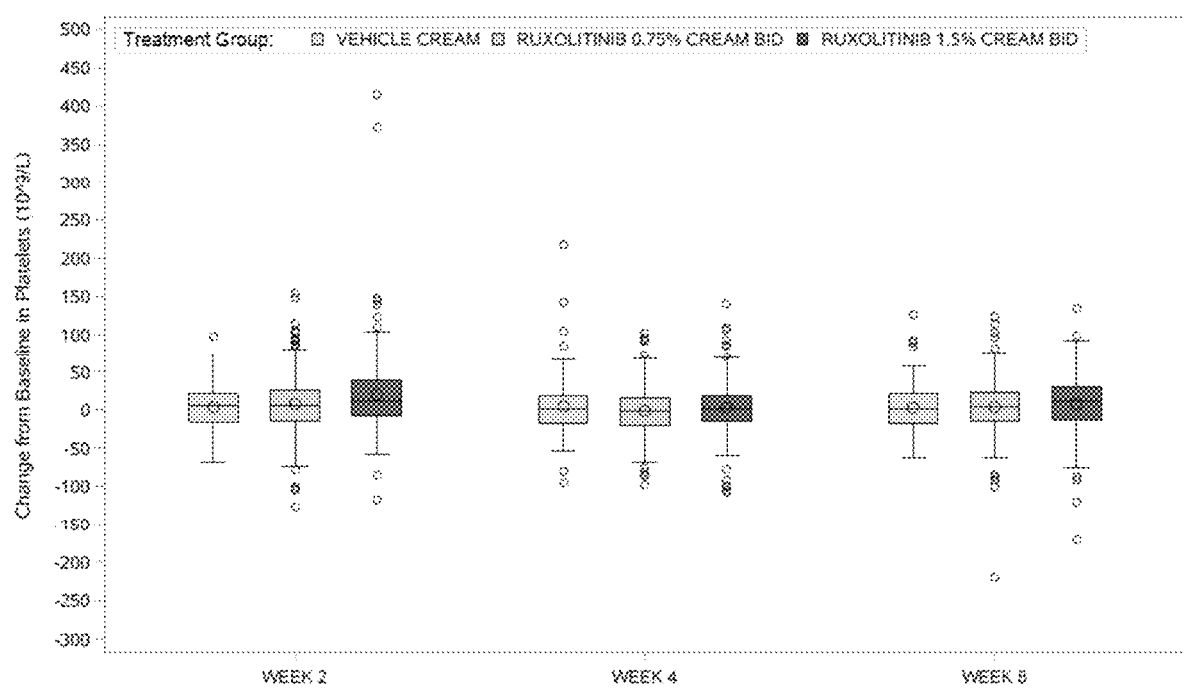
FIG. 19 shows a box plot of change from baseline in platelets ($10^9$/L) in the vehicle control period at Week 2, Week 4, and Week 8 for TRuE-AD1 (Study 303) for vehicle, 0.75% BID ruxolitinib cream, and 1.5% BID ruxolitinib cream (first bar of each set is vehicle; second bar of each set is 0.75% BID ruxolitinib cream; and third bar of each set is 1.5% ruxolitinib cream).
Figure 20:
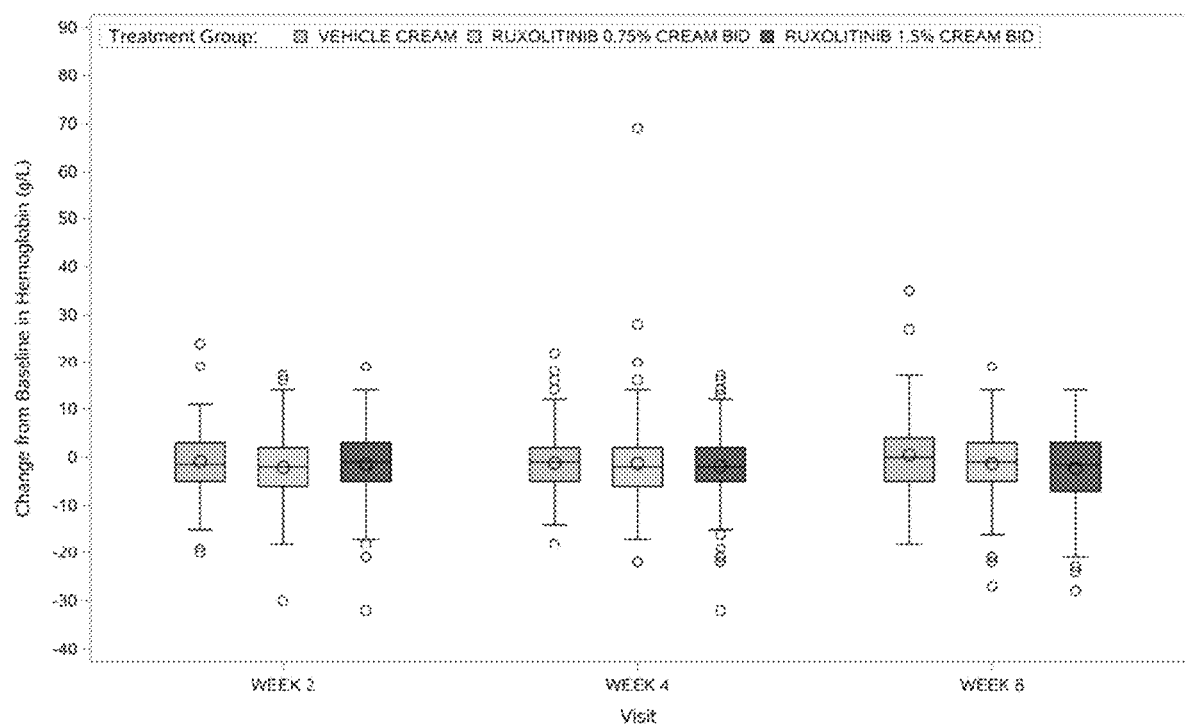
FIG. 20 shows a box plot of change from baseline in hemoglobin (g/L) in the vehicle control period at Week 2, Week 4, and Week 8 for TRuE-AD2 (Study 304) for vehicle, 0.75% BID ruxolitinib cream, and 1.5% BID ruxolitinib cream (first bar of each set is vehicle; second bar of each set is 0.75% BID ruxolitinib cream; and third bar of each set is 1.5% ruxolitinib cream).
Figure 21:
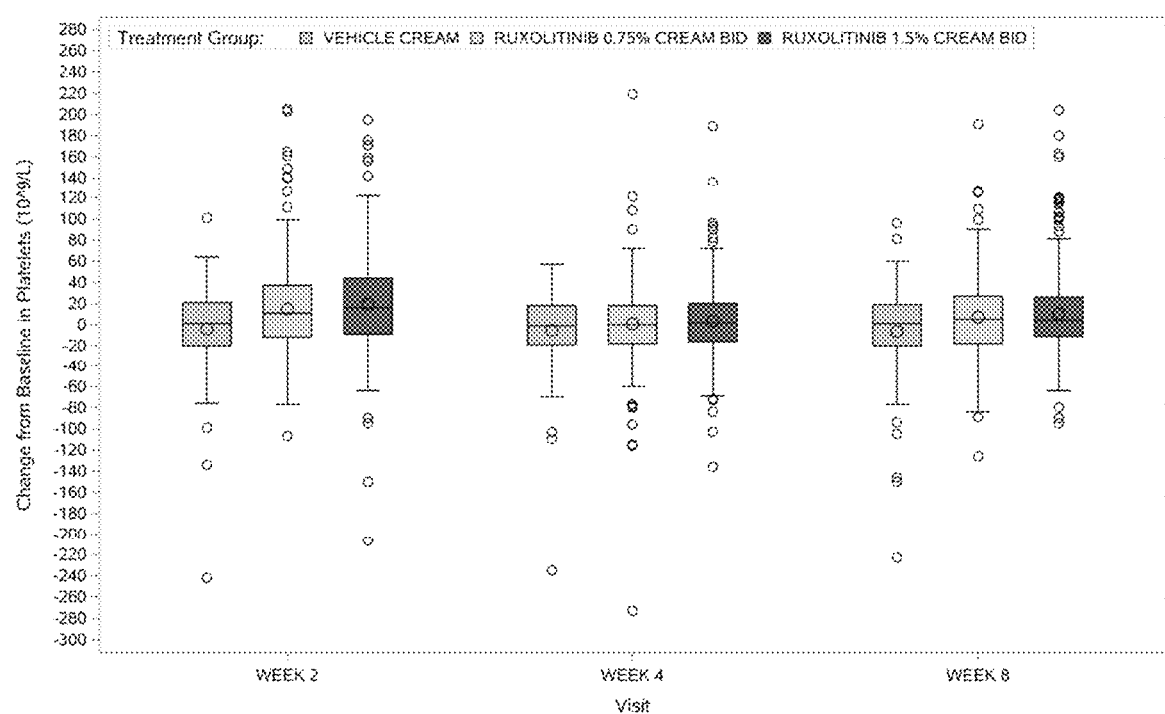
FIG. 21 shows a box plot of change from baseline in platelets ($10^9$/L) in the vehicle control period at Week 2, Week 4, and Week 8 for TRuE-AD2 (Study 304) for vehicle, 0.75% BID ruxolitinib cream, and 1.5% BID ruxolitinib cream (first bar of each set is vehicle; second bar of each set is 0.75% BID ruxolitinib cream; and third bar of each set is 1.5% ruxolitinib cream).
Figure 29:
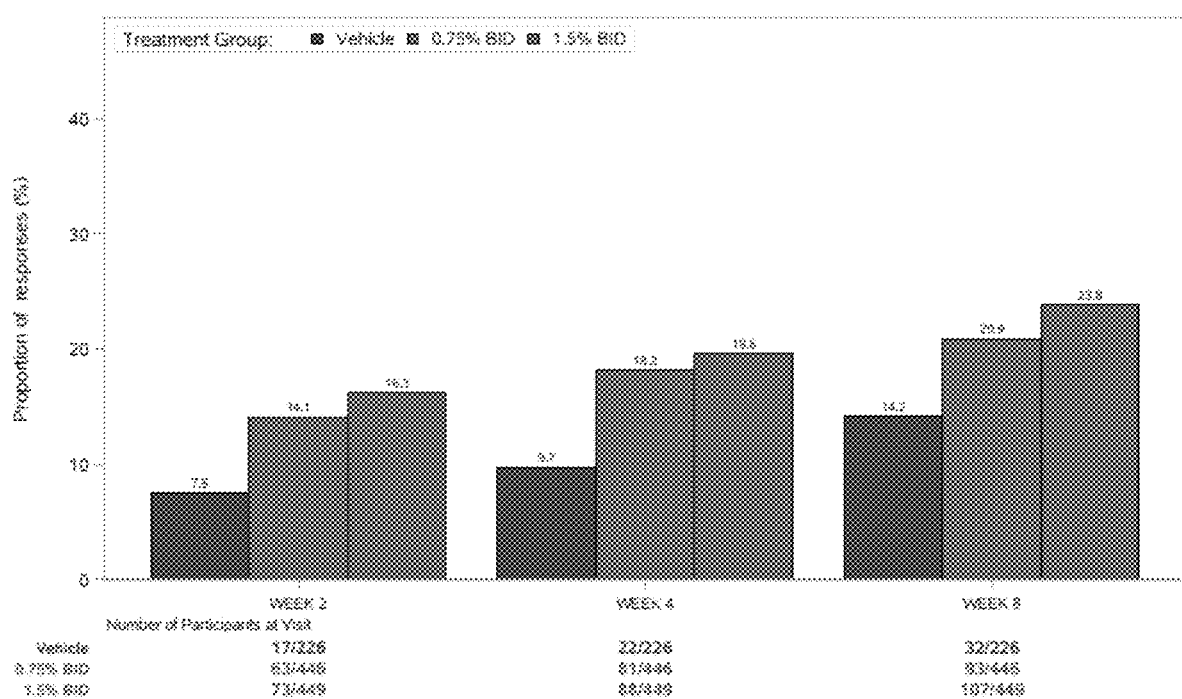
FIG. 29 depicts the proportion of participants that achieved ≥6-Point Improvement in the PROMIS Sleep Disturbance Score (8b) in the vehicle control period at Week 2, Week 4, and Week 8 for patients who have a PROMIS Sleep Disturbance Score (8b) ≥6 at baseline for the pooled TRuE-AD1(Study 303) and TRuE-AD2 (Study 304) for vehicle, 0.75% BID ruxolitinib cream, and 1.5% BID ruxolitinib cream (first bar of each set is vehicle; second bar of each set is 0.75% BID ruxolitinib cream; and third bar of each set is 1.5% ruxolitinib cream).

TRuE-AD1 and TRuE-AD2, respectively (FIG. 17). At Week 8, a ≥6-point improvement in the PROMIS sleep disturbance score (8a) was reached by 20.9% of patients applying ruxolitinib cream 0.75% BID and 23.8% of patients applying ruxolitinib cream 1.5% BID for the pooled TRuE-AD1(Study 303) and TRuE-AD2 (Study 304) (FIG. 29).

TABLE 23

Participants achieving achieve an IGA score of 0 or 1 - Number of responders out of total (%)

| Week | Vehicle | 0.75% BID | p-value | 1.5% BID | p-value |
|---|---|---|---|---|---|
| 2 | 8 of 126 (6.3%) | 82 of 252 (32.5%) | <0.0001 | 88 of 253 (34.8%) | <0.0001 |
| 4 | 19 of 126 (15.1%) | 134 of 252 (53.2%) | <0.0001 | 139 of 253 (54.9%) | <0.0001 |
| 8 | 30 of 126 (23.8%) | 148 of 252 (58.7%) | <0.0001 | 159 of 253 (62.8%) | <0.0001 |

TABLE 24

Participants achieving achieve an IGA score of 0 or 1 - Number of responders out of total (%)

| Week | Vehicle | 0.75% BID | p-value | 1.5% BID | p-value |
|---|---|---|---|---|---|
| 2 | 11 of 118 (9.3%) | 56 of 231 (24.2%) | 0.0008 | 79 of 228 (34.6%) | <0.0001 |
| 4 | 20 of 118 (16.9%) | 106 of 231 (45.9%) | <0.0001 | 120 of 228 (52.6%) | <0.0001 |
| 8 | 19 of 118 (16.1%) | 118 of 231 (51.1%) | <0.0001 | 142 of 228 (62.3%) | <0.0001 |

Patients achieve EASI90 for patients receiving 0.75% and 1.5% BID ruxolitinib cream (Table 25 (TRuE-AD1) and Table 26 (TRuE-AD2). The difference between 0.75% and 1.5% ruxolitinib cream versus vehicle was statistically significant by week 2.

With respect to the 0.75% BID ruxolitinib cream, the patient responses in IGA-TS and EASI75 were unexpectedly improved at weeks 2, 4, and 8, compared to the 1.5% QD ruxolitinib cream (from Phase 2) (see Tables 27 and 28).

TABLE 25

Participants achieving achieve EASI90 - Number of responders out of total (%)

| Week | Vehicle | 0.75% BID | p-value | 1.5% BID | p-value |
|---|---|---|---|---|---|
| 2 | 3 of 126 (2.4%) | 32 of 252 (12.7%) | 0.0008 | 50 of 253 (19.8%) | <0.0001 |
| 4 | 5 of 126 (4.0%) | 77 of 252 (30.6%) | <0.0001 | 92 of 253 (36.4%) | <0.0001 |
| 8 | 12 of 126 (9.5%) | 96 of 252 (38.1%) | <0.0001 | 112 of 253 (44.3%) | <0.0001 |

TABLE 26

Participants achieving achieve EASI90 - Number of responders out of total (%)

| Week | Vehicle | 0.75% BID | p-value | 1.5% BID | p-value |
|---|---|---|---|---|---|
| 2 | 1 of 118 (0.8%) | 25 of 231 (10.8%) | 0.0004 | 36 of 228 (15.8%) | <0.0001 |
| 4 | 3 of 118 (2.5%) | 59 of 231 (25.5%) | <0.0001 | 74 of 228 (32.5%) | <0.0001 |
| 8 | 5 of 118 (4.2%) | 81 of 231 (35.1%) | <0.0001 | 99 of 228 (43.4%) | <0.0001 |

Figure 16:
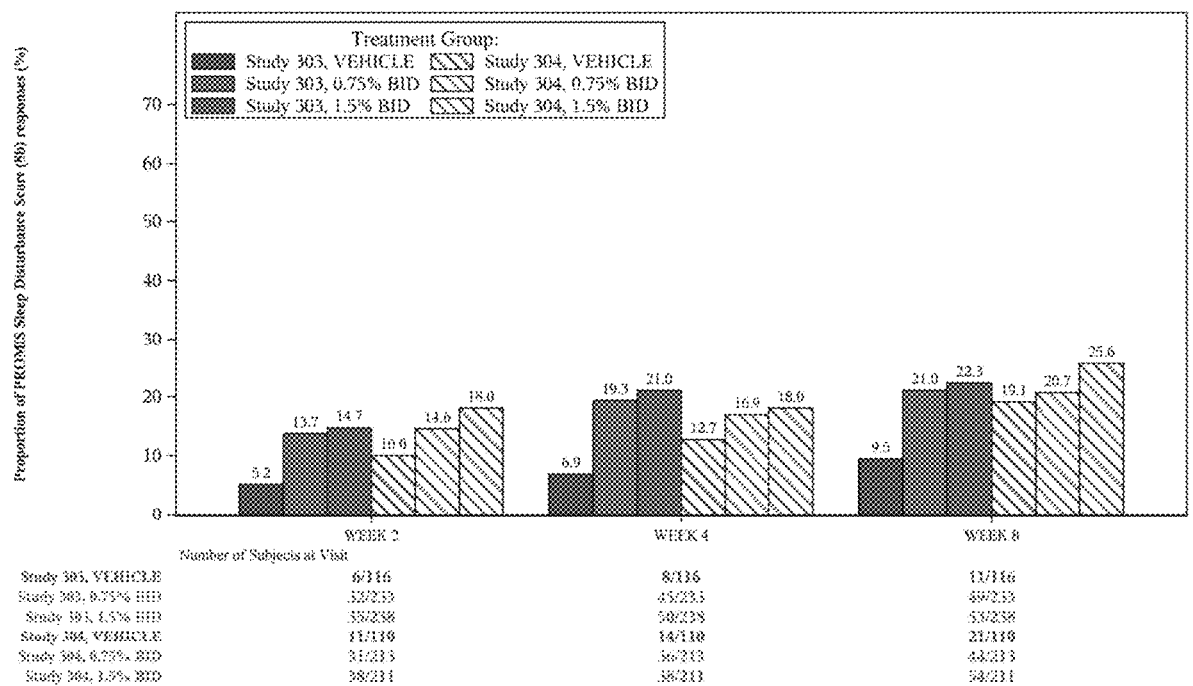
FIG. 16 depicts the proportion of participants that achieved a ≥6-point improvement in the PROMIS sleep disturbance score (8b) in the vehicle control period at Week 2, Week 4, and Week 8 for TRuE-AD1 (Study 303) (solid bars) and TRuE-AD2 (Study 304) (striped bars) for vehicle, 0.75% BID ruxolitinib cream, and 1.5% BID ruxolitinib cream (first bar of each set is vehicle; second bar of each set is 0.75% BID ruxolitinib cream; and third bar of each set is 1.5% ruxolitinib cream).
Figure 30:
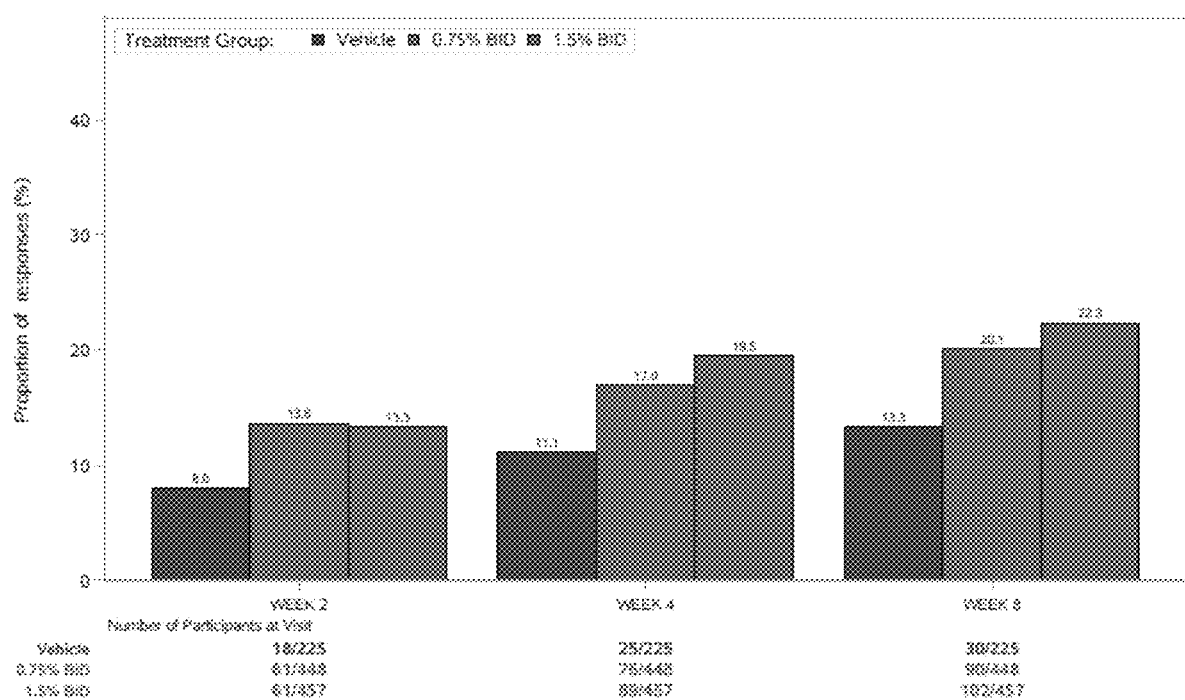
FIG. 30 depicts the proportion of participants that achieved ≥6-Point Improvement in the PROMIS Sleep-Related Impairment (8a) in the vehicle control period at Week 2, Week 4, and Week 8 for patients who have a PROMIS Sleep-Related Impairment (8a) ≥6 at baseline for the pooled TRuE-AD1(Study 303) and TRuE-AD2 (Study 304) for vehicle, 0.75% BID ruxolitinib cream, and 1.5% BID ruxolitinib cream (first bar of each set is vehicle; second bar of each set is 0.75% BID ruxolitinib cream; and third bar of each set is 1.5% ruxolitinib cream).

At Week 8, a ≥6-point improvement in the PROMIS sleep impairment score (8a) was reached by 21.0% and 20.7% of patients applying ruxolitinib cream 0.75% BID and 22.3% and 25.6% of patients applying ruxolitinib cream 1.5% BID for TRuE-AD1 and TRuE-AD2, respectively (FIG. 16). At Week 8, a ≥6-point improvement in the PROMIS sleep impairment score (8a) was reached by 20.1% of patients applying ruxolitinib cream 0.75% BID and 22.3% of patients applying ruxolitinib cream 1.5% BID for the pooled TRuE-AD1(Study 303) and TRuE-AD2 (FIG. 30). At Week 8, a ≥6-point improvement in the PROMIS sleep disturbance score (8a) was reached by 20.2% and 20.0% of patients applying ruxolitinib cream 0.75% BID and 21.6% and 23.1% of patients applying ruxolitinib cream 1.5% BID for

TABLE 27

Proportion of patient that achieve IGA-TS (%)

| Week | 0.75% BID[a] | 1.5% QD[b] | 1.5% BID[a] | 1.5% BID[b] |
|---|---|---|---|---|
| 2 | 30.6 | 13.5 | 25.0 | 8.0 |
| 4 | 38.9 | 21.2 | 46.9 | 38.0 |
| 8 | 50.0 | 30.8 | 59.4 | 48.0 |

Figure 22:
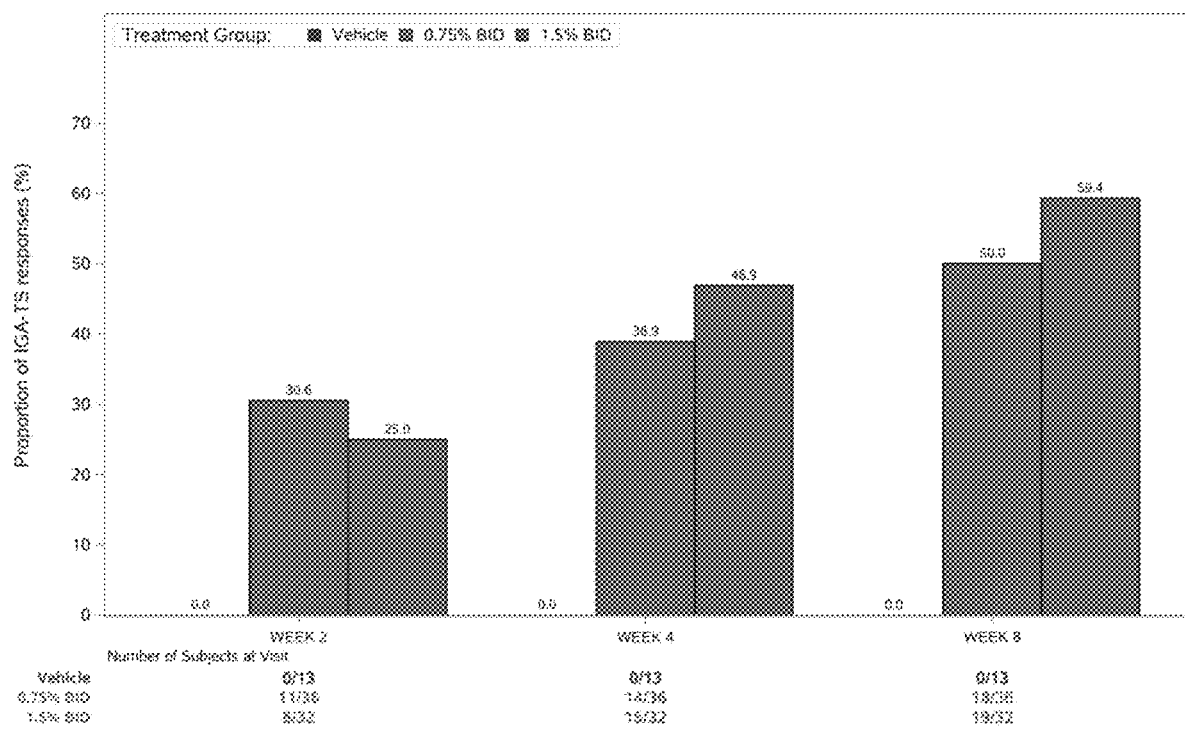
FIG. 22 depicts the proportion of participants that achieved IGA-TS in the vehicle control period at Week 2, Week 4, and Week 8 for patients who have a Body Surface Area of atopic dermatitis involvement of ≥10% at baseline and an Eczema Area and Severity Index score of ≥16 at baseline in both TRuE-AD1 (Study 303) and TRuE-AD2 (Study 304) for vehicle, 0.75% BID ruxolitinib cream, and 1.5% BID ruxolitinib cream (first bar of each set is vehicle; second bar of each set is 0.75% BID ruxolitinib cream; and third bar of each set is 1.5% ruxolitinib cream).

[a]See FIG. 22 (Phase 3 results)
[b]See FIG. 4 (Phase 2 results)

TABLE 28

Proportion of patient that achieve EASI75 (%)

| Week | 0.75% BID[a] | 1.5% QD[b] | 1.5% BID[a] | 1.5% BID[b] |
|---|---|---|---|---|
| 2 | 36.1 | 21.2 | 37.5 | 30.0 |
| 4 | 63.9 | 40.4 | 53.3 | 56.0 |
| 8 | 75.0 | 53.8 | 71.9 | 64.0 |

Figure 3:
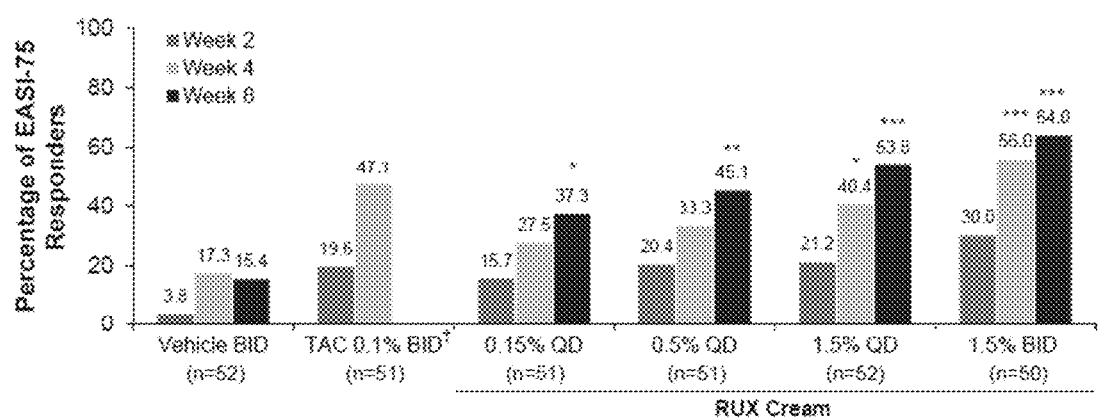
FIG. 3 shows a graph of percentage of EASI-75 responders (at least a 75% improvement in EASI from baseline) for vehicle (BID), triamcinolone (0.1% BID), and ruxolitinib cream (0.15% QD, 0.5% QD, 1.5% QD, and 1.5% BID) at week 2 (first graph bar of each set), week 4 (second graph bar of each set) and week 8 (third graph bar of each set). 0.1% TAC does not show a bar because TAC was only administered for 4 weeks.
Figure 23:
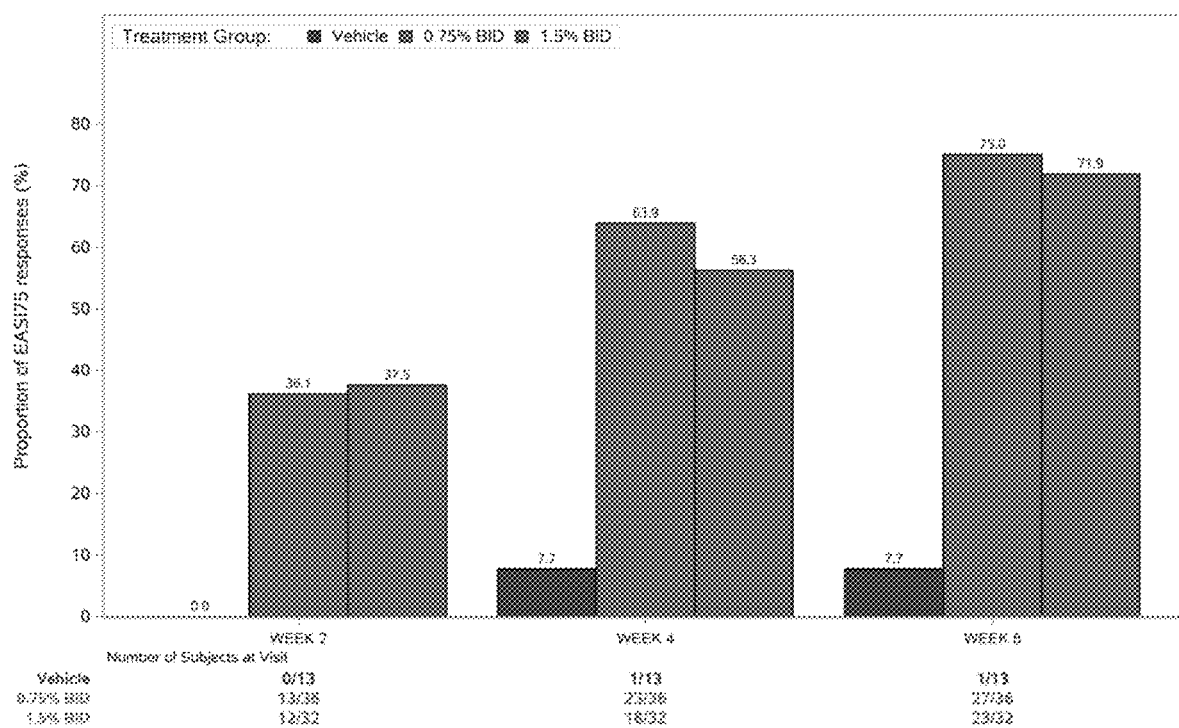
FIG. 23 depicts the proportion of participants that achieved EASI-75 in the vehicle control period at Week 2, Week 4, and Week 8 for the patients who a Body Surface Area of atopic dermatitis involvement of ≥10% at baseline and an Eczema Area and Severity Index score of ≥16 at baseline in both TRuE-AD1(Study 303) and TRuE-AD2 (Study 304) for vehicle, 0.75% BID ruxolitinib cream, and 1.5% BID ruxolitinib cream (first bar of each set is vehicle; second bar of each set is 0.75% BID ruxolitinib cream; and third bar of each set is 1.5% ruxolitinib cream).

[a] See FIG. 23 (Phase 3 results)
[b] See FIG. 3 (Phase 2 results)

The overall rate of treatment-emergent adverse events in both studies after 8 weeks of treatment was comparable between the ruxolitinib cream regimens and vehicle (0.75% BID, 29.4%; 1.5% BID, 28.9%; vehicle, 34.9% in TRuE-AD1; and 0.75% BID, 29.4%; 1.5% BID, 23.6%; vehicle, 32.3% in TRuE-AD2). The rate of serious adverse events wascomparable in all treatment groups (0.75% BID, 0.8%; 1.5% BID, 0.6%; vehicle, 0.8%). No clinically significant application site reactions were observed, including areas of sensitive skin. For example, application site burn occurred at comparable or lower rates than for vehicle (0.75% BID, 0.0%; 1.5% BID, 0.8%; vehicle, 1.6% in TRuE-AD1; and 0.75% BID, 0.8%; 1.5% BID, 0.8%; vehicle, 6.5% in TRuE-AD2). Application site pruritus occurred at comparable or lower rates than for vehicle (0.75% BID, 1.2%; 1.5% BID, 0.0%; vehicle, 1.6%). Changes in hemoglobin (g/L) and platelets ($10^9$/L) over 8 weeks were comparable between the treatment groups (0.75% BID and 1.5% BID) versus vehicle (FIG. 18-21).

Patients with More Severe Atopic Dermatitis with Higher Body Surface Involvement Strikingly, it was found that patients with more severe atopic dermatitis with higher body surface involvement appeared to respond well to topical ruxolitinib cream in the TRuE-AD1 and TRuE-AD2 studies. These patients generally have a Body Surface Area of atopic dermatitis involvement of ≥10% at baseline and an Eczema Area and Severity Index score of ≥16 at baseline.

An analysis was conducted for TRuE-AD1 and TRuE-AD2 patients having a Body Surface Area of atopic dermatitis involvement of ≥10% at baseline and an Eczema Area and Severity Index score of ≥16 at baseline. Of the 81 patients in the subgroup, there were 13 patients receiving vehicle, 36 patients receiving 0.75% BID ruxolitinib cream, and 32 patients receiving 1.5% BID cream. 100% of patients receiving vehicle and 1.5% BID ruxolitinib cream had an IGA score of 3 at baseline, while 33 of 36 patients receiving 0.75% BID ruxolitinib cream had an IGA score of 3 at baseline with the remaining patients having an IGA score of 2 at baseline.

In both TRuE-AD1 and TRuE-AD2, for patients who have a Body Surface Area of atopic dermatitis involvement of ≥10% at baseline and an Eczema Area and Severity Index score of ≥16 at baseline, more patients treated with ruxolitinib cream achieved IGA treatment success in the vehicle control period at Week 2, Week 4, and Week 8 (0.75% BID, 30.6%, 38.9%, and 50.0%; 1.5% BID, 25.0%, 46.9% and 59.4%) vs vehicle (0.0%) (FIG. 22).

Figure 27:
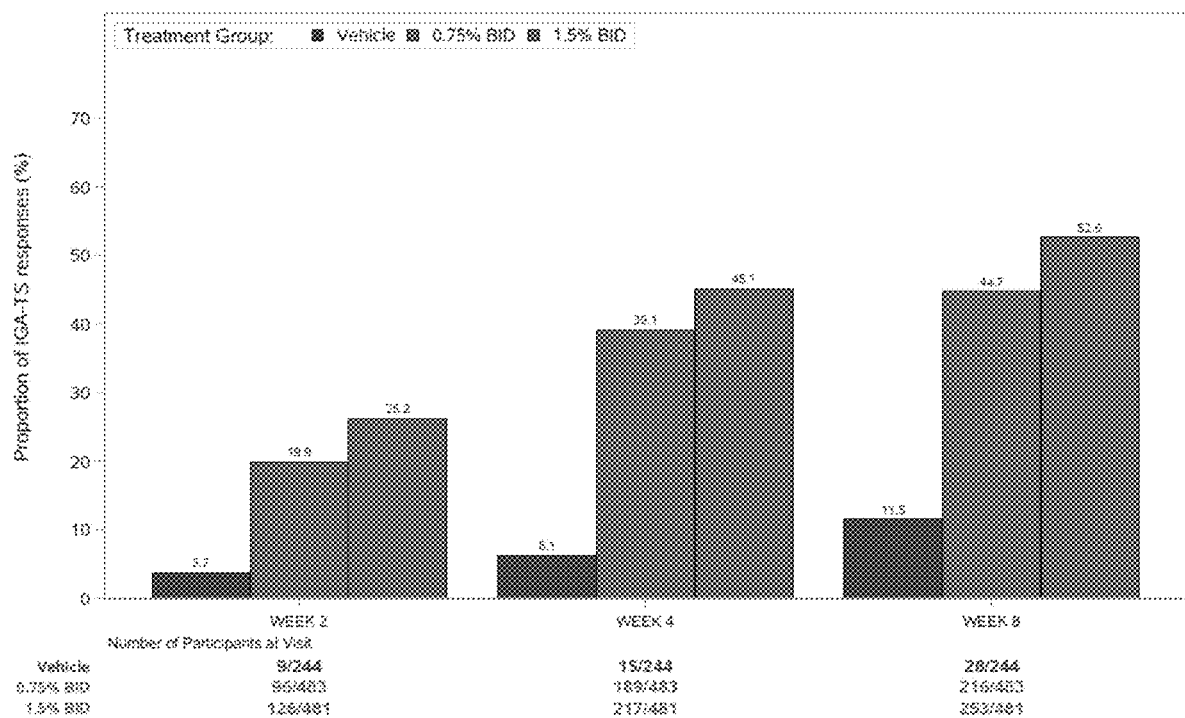
FIG. 27 depicts the proportion of participants that achieved IGA-TS in the vehicle control period at Week 2, Week 4, and Week 8 for the pooled TRuE-AD1 (Study 303) and TRuE-AD2 (Study 304) studies for vehicle, 0.75% BID ruxolitinib cream, and 1.5% BID ruxolitinib cream (first bar of each set is vehicle; second bar of each set is 0.75% BID ruxolitinib cream; and third bar of each set is 1.5% ruxolitinib cream).

In both TRuE-AD1 and TRuE-AD2, more patients treated with ruxolitinib cream achieved IGA treatment success in the vehicle control period at Week 2, Week 4, and Week 8 (0.75% BID, 19.9%, 39.1%, and 44.7%; 1.5% BID, 26.2%, 45.1% and 52.6%) vs vehicle (3.7%, 6.1%, and 11.5%) (FIG. 27).

In TRuE-AD1 for patients who have an IGA score of 3 at baseline and a Body Surface Area of atopic dermatitis involvement of ≥10% at baseline, more patients treated with ruxolitinib cream achieved IGA treatment success in the vehicle control period at Week 2, Week 4, and Week 8 (0.75% BID, 21.0%, 42.0%, and 53.0%; 1.5% BID, 25.3%, 50.6%, and 60.9%) vs vehicle (0.0%, 4.8%, and 14.3%).

In both TRuE-AD1 and TRuE-AD2, for patients who have a Body Surface Area of atopic dermatitis involvement of ≥10% at baseline and an Eczema Area and Severity Index score of ≥16 at baseline, EASI-75 was achieved by more patients applying ruxolitinib cream 0.75% BID (36.1%, 63.9% and 75.0% at Week 2, Week 4, and Week 8, respectively) and ruxolitinib cream 1.5% BID (37.5%, 56.3%, and 71.9% at Week 2, Week 4, and Week 8, respectively) compared with vehicle (0%, 7.7%, and 7.7% at Week 2, Week 4, and Week 8, respectively) (FIG. 23).

Figure 28:
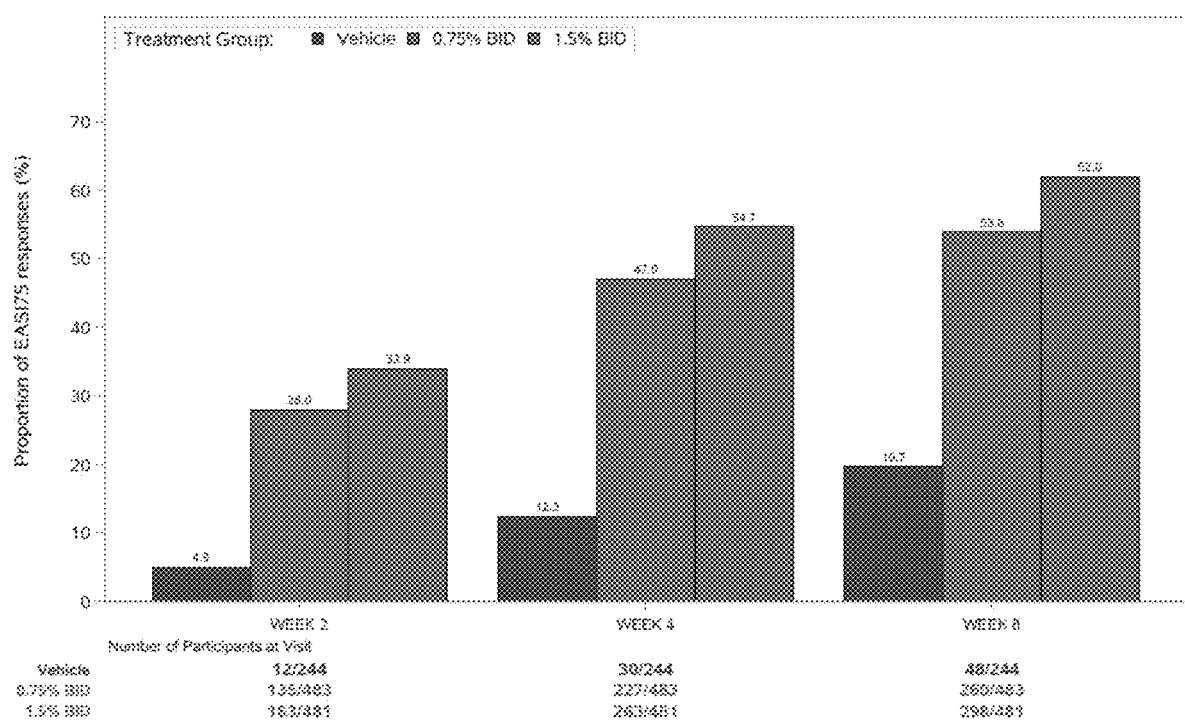
FIG. 28 depicts the proportion of participants that achieved EASI-75 in the vehicle control period at Week 2, Week 4, and Week 8 for the pooled TRuE-AD1(Study 303) and TRuE-AD2 (Study 304) for vehicle, 0.75% BID ruxolitinib cream, and 1.5% BID ruxolitinib cream (first bar of each set is vehicle; second bar of each set is 0.75% BID ruxolitinib cream; and third bar of each set is 1.5% ruxolitinib cream).

In both TRuE-AD1 and TRuE-AD2, EASI-75 was achieved by more patients applying ruxolitinib cream 0.75% BID (28.0%, 47.0% and 53.8% at Week 2, Week 4, and Week 8, respectively) and ruxolitinib cream 1.5% BID (33.9%, 54.7%, and 62.0% at Week 2, Week 4, and Week 8, respectively) compared with vehicle (4.9%, 12.3%, and 19.7% at Week 2, Week 4, and Week 8, respectively) (FIG. 28).

Figure 24:
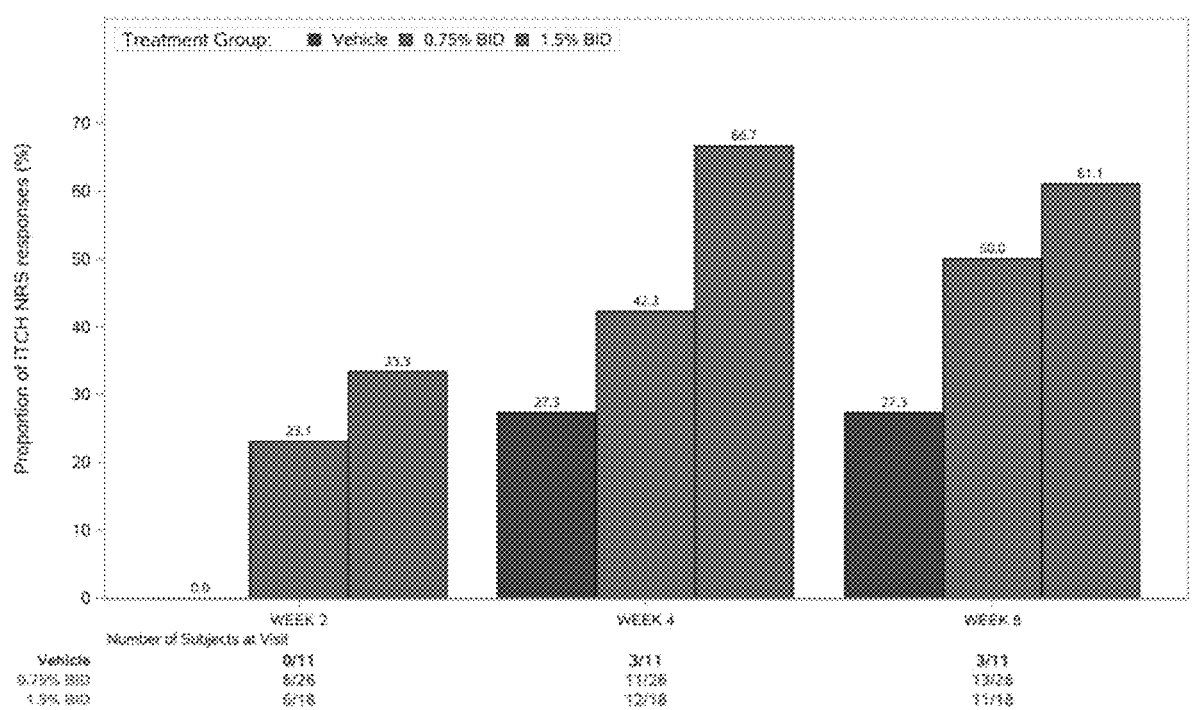
FIG. 24 depicts the proportion of participants that achieved a ≥4-point improvement in itch NRS score in the vehicle control period at Week 2, Week 4, and Week 8 for the patients who a Body Surface Area of atopic dermatitis involvement of ≥10% at baseline, an Eczema Area and Severity Index score of ≥16 at baseline, and an itch Numerical Rating Scale score of ≥4 at baseline in both TRuE-AD1 (Study 303) and TRuE-AD2 (Study 304) for vehicle, 0.75% BID ruxolitinib cream, and 1.5% BID ruxolitinib cream for patients having baseline itch NRS ≥4 (first bar of each set is vehicle; second bar of each set is 0.75% BID ruxolitinib cream; and third bar of each set is 1.5% ruxolitinib cream).

In both TRuE-AD1 and TRuE-AD2, for patients who have a Body Surface Area of atopic dermatitis involvement of ≥10% at baseline, an Eczema Area and Severity Index score of ≥16 at baseline, and an itch Numerical Rating Scale score of ≥4 at baseline, more patients achieved itch reductions (≥4-point improvement in itch NRS score) that applied ruxolitinib cream 0.75% BID (23.1%, 42.3% and 50% at Week 2, Week 4, and Week 8, respectively) and ruxolitinib cream 1.5% BID (33.3%, 66.7%, and 61.1% at Week 2, Week 4, and Week 8, respectively) on 1.5% BID compared with vehicle (0%, 27.3%, and 27.3% at Week 2, Week 4, and Week 8, respectively) (FIG. 24).

Surprisingly, these results show that patients with more severe atopic dermatitis with higher body surface involvement appear to respond comparably or better on topical ruxolitinib cream 0.75% or 1.5% BID than patients treated with a systemic biologic agent like dupilumab (See comparison in Table 29; and FIG. 22-24). These results are particularly surprising given that the responses for ruxolitinib cream were seen as early as 4 to 8 weeks as compared to dupilumab at 16 weeks.

TABLE 29

| | Ruxolitinib cream | | | | Dupilumab[b,c] | |
|---|---|---|---|---|---|---|
| | At Week 4 | | At Week 8 | | At Week 16 | At Week 16 |
| Dosage | 0.75% BID | 1.5% BID | 0.75% BID | 1.5% BID | 300 mg every other week | 300 mg every week |
| Proportion of patients achieving IGA-TS | 38.9% | 46.9% | 50.0% | 59.4% | 36%, 38% | 36%, 37% |

TABLE 29-continued

|  | Ruxolitinib cream | | | | Dupilumab[b,c] | |
| --- | --- | --- | --- | --- | --- | --- |
|  | At Week 4 | | At Week 8 | | At Week 16 | At Week 16 |
| Proportion of patients achieving EASI-75 | 63.9% | 75.0% | 56.3% | 71.9% | 44%, 51% | 48%, 52% |
| Proportion of patient achieving a 4-point improvement in itch NRS score[a] | 42.3% | 50% | 66.7% | 61.1% | 36%, 41% | 39%, 40% |

[a]Patients had an itch NRS score of ≥4 at baseline.
[b]Subcutaneous (Solo1 and Solo2 trials).
[c]Simpson EL, et al. "Two phase 3 trials of dupilumab versus placebo in atopic dermatitis," *N Engl J Med* 2016; 375:2335-48, Table 1.

Various modifications of the invention, in addition to those described herein, will be apparent to those skilled in the art from the foregoing description. Such modifications are also intended to fall within the scope of the appended claims. Each reference cited in the present application is incorporated herein by reference in its entirety.

What is claimed is:

1. A method of treating moderate atopic dermatitis in a human patient in need thereof comprising:
    administering to the human patient's skin a topical formulation, comprising 1.5% (w/w) on a free base basis of ruxolitinib, or a pharmaceutically acceptable salt thereof, two times per day, and
    continuing the administration of the topical formulation for at least 8 weeks,
    wherein the human patient has a Body Surface Area (BSA) of atopic dermatitis involvement ranging from 3% to 20% at baseline,
    wherein the patient has an itch Numerical Rating Scale score of ≥4 at baseline,
    wherein the human patient achieves IGA treatment success (IGA-TS) as a score of 0 (clear) or 1 (almost clear) with ≥2 grade improvement from baseline at week 8 of the administration, and
    wherein the human patient achieves at least a 4 point reduction in itch Numerical rating Scale score from baseline at week 8 of the administration.

2. The method of claim 1, wherein administering the topical formulation continues for 12 weeks.

3. The method of claim 1, further comprising stopping the administration of the topical formulation after at least 8 weeks when the patient's skin resolves the atopic dermatitis.

4. The method of claim 1, wherein the patient achieves at least a 4 point reduction in itch Numerical Rating Scale score from baseline at week 2 with administration.

5. The method of claim 1, wherein the patient achieves at least a 4 point reduction in itch Numerical Rating Scale score from baseline at week 4 of with administration.

6. The method of claim 1, wherein the ruxolitinib, or the pharmaceutically acceptable salt thereof, is ruxolitinib phosphate.

7. The method of claim 1, wherein the patient has been diagnosed with atopic dermatitis as defined by the Hanifin and Rajka criteria.

8. The method of claim 7, wherein the patient has a history of atopic dermatitis for at least 2 years.

9. The method of claim 8, wherein the ruxolitinib, or the pharmaceutically acceptable salt thereof, is ruxolitinib phosphate.

10. The method of claim 1, wherein the patient achieves an Investigator's Global Assessment score of 0 or 1 with an improvement of at least 2 points from baseline at week 2 of the administration.

11. The method of claim 1, wherein the patient achieves an Investigator's Global Assessment score of 0 or 1 with an improvement of at least 2 points from baseline at week 4 of the administration.

12. The method of claim 1, wherein the patient achieves at least a 1 point reduction in itch Numerical Rating Scale score from baseline at day 1 of the administration.

13. The method of claim 1, wherein the patient achieves at least a 1 point reduction in itch Numerical Rating Scale score from baseline at day 2 of said administration.

14. The method of claim 1, wherein the patient has a BSA of atopic dermatitis involvement of ≥10% at baseline.

15. The method of claim 14, wherein the patient has an Eczema Area and Severity Index score of ≥16 at baseline.

16. The method of claim 14, wherein the patient has been diagnosed with atopic dermatitis as defined by the Hanifin and Rajka criteria.

17. The method of claim 16, wherein the patient has a history of atopic dermatitis for at least 2 years.

18. The method of claim 17, wherein the ruxolitinib, or the pharmaceutically acceptable salt thereof, is ruxolitinib phosphate.

* * * * *